(12) United States Patent
Choi et al.

(10) Patent No.: US 12,275,740 B2
(45) Date of Patent: Apr. 15, 2025

(54) METHOD OF INHIBITING KINASE BY CAMSYLATE SALTS OF TRIAZOLOPYRAZINE DERIVATIVES

(71) Applicant: ABION Inc., Seoul (KR)

(72) Inventors: Jun Young Choi, Seoul (KR); Kyung-eui Park, Seoul (KR); Na Young Kim, Seoul (KR)

( * ) Notice: Subject to any disclaimer, the term of this patent is extended or adjusted under 35 U.S.C. 154(b) by 0 days.

(21) Appl. No.: 18/395,739

(22) Filed: Dec. 26, 2023

(65) Prior Publication Data
US 2024/0124472 A1  Apr. 18, 2024

Related U.S. Application Data

(62) Division of application No. 17/849,784, filed on Jun. 27, 2022, now Pat. No. 11,964,979.

(51) Int. Cl.
*C07D 487/04* (2006.01)

(52) U.S. Cl.
CPC ................... *C07D 487/04* (2013.01)

(58) Field of Classification Search
CPC .................................................. C07D 487/04
See application file for complete search history.

(56) References Cited

U.S. PATENT DOCUMENTS 9,403,831 B2   8/2016   Jung et al.

*Primary Examiner* — Paul V Ward

(57) ABSTRACT

Disclosed are a salt (camsylate salt) of D(+)-10-camphorsulfonic acid and a triazolopyrazine derivative of formula (1), pharmaceutical compositions thereof, methods of making the salt, and therapeutic use thereof:

Formula (1)

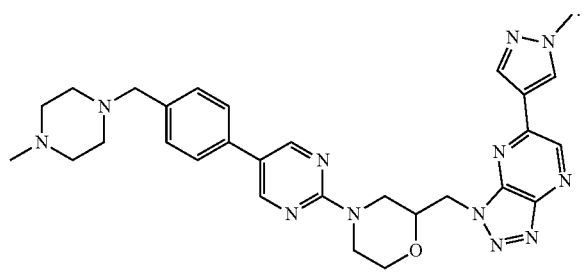

5 Claims, 46 Drawing Sheets

A

B

A

B

| Name | RT (min) | Area (mAU*s) | Height (mAU) | Area % |
|---|---|---|---|---|
| - | 1.38 | 33.1 | 7.7 | 1.9 |
| - | 1.50 | 37.6 | 18.1 | 2.1 |
| S19061_API | 1.56 | 1541.5 | 527.4 | 87.2 |
| - | 1.71 | 88.6 | 26.9 | 5.0 |
| - | 1.87 | 13.7 | 4.9 | 0.8 |
| - | 2.02 | 20.5 | 7.4 | 1.2 |
| - | 2.40 | 33.6 | 12.2 | 1.9 |

A

B

METHOD OF INHIBITING KINASE BY CAMSYLATE SALTS OF TRIAZOLOPYRAZINE DERIVATIVES

CROSS-REFERENCE TO RELATED APPLICATIONS

This application is a divisional application of U.S. patent application Ser. No. 17/849,784, filed on Jun. 27, 2022, which is hereby incorporated by reference in its entirety into the present application.

BACKGROUND

Discussion of the Related Art

Triazolopyrazine derivatives have been described in U.S. Pat. No. 9,403,831 (incorporated by reference in its entirety herein) for use in inhibiting the activity of c-Met kinase, and for treatment hyperproliferative disorders. However, these triazolopyrazine derivatives are described in a free base form rather than a salt form.

A need exists for novel salt forms of triazolopyrazine derivatives having advantageous properties while substantially retaining the pharmacokinetic and therapeutic effects of the free base form.

SUMMARY

The disclosure provides novel salt forms of triazolopyrazine derivatives represented by formula (1) with improved solubility, stability, and/or other properties while maintaining substantially similar pharmacokinetic properties of the free base form of the compounds.

Formula 1

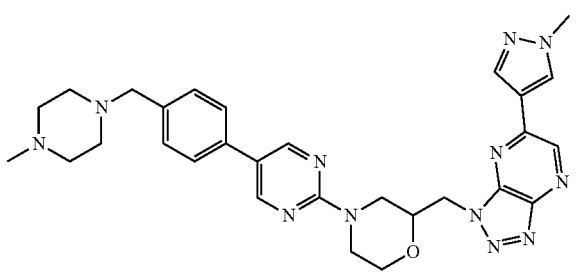

In one instance, a salt (camsylate salt) of D(+)-10-camphorsulfonic acid and a triazolopyrazine derivative of formula (1) is provided.

The disclosure also provides compositions of the camsylate salt and a pharmaceutically acceptable carrier.

The disclosure also provides a method for manufacturing the camsylate salt.

The disclosure also provides a method for inhibiting the activity of c-Met kinase in a subject by administering to a subject in need thereof a therapeutically effective amount of the camsylate salt.

DETAILED DESCRIPTION OF EXEMPLARY EMBODIMENTS

Figure 1:
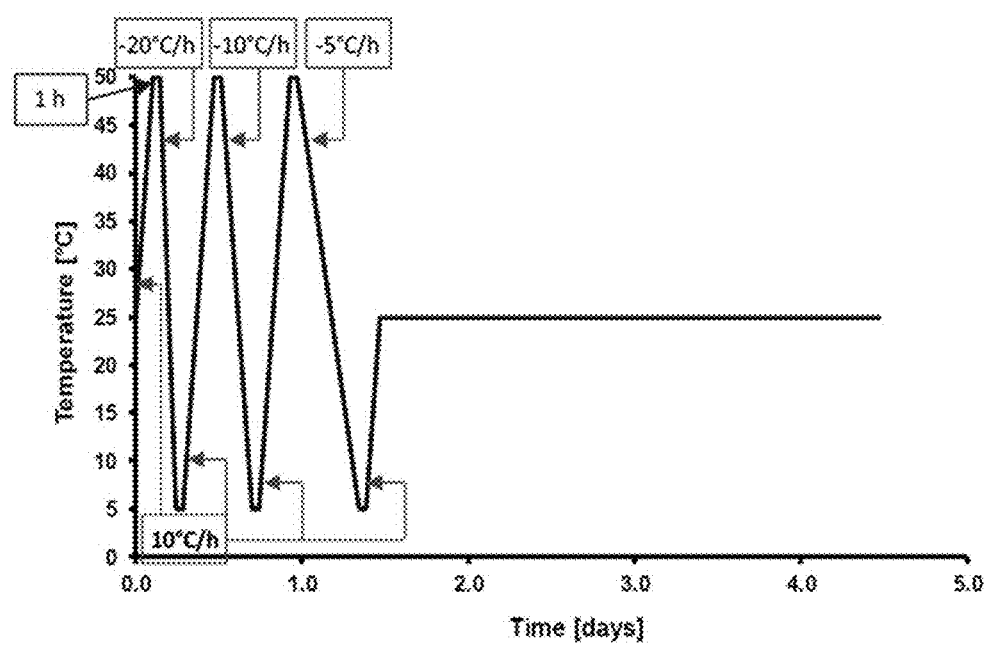
FIG. 1 shows the temperature profile applied in the salt screen experiments.

The novel salts inhibit the activity of c-Met tyrosine kinase to be useful as a therapeutic agent of various abnormal proliferative diseases associated with excessive cell proliferation and growth due to the abnormal activity of kinase, such as cancer, psoriasis, rheumatoid arthritis, and diabetic retinopathy. The present disclosure describes exemplary pharmaceutical compositions for inhibiting the activity of c-Met tyrosine kinase including novel salts as active ingredients and a pharmaceutical composition for preventing or treating hyper proliferative disorders.

In one aspect, in the camsylate salt the triazolopyrazine derivative of formula (1) is the (S) enantiomer. Preferably the triazolopyrazine derivative of formula (1) is optically pure. In an aspect, the level of optical purity is at least 95%, at least 97%, at least 99%, or essentially 100%.

In an aspect, the camsylate salt has any one salt form of Camp1, Camp2, Camp4, Camp5, or Camp6. Preferably the camsylate salt has salt form Camp2. In an aspect, the camsylate salt is physically stable at 20 to 50° C. and 35% to 80% relative humidity (RH) for at least 2 days. In an aspect, the camsylate salt is physically stable up to 24 months at ambient conditions. In an aspect, the camsylate salt has API chemical purity of at least about 95%. Preferably the camsylate salt has API chemical purity of about 97.9%.

In an aspect, the camsylate salt has a High-Throughput X-Ray Powder Diffraction (HT-XRPD) pattern comprising characteristic peaks at about 14 to 14.5 2θ (deg) and at about 16 to 17 2θ (deg). Preferably, the camsylate salt HT-XRPD pattern has characteristic peaks corresponding substantially to:

|    | 2θ [°] | d [Å] | Intensity | or |    | 2θ [°] | d [Å] | Intensity |
|----|--------|-------|-----------|----|----|--------|-------|-----------|
| 1  | 6.29   | 14.04 | 31        |    | 1  | 6.34   | 13.92 | 22        |
| 2  | 10.31  | 8.57  | 38        |    | 2  | 10.36  | 8.53  | 28        |
| 3  | 12.20  | 7.25  | 45        |    | 3  | 12.03  | 7.35  | 28        |
| 4  | 13.70  | 6.46  | 41        |    | 4  | 12.26  | 7.21  | 28        |
| 5  | 14.32  | 6.18  | 94        |    | 5  | 13.80  | 6.41  | 42        |
| 6  | 15.54  | 5.70  | 60        |    | 6  | 14.33  | 6.18  | 100       |
| 7  | 16.92  | 5.24  | 100       |    | 7  | 14.94  | 5.92  | 39        |
| 8  | 18.19  | 4.87  | 35        |    | 8  | 15.52  | 5.70  | 46        |
| 9  | 20.12  | 4.41  | 46        |    | 9  | 16.83  | 5.26  | 72        |
| 10 | 21.57  | 4.12  | 43        |    | 10 | 18.26  | 4.85  | 27        |
| 11 | 23.36  | 3.81  | 31        |    | 11 | 20.11  | 4.41  | 33        |
| 12 | 24.19  | 3.68  | 37        |    | 12 | 21.14  | 4.20  | 25        |
| 13 | 26.46  | 3.37  | 26        |    | 13 | 21.42  | 4.14  | 28        |
| 14 | 27.79  | 3.21  | 23        |    | 14 | 22.35  | 3.98  | 21        |
| 15 | 28.84  | 3.09  | 21        |    | 15 | 23.42  | 3.80  | 24        |
| 16 | 29.50  | 3.03  | 22        |    | 16 | 23.92  | 3.72  | 24        |
|    |        |       |           |    | 17 | 26.38  | 3.38  | 18        |
|    |        |       |           |    | 18 | 27.92  | 3.19  | 16        |
|    |        |       |           |    | 19 | 28.83  | 3.09  | 19        |
|    |        |       |           |    | 20 | 29.59  | 3.02  | 15        |

In an aspect, a method for manufacturing the camsylate salt is provided, including steps of a) adding a compound of formula (1) to a reactor containing a solvent; (b) stirring the compound and the solvent in the reactor; (c) adding D(+)-10-camphorsulfonic acid to the solution prepared in (b); and (e) cooling the solution prepared in (c) to obtain a precipitate of the camsylate salt. In an aspect, the solvent may be acetonitrile, acetone, 1,2-dimethoxyethane, n-heptane, isopropyl alcohol, water, or THF. In an aspect, the D(+)-10-camphorsulfonic acid is added to the solution prepared in (b) in an equivalent ratio of about 1:0.5 to about 1:1.5 with respect to formula (1). Preferably, the equivalent ratio is about 1:1.0 to about 1:1.2 and the solvent comprises acetonitrile. In an aspect, step (b) is performed at about 45 to 55° C. for at least about 1 hour.

In another aspect, a pharmaceutical composition is provided, including the camsylate salt and a pharmaceutically acceptable carrier. The pharmaceutically acceptable carrier may be one or more of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil. The pharmaceutical composition may include one or more of a lubricant, a wetting agent, a sweetening agent, a flavoring agent, an emulsifying agent, a suspending agent, and a preservative.

In another aspect, a method is provided for inhibiting the activity of c-Met kinase in a subject by administering to a subject in need thereof a therapeutically effective amount of the camsylate salt. In an aspect, the subject is suffering from a hyperproliferative disorder. Examples of the hyperproliferative disorder include lung cancer, gastric cancer, pancreatic cancer, colon cancer, ovarian cancer, renal cell cancer, prostate cancer, or a brain tumor. In an aspect, the method is for treating or preventing such hyperproliferative disorders.

Abbreviations

| General | |
|---------|---|
| AAC     | Accelerated Ageing Conditions (40° C./75% RH) |
| Am      | Amorphous |
| API     | Active Pharmaceutical Ingredient |
| CI      | Counterion |
| DSC     | Differential Scanning Calorimetry |
| DVS     | Dynamic Vapor Sorption |
| 1H-NMR  | Proton Nuclear Magnetic Resonance |
| LCMS    | High-Performance Liquid Chromatography |
| HR-XRPD | High Resolution X-Ray Powder Diffraction |
| HT-XRPD | High Throughput X-Ray Powder Diffraction |
| LCMS    | Liquid Chromatography Mass spectroscopy |
| ML      | Mother liquor (liquid phases) |
| MS      | Mass Spectroscopy |
| RH      | Relative Humidity |
| RT      | Room Temperature |
| SAS     | Experiment ID for the solubility assessment experiments |
| SSm     | Experiment ID for the salt screening experiments |
| SM      | Starting Material |
| TGA     | Thermogravimetric Analysis |
| TGMS    | Thermogravimetric Analysis coupled with Mass Spectroscopy |

| Solvents | |
|----------|---|
| ACN      | Acetonitrile |
| IPA      | 2-Propanol |
| MTBE     | tert-Butyl methyl ether |
| THF      | Tetrahydrofuran |

| Counterions | |
|-------------|---|
| HCl  | Hydrochloride acid |
| Mes  | Methanesulfonic acid |
| Bes  | Benzenesulfonic acid |
| Mae  | Maleic acid |
| Esy  | Ethanesulfonic acid |
| Camp | D(+)-10-Camphorsulfonic acid |
| Mao  | Malonic acid |
| Fum  | Fumaric acid |
| Cit  | Citric acid |
| Mal  | (−)-L-Malic acid |
| Suc  | Succinic acid |
| Gal  | Gallic acid |

While the present disclosure is described in more detail through the following Examples, the scope of the present disclosure is not intended to be limited thereby.

EXAMPLES

The compound of formula (1) ("ABN-401") was provided by Abion. All other chemicals were obtained from Fisher Scientific, Sigma Aldrich or VWR. Chemicals used are at least of research grade. The solvents used for LCMS analysis are of LCMS grade.

Solubility Determinations

The approximate solubility was determined by adding small aliquots of solvent (50 μL up to 1 mL, 100 μL above 1 mL) to the solid starting material until complete dissolution was observed or a maximum volume of 4 mL was reached. Afterwards the solvents were evaporated and obtained solids were analyzed by HT-XRPD. The experimental details and results are reported in Table 1.

TABLE 1

Experimental conditions and results of the solubility determination on ABN-401. Aliquots of solvent were added to the solid until complete dissolution was observed. XRPD: in brackets Abion's classification.

| Exp. ID | Solvent | Mass (mg) | Final volume (L) | Dissolved | Solubility (mg/mL) | XRPD |
|---|---|---|---|---|---|---|
| SAS1 | Acetone | 7.72 | 350 | Yes | 22.1-25.6 | A (I) |
| SAS2 | Acetonitrile | 13.42 | 1700 | Yes | 7.9 ≤ S ≤ 8.4 | B (IV) |
| SAS3 | Chloroform | 15.57 | 50 | Yes | >311.4 | C |
| SAS4 | 1,4-Dioxane | 9.97 | 50 | Yes | >199.4 | A (I) |
| SAS5 | Ethyl acetate | 14.22 | 3200 | Yes | 4.4-4.6 | A (I) |
| SAS6 | 1,2-Dimethoxyethane | 16.52 | 1300 | Yes | 12.7-13.8 | A (I) |
| SAS7 | Isopropanol | 10.68 | 4000 | No | <2.7 | A (I) |
| SAS8 | Methanol | 11.37 | 4000 | No | <2.9 | D (II) |
| SAS9 | Tetrahydrofuran | 9.03 | 50 | Yes | >180.6 | A (I) |
| SAS10 | Water | 12.49 | 4000 | No | <3.1 | E |

Thermal Stability

A thermal stability study was performed on ABN-401 to investigate the chemical stability of the starting material in solution when exposed to elevated temperatures. Solutions of ABN-401 were prepared in acetone, 1,2-dimethoxyethane, and acetonitrile with a concentration of approximately 0.3 mg/mL. Solutions were left at RT for 1 hour and successively, two aliquots of each solution were taken and heated at 50° C. and 80° C. for one hour. All these solutions were analyzed by LCMS. Additionally, the samples kept at RT were remeasured by LCMS after 24 hours to check the chemical degradation over time. No significant chemical degradation was observed in the samples kept at 50° C. and 80° C. The results are summarized in Table 2.

TABLE 2

Results of the LCMS analyses of the thermal stability study.

| Solvent | Conditions | Rt (min) | Area % | Area counts | Peak height (mAu) |
|---|---|---|---|---|---|
| Acetone | 1 h/RT | 5.2 | 98.8 | 5905.0 | 1181.0 |
| Acetone | 24 h/RT | 5.2 | 98.5 | 5843.1 | 1161.5 |
| Acetone | 1 h/50° C. | 5.2 | 99.0 | 5883.8 | 1168.2 |
| Acetone | 1 h/80° C. | 5.2 | 99.0 | 5843.1 | 1169.4 |
| 1,2-dimethoxyethane | 1 h/RT | 5.2 | 99.0 | 6751.7 | 1341.1 |
| 1,2-dimethoxyethane | 24 h/RT | 5.2 | 98.8 | 6745.1 | 1339.0 |
| 1,2-dimethoxyethane | 1 h/50° C. | 5.2 | 98.6 | 6653.6 | 1326.3 |
| 1,2-dimethoxyethane | 1 h/80° C. | 5.2 | 97.7 | 6697.6 | 1335.6 |
| ACN | 1 h/RT | 5.2 | 99.0 | 6420.0 | 1260.0 |
| ACN | 24 h/RT | 5.2 | 98.1 | 6414.1 | 1255.0 |
| ACN | 1 h/50° C. | 5.2 | 99.0 | 6413.9 | 1258.7 |
| ACN | 1 h/80° C. | 5.2 | 98.7 | 6445.2 | 1263.4 |

Salt Screen Experiments

The screen was started by preparing solutions of ABN-401 in acetone, 1,2-dimethoxyethane, and acetonitrile with a concentration of around 25, 13 and 8 mg/mL, respectively. Counterions were added to the API solutions from aqueous solutions, resulting in API:counterion ratios of 1:1.1, 1:2.1 and 1:3.1. The experiments were subjected to a temperature profile including three heating-cooling cycles between 5-50° C. and aging at 25° C. for 3 days (FIG. 1).

Upon completion of the aging time, the solids were separated from the liquid phases, dried under vacuum at 50° C. and analyzed by HT-XRPD. The solutions (from the experiments that did not show solids after the temperature profile) and the mother liquors were left to evaporate at room conditions, and the residual solids were analyzed by HT-XRPD. Subsequently, all the solids were exposed to accelerated aging conditions (AAC) at 40° C./75% RH for 48 hours and re-measured by HT-XRPD to test their physical stability.

Scale-Up of Salts

The camsylate salt, Camp2, was scaled-up at 0.3-gram scale (Exp. ID SSm73). 300 mg of free base was dissolved in 15 mL of ACN (concentration=20 mg/mL) at 50° C. Camphor-10-sulfonic acid (136 mg) was added to reach an API:CI molar ratio of 1:1.1. The counterion dissolved, and the solution was left to equilibrate with continuous stirring at 50° C. for 1 hour. The solution was cooled down to 25° C. and aged for 72 hours. The salt had precipitated during the cooling profile. The solids were isolated, dried under deep vacuum (10 mbar at 50° C.) and analyzed by HT- and HR-XRPD, TGA/TGMS, DSC, LCMS, 1H-NMR and DVS.

The mesylate salt, Mes2, was scaled-up to 0.5-gram scale (Exp. ID SSm71). 500 mg of the free base was dissolved in 23 mL of acetone (concentration=26 mg/mL) at RT. Methanesulfonic acid (1M water solution) was added to reach an API:CI molar ratio of 1:2.1. Precipitation of the salt was observed upon addition of the counterion. The suspension was heated to 50° C. and left to equilibrate with continuous stirring at 50° C. for 8 hours. The salt suspension was cooled down to 25° C. The solids were isolated, dried under deep vacuum (10 mbar at 50° C.) and analyzed by HT- and HR-XRPD, TGA/TGMS, DSC, LCMS, 1H-NMR and DVS.

The maleate salt, Mae2, was scaled-up at 0.3-gram scale (Exp. ID SSm75). 300 mg of free base was mixed in 5 mL of acetone (concentration=60 mg/mL) at 50° C. (suspension). To the free base suspension maleic acid (130 mg) was added to reach an API:CI molar ratio of 1:2.1. The suspension was left to equilibrate with continuous stirring at 50° C. for 1 hour. The salt suspension was cooled down to 25° C. and aged for 72 hours at RT. The suspension had become very thick and 2 mL of acetone were added and the vial shaken, to ensure removal of unreacted API or maleic acid. The solids were isolated, dried under deep vacuum (10 mbar at 50° C.) and analyzed by HT- and HR-XRPD, TGA/TGMS, DSC, LCMS, 1H-NMR and DVS.

Physical and Chemical Stability

Physical stability studies (see Table 3) over a prolonged period of time (up to 2 years) were conducted at defined temperatures and relative humidity values (25° C./60% RH and 40° C./75% RH) on the camsylate (Camp2), maleate (Mae2) and mesylate (Mes2) salts. As a reference, a sample of ABN-401 free base was also included in this stability study. At timepoints of 1, 3, 15 and 24 months, the vials containing the solid were analyzed by XRPD, TGMS and HPLC to determine if changes in the solid form had occurred, to confirm the water/solvent content and if chemical degradation occurred after storage at the different conditions.

TABLE 3

Experimental conditions for the stability study performed on the camsylate (Camp2), maleate (Mae2), mesylate (Mes2) salts and ABN-401 free base (FB).

| Exp ID | Condition | Salt form | Time | Mass (mg) |
|---|---|---|---|---|
| GEN50 | 25° C./60% RH | Camp2 | 1 month | 28.8 |
| GEN51 | | | 3 months | 23.7 |
| GEN52 | | | 15 months | 23.5 |
| GEN53 | | | 24 months | 19.2 |
| GEN54 | 40° C./75% RH | | 1 month | 26.8 |
| GEN55 | | | 3 months | 21.6 |
| GEN56 | | | 15 months | 18.4 |
| GEN57 | | | 24 months | 19.1 |
| GEN58 | 25° C./60% RH | Mae2 | 1 month | 20.7 |
| GEN59 | | | 3 months | 19.1 |
| GEN60 | | | 15 months | 23.8 |
| GEN61 | | | 24 months | 22.3 |
| GEN62 | 40° C./75% RH | | 1 month | 17.4 |
| GEN63 | | | 3 months | 17.0 |
| GEN64 | | | 24 months | 17.4 |
| GEN65 | | | 15 months | 22.5 |
| GEN66 | 25° C./60% RH | Mes2 | 1 month | 23.2 |
| GEN67 | | | 3 months | 23.2 |
| GEN68 | | | 15 months | 29.9 |
| GEN69 | | | 24 months | 23.5 |
| GEN70 | 40° C./75% RH | | 1 month | 27.3 |
| GEN71 | | | 3 months | 20.3 |
| GEN72 | | | 24 months | 26.9 |
| GEN73 | | | 15 months | 23.1 |
| GEN78 | 25° C./60% RH | FB | 1 month | 21.0 |
| GEN79 | | | 3 months | 22.3 |
| GEN80 | | | 15 months | 19.5 |
| GEN81 | | | 24 months | 20.6 |
| GEN74 | 40° C./75% RH | | 1 month | 18.9 |
| GEN75 | | | 3 months | 21.4 |
| GEN76 | | | 24 months | 20.1 |
| GEN77 | | | 15 months | 22.1 |

Polymorph Screen on Maleate and Camsylate Salts

The polymorphic behavior of the maleate and camsylate salts was evaluated by thermocycling in 15 solvents. The salts were prepared by freeze-drying to attempt the preparation of amorphous salts. Several attempts were carried out, and the experimental conditions are described in Table 4.

Based on the results, the best conditions were reproduced at large scale to produce material for the polymorph screen. The scale-up conditions were as follows:

A solution of ABN-401 (735 mg) was prepared in 1,4-dioxane/water (50/50) containing 1 molar equivalent of camphor-10-sulfonic acid, concentration of 147 mg/mL (Exp. ID GEN10). The solution was liquid dosed in 16 vials.

A solution of ABN-401 (722 mg) in the presence of 2 molar equivalents of maleic acid was prepared in THF/water (50/50), concentration of 60 mg/mL (Exp. ID GEN11). The solution was liquid dosed in 16 vials.

The solutions were frozen in liquid nitrogen and placed under deep vacuum using a freeze dryer (Alpha 2-4 LD, Christ). One sample of the freeze dried solids was analyzed by HT-XRPD, by TGMS to determine the solvent content and by 1H-NMR to confirm salt formation.

To the vials containing the (low crystalline) salts, aliquots of solvent were added until a thin suspension was obtained.

Figure 2:
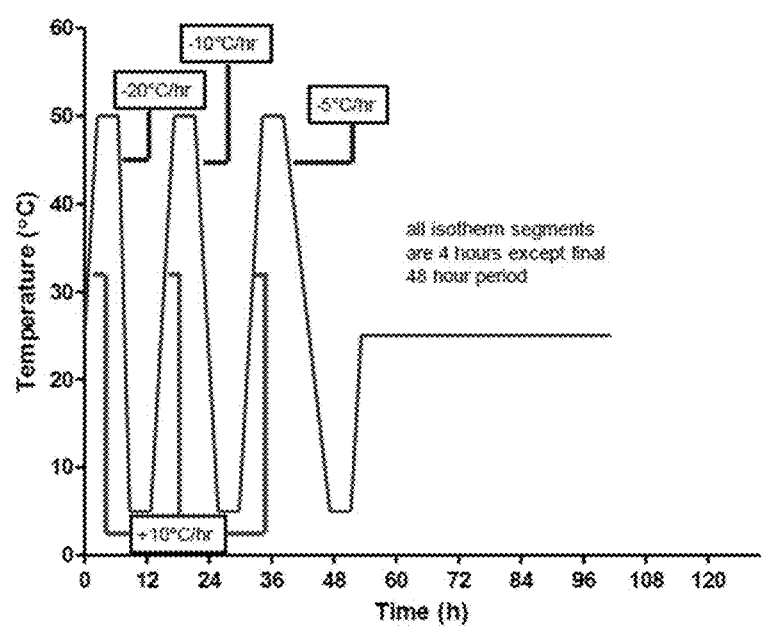
FIG. 2 shows the temperature profile of the thermocycling experiments.
Figure 3:
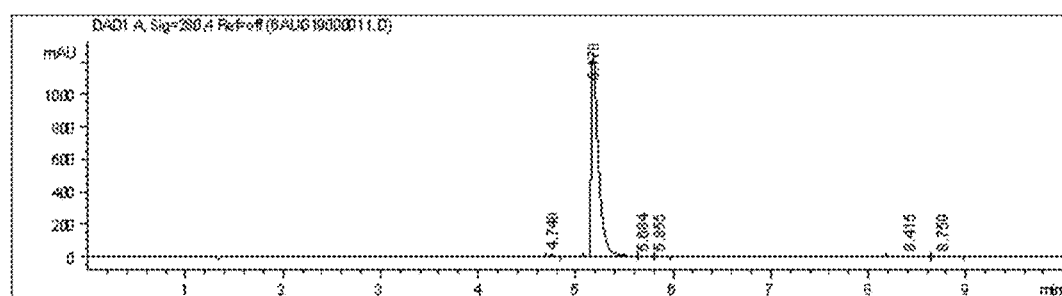
FIG. 3 shows LCMS analysis of ABN-401, starting material using method S19061_03. Retention time=5.2 min.
Figure 4:
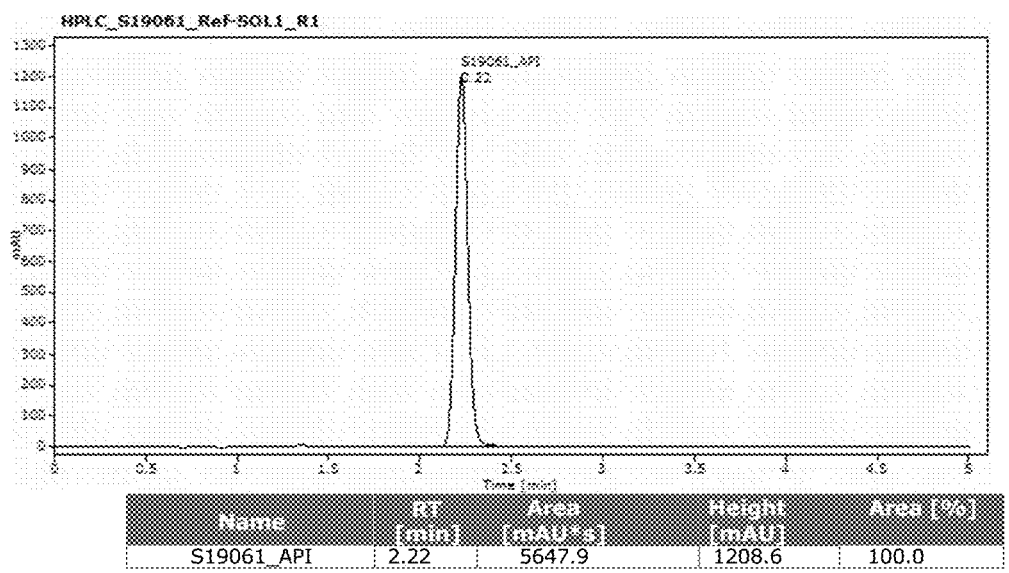
FIG. 4 shows LCMS analysis of ABN-401, starting material using method S19061_01. Retention time=2.2 min

The vials were subjected to a temperature profile including 3 thermocycles between 50-5° C. and aged at RT for 2 days, according to the profile shown in FIG. 2.

After the temperature profile, the solid phase and liquid phase were separated. The solids were analyzed after drying under vacuum (10 mbar) at 50° C. overnight. An aliquot of mother liquor was taken from each experiment, filtered and analyzed by HPLC. The API concentration in solution was calculated against a calibration line, made with two stock solutions.

The solvents from the liquid phases were evaporated at ambient conditions and the recovered solids analyzed by XRPD. Subsequently all solids were exposed to accelerated aging conditions (AAC, 40° C./75% RH) for two days and reanalyzed by HT-XRPD.

High Throughput X-Ray Powder Diffraction

HT-XRPD patterns were obtained using the Crystallics T2 high-throughput XRPD set-up. The plates were mounted on a Bruker General Area Detector Diffraction System (GADDS) equipped with a VANTEC-500 gas area detector corrected for intensity and geometric variations. The calibration of the measurement accuracy (peaks position) was performed using NIST SRM1976 standard (Corundum).

Data collection was carried out at room temperature using monochromatic Cu Kα radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure

TABLE 4

Experimental conditions for the freeze-drying attempts to get amorphous salts.
The notation (lc) indicates that poorly crystalline material was recovered.

| Exp ID | Comment | Mass FB (mg) | Solvent description | Solvent volume (µL) | Concentration (mg/mL) | Dissolved at initial T | Form |
|---|---|---|---|---|---|---|---|
| GEN1 | FD (Camp salt) | 50.0 | 1,4-Dioxane/Water (90/10) | 300 | 166.7 | Yes | Camp4 (lc) |
| GEN2 | FD (Camp salt) | 50.0 | 1,4-Dioxane/Water (80/20) | 300 | 166.7 | Yes | Am |
| GEN3 | FD (Camp salt) | 50.0 | 1,4-Dioxane/Water (50/50) | 300 | 166.7 | Yes | Am |
| GEN4 | FD (Mae salt) | 50.0 | 1,4-Dioxane/Water (90/10) | 900 | 55.6 | No | Am |
| GEN5 | FD (Mae salt) | 50.0 | 1,4-Dioxane/Water (80/20) | 900 | 55.6 | No | Mae1 (lc) |
| GEN6 | FD (Mae salt) | 50.0 | 1,4-Dioxane/Water (50/50) | 900 | 55.6 | No | Mae1 (lc) |
| GEN7 | FD (Mae salt) | 50.0 | THF/Water (50/50) | 800 | 62.5 | Yes | Am |
| GEN8 | ED (Mae salt) | 50.0 | THF/Water (80/20) | 1200 | 41.7 | No | Am |
| GEN9 | FD (Mae salt) | 50.0 | THF/Water (90/10) | 900 | 55.6 | No | Mae1 (lc) |
| GEN10 | FD (Camp salt) | 734.9 | 1,4-Dioxane/Water (50/50) | 5000 | 147.0 | Yes | Camp4 |
| GEN11 | FD (Mae salt) | 721.9 | THF/Water (50/50) | 12000 | 60.2 | Yes | lc | time of 90 s for each frame. No background subtraction or curve smoothing was applied to the XRPD patterns. The carrier material used during HT-XRPD analysis was transparent to X-rays and contributed only slightly to the background.

High Resolution X-Ray Powder Diffraction

The powder data were collected on D8 Advance diffractometer using Cu K 1 radiation (1.54056 Å) with germanium monochromator at Room Temperature. The data were collected from 4 to 45 2 with 0.016 2 steps on solid state LynxEye detector with 22 sec/step speed. The sample was measured in 8 mm long glass capillary with 0.3 mm outer diameter.

TGMS Analysis

Mass loss due to solvent or water loss from the crystals was determined by TGA. Monitoring the sample weight, during heating in a TGA/DSC 3+ STARe system (Mettler-Toledo GmbH, Switzerland), resulted in a weight vs. temperature curve and a heat flow signal. The TGA/DSC 3+ was calibrated for temperature with samples of indium and aluminum. Samples (circa 2 mg) were weighed into 100 μL aluminum crucibles and sealed. The seals were pin-holed, and the crucibles heated in the TGA from 25 to 300° C. at a heating rate of 10° C./min. Dry N2 gas was used for purging.

The gases coming from the TGA samples were analyzed by a mass spectrometer Omnistar GSD 301 T2 (Pfeiffer Vacuum GmbH, Germany). The latter is a quadrupole mass spectrometer, which analyzes masses in the temperature range of 0-200 amu.

DSC Analysis

The DSC thermograms were recorded with a heat flux DSC3+ STARe system (Mettler-Toledo GmbH, Switzerland). The DSC3+ was calibrated for temperature and enthalpy with a small piece of indium (m.p.=156.6° C.; δHf=28.45 J/g) and zinc (m.p.=419.6° C.; δHf=107.5 J/g). Samples were sealed in standard 40 μL aluminum pans, pin-holed and heated in the DSC from 25 to 300° C., at a heating rate of 10° C./min. Dry N2 gas, at a flow rate of 50 mL/min was used to purge the DSC equipment during measurement.

$^1$H-NMR Analysis

The $^1$H-NMR spectra were recorded at RT on a 500 MHz Bruker instrument using standard pulse sequences. The samples were dissolved and analyzed in DMSO-$d_6$. The data were processed with ACD Labs software Spectrus Processor 2016.2.2 (Advanced Chemistry Development Inc., Canada).

LCMS Analysis

Starting material characterization and purity assessment of the novel crystalline forms of the free base:
Method name: S19061_03.M
Sample:
Concentration: 0.3 mg/ml
Diluent: Acetonitrile

TABLE 5

| Instrument | Agilent 1200 series with diode array UV detector |
|---|---|
| Mobile phase A | 10 mM Ammonium acetate in Water |
| Mobile phase B | Acetonitrile |
| Column | Waters Sunfire C18 (100 × 4.6 mm; 3.5 μm). |
| Detection: | UV at 280 nm, bandwidth 4 nm, UV spectrum 200 to 400 nm |
| Flow: | 1.0 mL/min. |
| Run time | 10 minutes |

TABLE 5-continued

| Injection volume | 5 μL |
|---|---|
| Column temp. | 35° C. |
| Autosampler temp. | Ambient |

| | Time [min.] | Eluent A [%] | Eluent B [%] |
|---|---|---|---|
| Gradient: | 0 | 90 | 10 |
| | 2.5 | 50 | 50 |
| | 8 | 10 | 90 |
| | 10 | 90 | 10 |

Assay and purity assessment of the novel crystalline salts
Method name: S19061_01.M
Sample:
Concentration: 0.3 mg/ml
Diluent: Acetonitrile/water (50/50)

TABLE 6

| Instrument | Agilent 1260 series with diode array UV detector |
|---|---|
| Mobile phase A | 20 mM Ammonium carbonate, pH = 9.4 |
| Mobile phase B | ACN:IPA:water:TFE (68:22:9:1) |
| Column | Waters XBridge BEH C18 (100 × 4.6 mm; 3.5 μm) |
| Detection: | UV at 282 nm, bandwidth 4 nm, UV spectrum 200 to 400 nm |
| Flow: | 1.4 mL/min. |
| Run time | 10 minutes |
| Injection volume | 5 μL |
| Column temp. | 60° C. |
| Autosampler temp. | Ambient |

| | Time [min.] | Eluent A [%] | Eluent B [%] |
|---|---|---|---|
| Gradient: | 10 | 60 | 40 |

DVS Analysis

Differences in hygroscopicity (moisture uptake) of the various forms of a solid material provided a measure of their relative stability at increasing relative humidity. Moisture sorption isotherms of small samples were obtained using a DVS-1 system from Surface Measurement Systems (London, UK); this instrument is suitable for use with as little as a few milligrams of sample, with an accuracy of 0.1 μg. The relative humidity was varied during sorption-desorption-sorption (40-95-0-40% RH) at a constant temperature of 25° C., typically with a hold time of 60 minutes per step (10% relative humidity step). At the end of the DVS experiment the sample was measured by XRPD.

Figure 5:
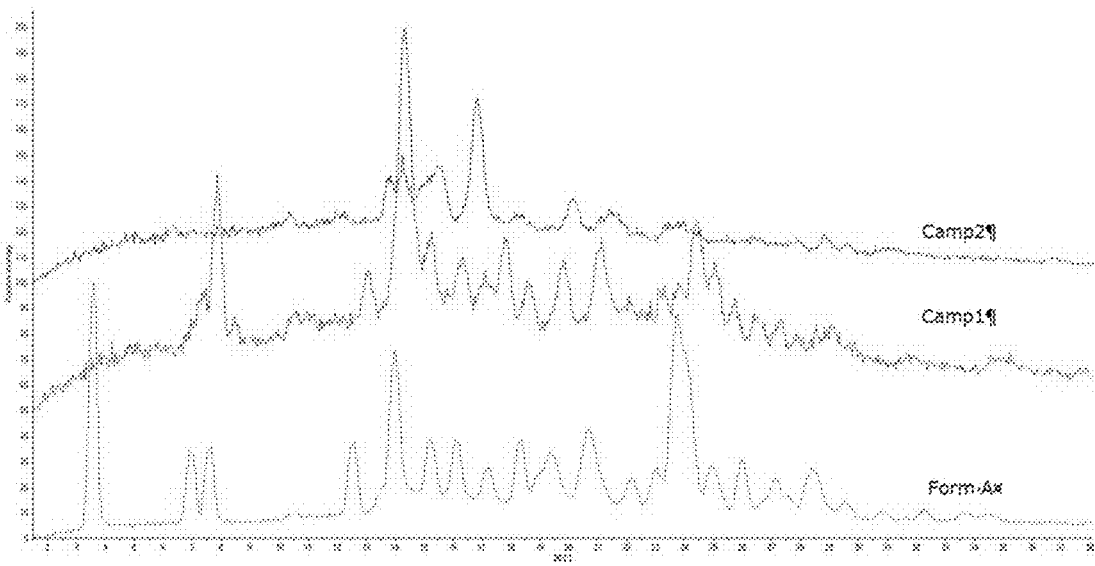
FIG. 5 shows HT-XRPD patterns (from bottom to top) of starting material (Form A), Camp1 and Camp2.

The hygroscopicity was classified according to the European Pharmacopoeia Hygroscopicity classification. Water uptake percentage at 25° C./80% RH (24 h) is:
Change in mass<0.2%—Non-hygroscopic
Change in mass>0.2% & <2%—Slightly hygroscopic
Change in mass>2% & <15%—Moderately hygroscopic
Change in mass>15%—Very hygroscopic Camsylate Salts FIG. 5 shows the HT-XRPD patterns of the camsylate salts compared to that of the starting material (Form A).

Figure 6:
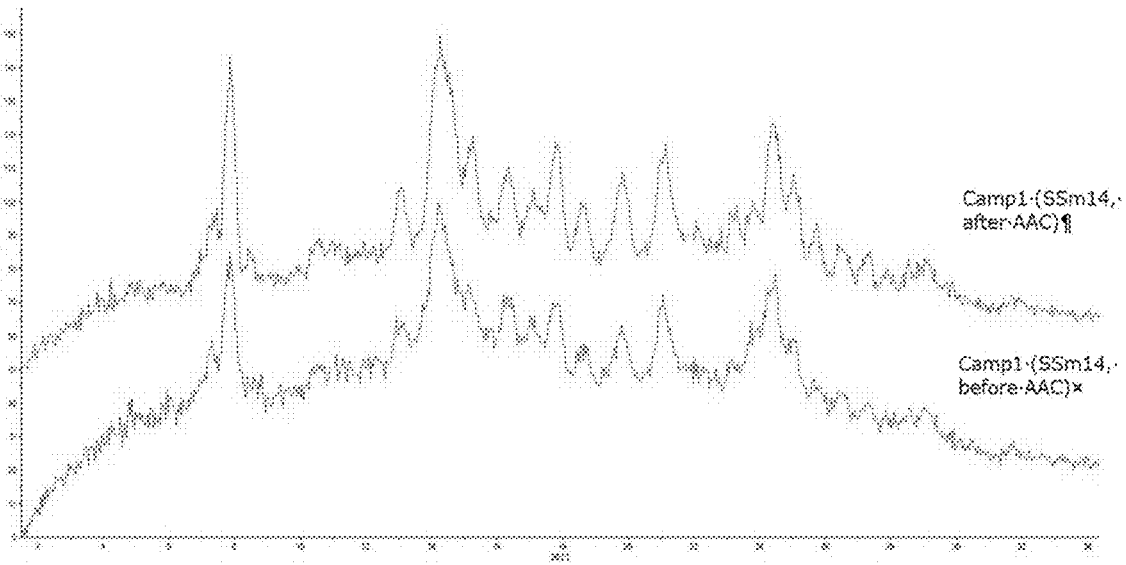
FIG. 6 shows HT-XRPD patterns of Exp. ID SSm14 before (bottom) (Camp1) and after (top) (Camp1) exposure to AAC (40° C./75% RH) for 2 days.

Camp1 was obtained from the salt formation experiments performed with camphor-10-sulfonic acid in acetone and 1,2-dimethoxyethane when an API:CI ratio of 1:1 was applied. Table 7 reports the experimental conditions producing Camp1. The solid selected for further characterization was the salt crystallized from acetone with one molar equivalent of camphor-10-sulfonic acid (Exp. ID SSm14). Camp1 was physically stable upon exposure to AAC (40° C./75% RH) for 2 days (FIG. 6).

TABLE 7

Experimental conditions producing Camp1.

| Exp. ID | API:CI Ratio 1:x | Solvent | Form | Form after AAC |
|---|---|---|---|---|
| SSm14 | 1 | Acetone | Camp1 | Camp1 |
| SSm37 | 1 | 1,2-Dimethoxyethane | Camp1 | Camp1 |

Figure 7:
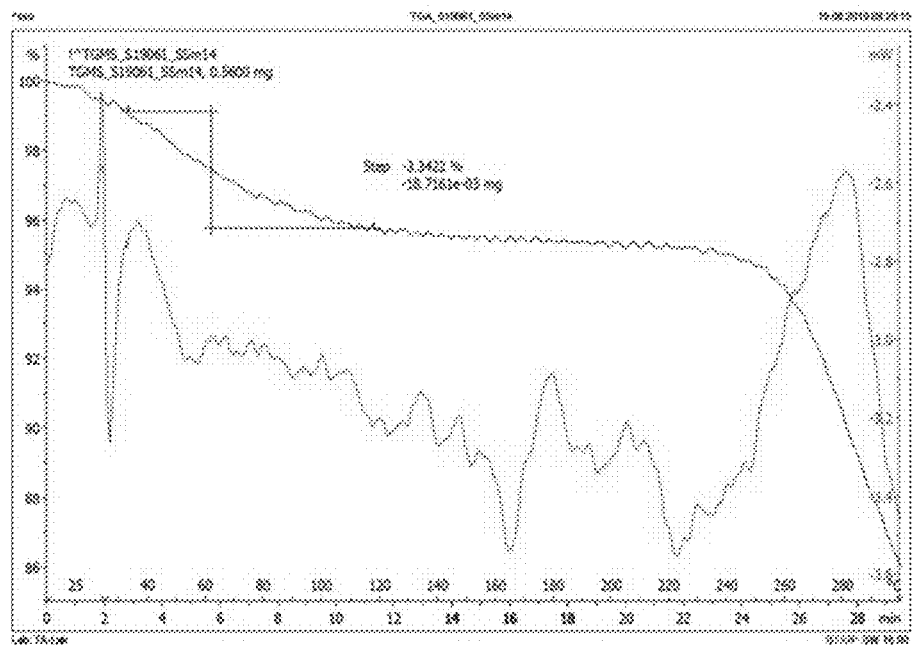
FIG. 7 shows TGA (A) and TGMS (B) analysis (heating rate of 10° C./min) of Camp1 (Exp. ID SSm14). A mass loss of 3.3% attributed to water was observed between 25-120° C. Thermal decomposition of the salt was observed above 240° C. The heat flow signal of the TGA showed an endotherm at 160° C., possibly attributed to the melting of an anhydrous phase of the salt.
Figure 7:
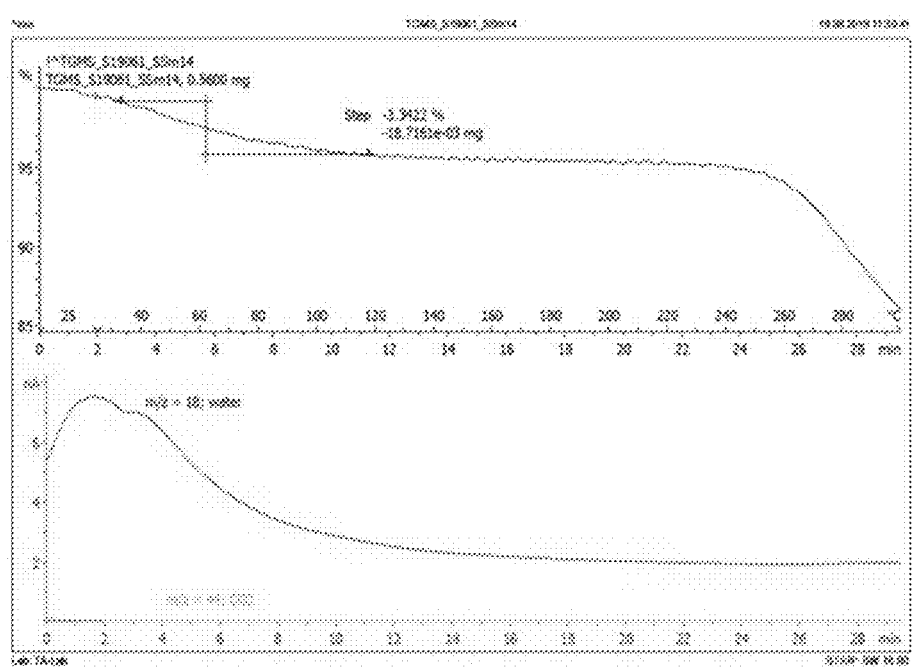

The TGA/TGMS analysis of Camp1 (FIG. 7) showed a mass loss of 3.3% from 25 to 120° C. attributed to most likely water (3.3% corresponds to 1.5 molecule of water per salt molecule). The thermal decomposition is observed at temperatures above 240° C. In the heat flow signal a sharp endothermic event was observed at around 160° C. possibly attributed to the melting of an anhydrous phase of the salt.

Figure 8:
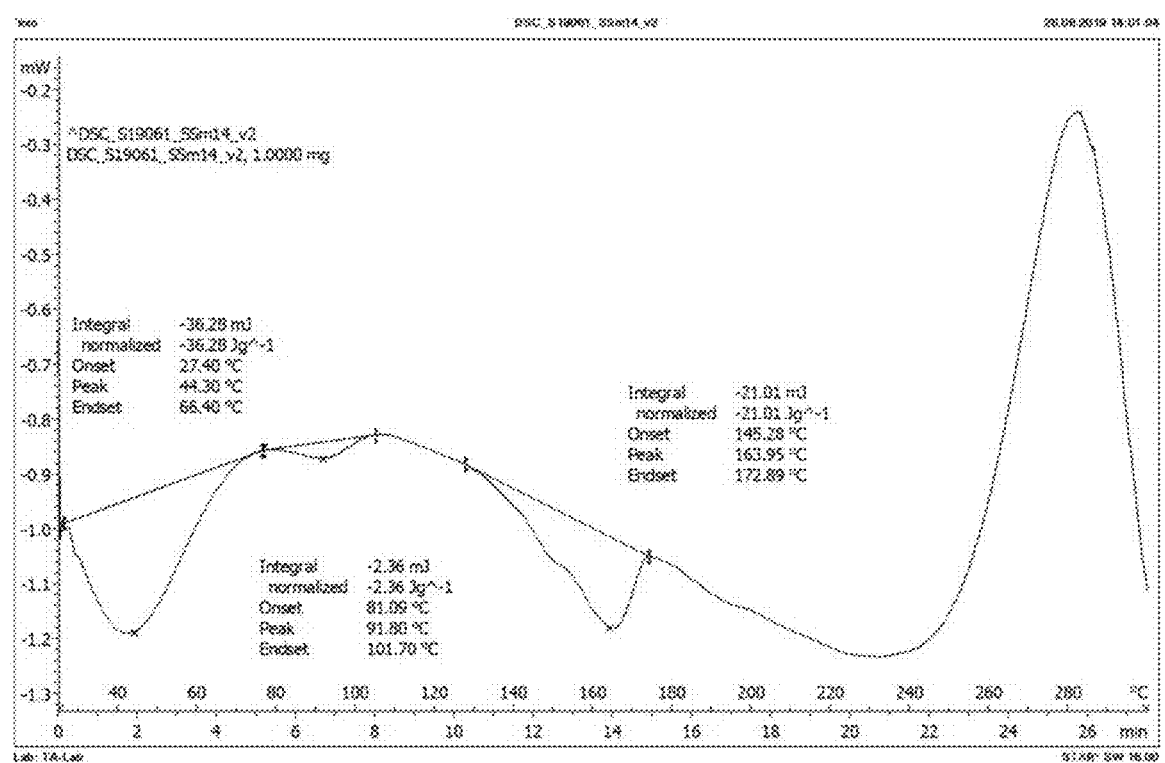
FIG. 8 shows DSC curve (heating rate 10° C./min) of Camp1 (Exp. ID SSm14). The DSC curve showed broad endothermic events between 25 to 100° C. that can be related to the water loss. A broad endothermic event at 164.0° C. that can be attributed to the melting of a potential anhydrous salt was observed.

The DSC trace of Camp1 (FIG. 8) showed broad endothermic events between 25 to 120° C., that could be related to the water loss. An endothermic event was observed at 164.0° C. that could be related to the melting of a potential anhydrous salt.

Figure 9:
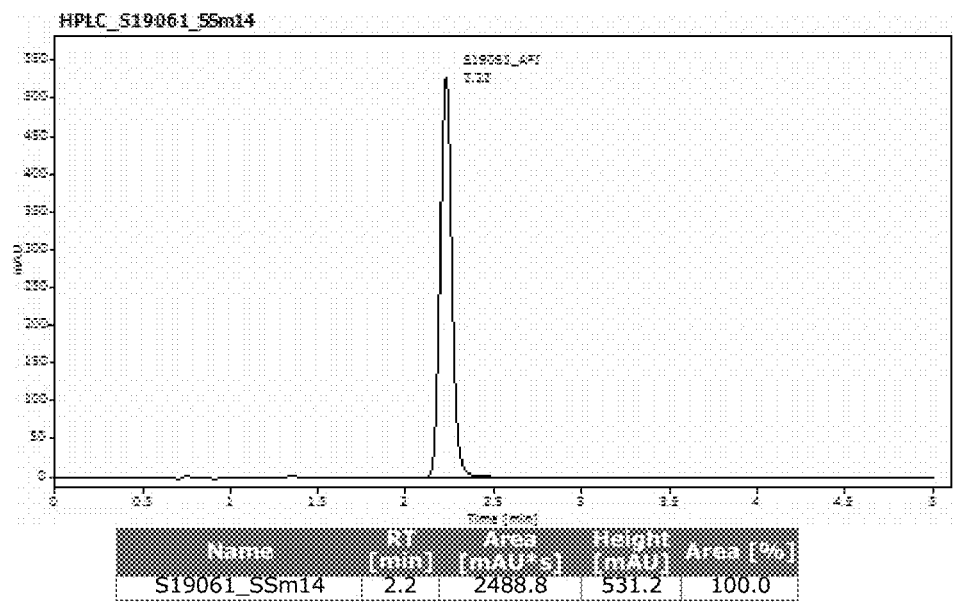
FIG. 9 shows LCMS chromatogram of Camp1 (Exp. ID SSm14). The API chemical purity was 100% (area %).

The chemical purity of Camp1 was assessed by LCMS to 100% (FIG. 9) confirming that the API was present in the solid phase Camp1.

Figure 10:
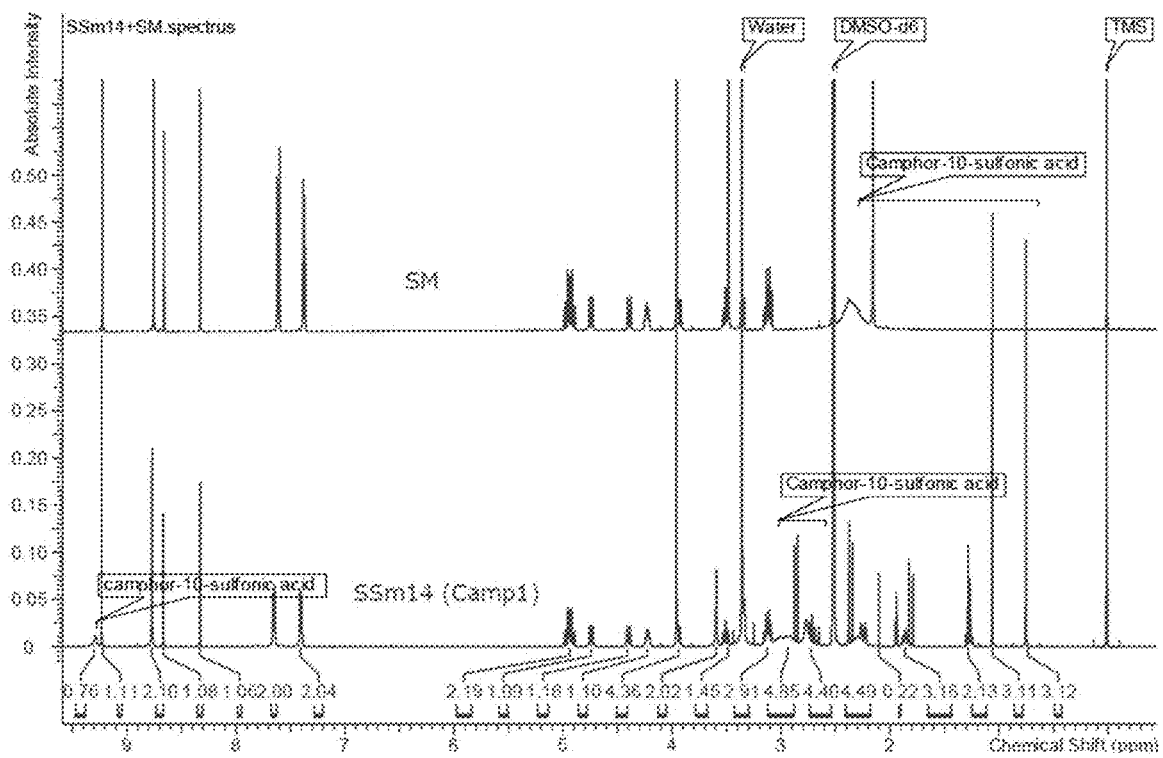
FIG. 10 shows Overlay of $^1$H-NMR spectra (500 MHz, DMSO-d6) of ABN-401 free base (green line) and Camp1 (Exp. ID SSm14, red line). The peaks corresponding to the CI were highlighted by the signal at 9.3, 3.0, 2.7, 2.6 and 2.3 ppm and from 2.0 to 0.8 ppm.

The $^1$H-NMR analysis of Camp1 is shown in FIG. 10. The shifts of the API resonances observed in the spectrum of Camp1 could suggest that proton transfer took place from the acidic counterion to the free base. The ratio API:CI turned out to be 1:1. At 2.1 ppm the signal of traces acetone was observed.

Figure 11:
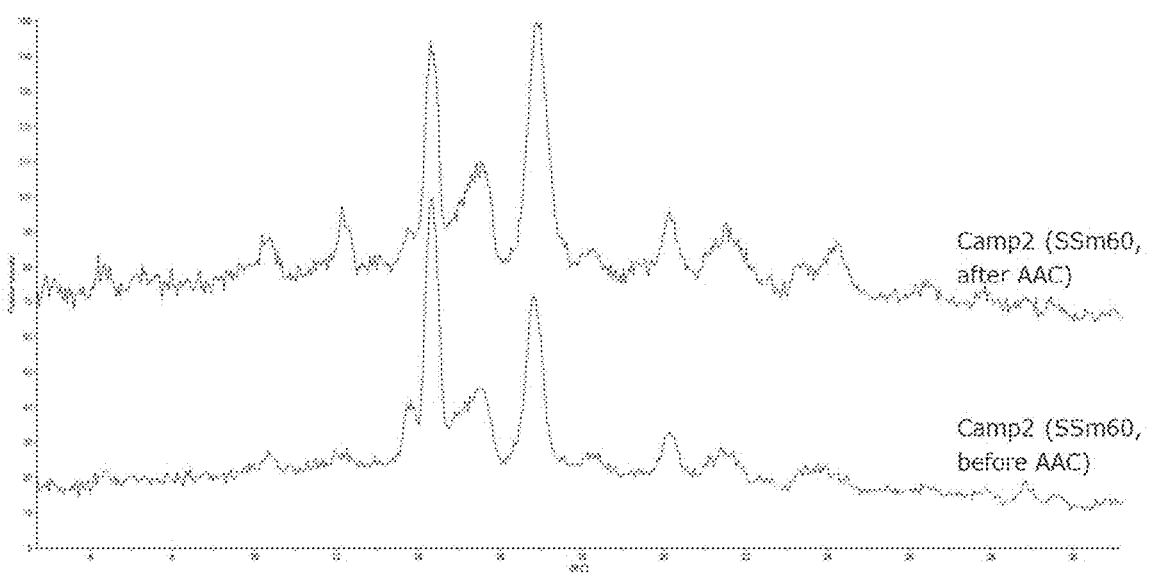
FIG. 11 shows HT-XRPD patterns of Exp. ID SSm60 before (bottom) (Camp2) and after (top) (Camp2) exposure to AAC (40° C./75% RH) for 2 days.

Camp2 was obtained from the salt formation experiment performed with camphor-10-sulfonic acid in ACN and an API:CI ratio of 1:1 (Exp. ID SSm60). Table 8 reports the experimental conditions producing Camp2. Camp2 was physically stable upon exposure to AAC (40° C./75% RH) for 2 days (FIG. 11).

TABLE 8

Experimental conditions producing Camp2.

| Exp. ID | API:CI Ratio 1:x | Solvent | Form | Form after AAC |
|---|---|---|---|---|
| SSm60 | 1 | ACN | Camp2 | Camp2 |

Figure 12:
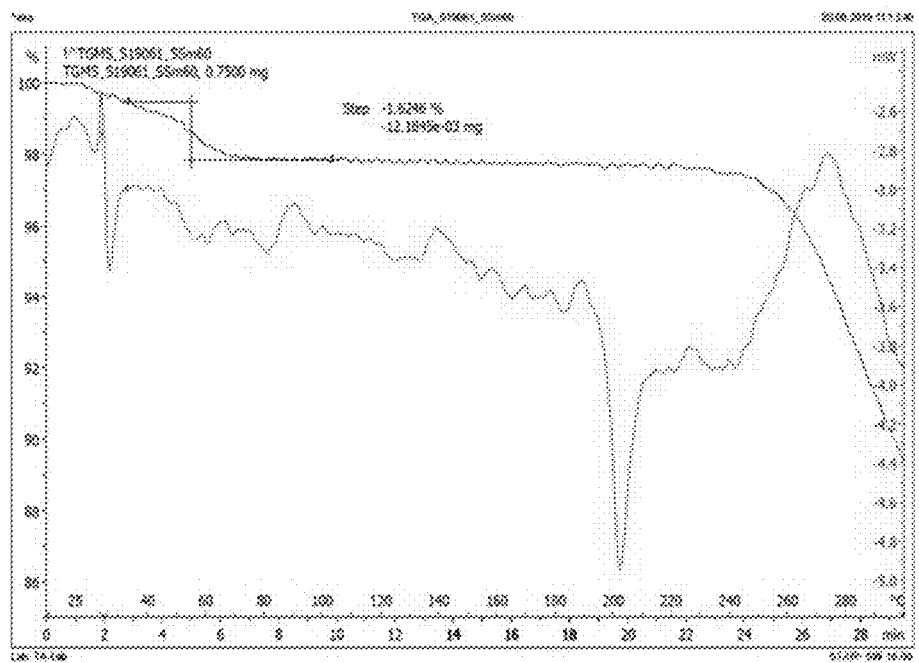
FIG. 12 shows TGA (A) and TGMS (B) analysis (heating rate of 10° C./min) of Camp2 (Exp. ID SSm60 (solids recovered after evaporation of the ML)). A mass loss of 1.6% attributed to water was observed between 25-80° C. Thermal decomposition of the salt was observed above 240° C. The heat flow signal of the TGA showed a sharp endotherm at 200° C. possibly attributed to the melting of the anhydrous salt form.
Figure 12:
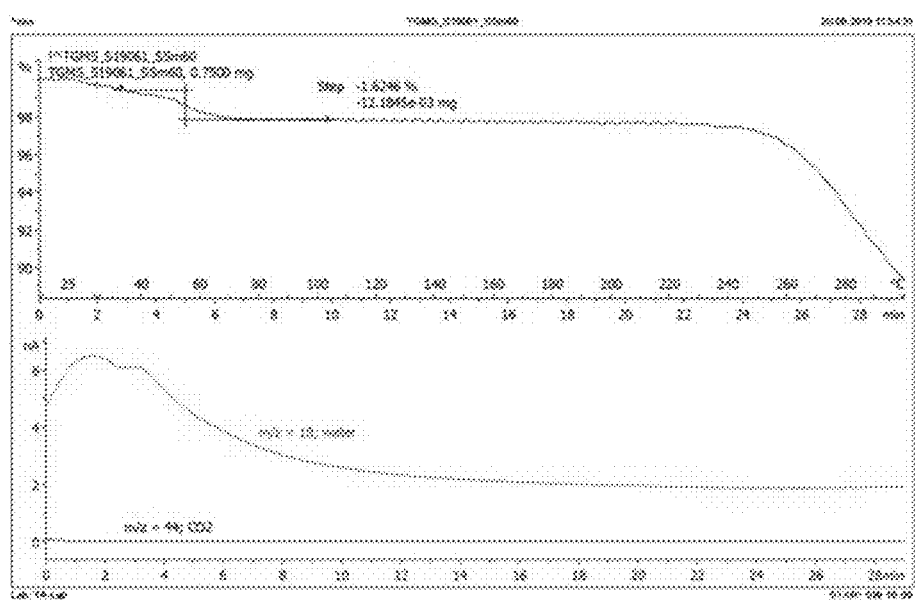

The TGA/TGMS analysis of Camp2 (FIG. 12) showed a mass loss of 1.6% from 25 to 100° C. attributed to water, based on the MS signal (1.6% corresponds to 0.7 molecules of water per salt molecule). The thermal decomposition is observed at temperatures above 240° C.

In the heat flow signal a sharp endothermic event was observed at around 200° C. attributed most likely to the melting of an anhydrous phase of the salt, followed by decomposition.

Figure 13:
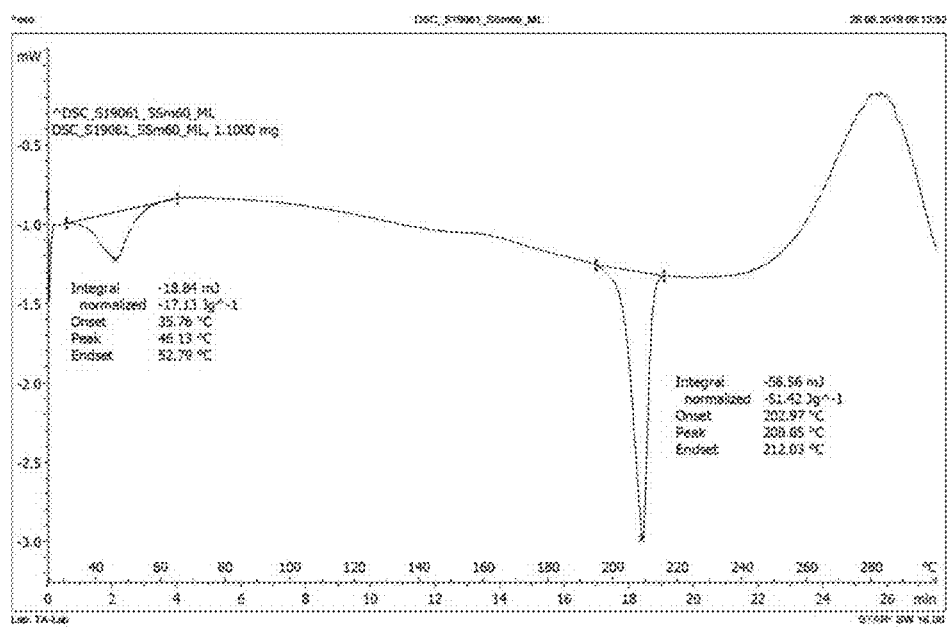
FIG. 13 shows DSC curve (heating rate 10° C./min) of Camp2 (Exp. ID SSm60 (solids recovered after evaporation of the ML)). The DSC curve showed a broad endothermic event from 25 to 70° C. associated to the water loss. An endothermic event at 208.9° C. could possibly be correlated to the melting of an anhydrous phase of the salt.

The DSC trace of Camp2 (FIG. 13) showed a broad endothermic event between 25 and 70° C., associated with the water loss. An endothermic event was recorded at 208.9° C. that could possibly be correlated to the melting of an anhydrous phase of the salt.

Figure 14:
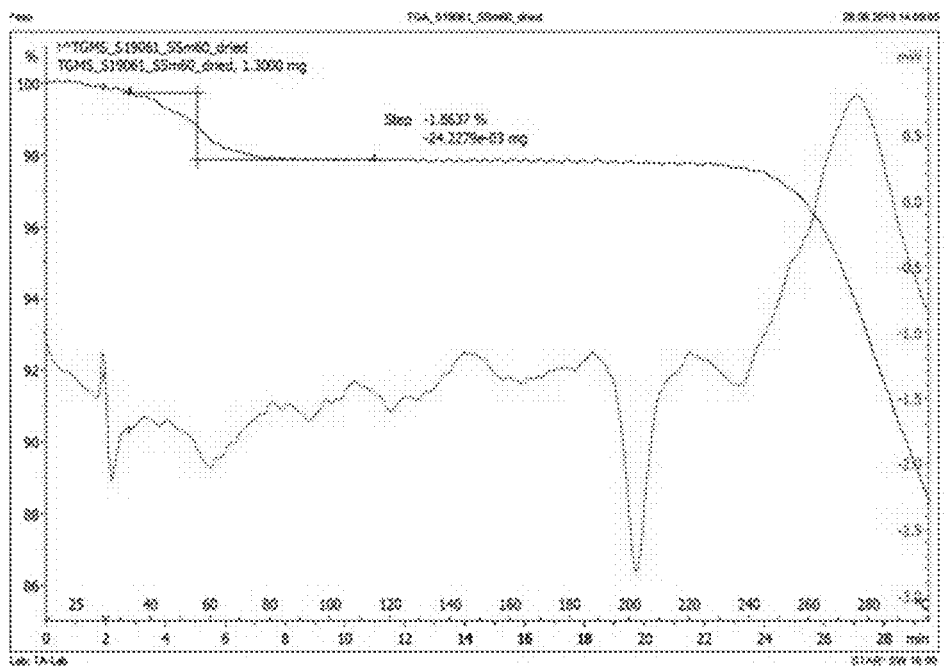
FIG. 14 shows TGA (A) and TGMS (B) analysis (heating rate of 10° C./min) of Camp2 (Exp. ID SSm60) after additional drying at 80° C. under vacuum for 1 hour. A mass loss of 1.9% attributed to water was observed between 25-70° C.
Figure 14:
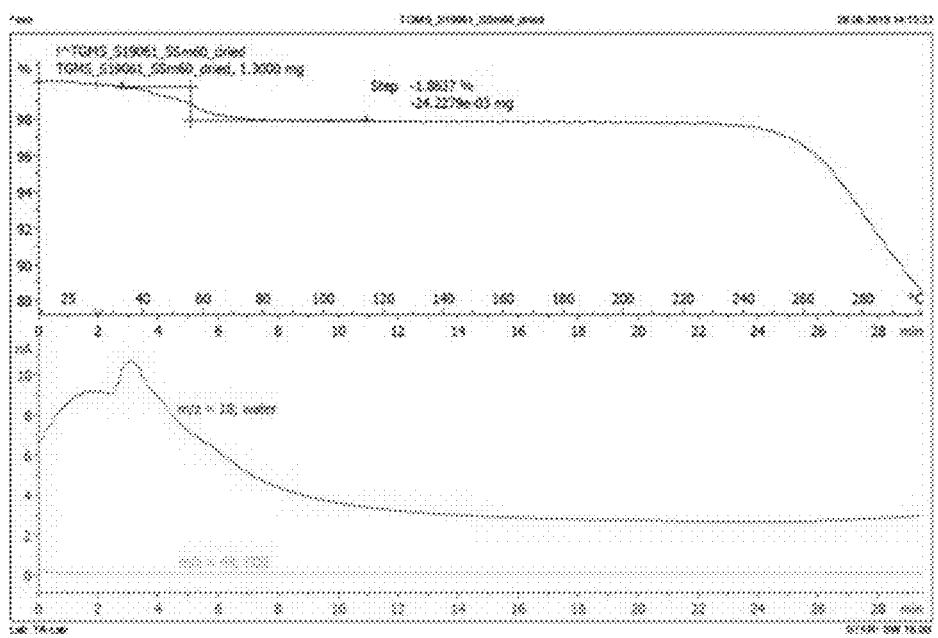

A sample of Camp2 (Exp. ID. SSm60) was dried at 80° C. under vacuum with the aim of isolating a potential anhydrous form melting at 208.9° C. observed in the DSC trace. The solid collected was analyzed by HT-XRPD and TGMS. The solid remained Camp2, containing 1.9% of water (FIG. 14).

Figure 15:
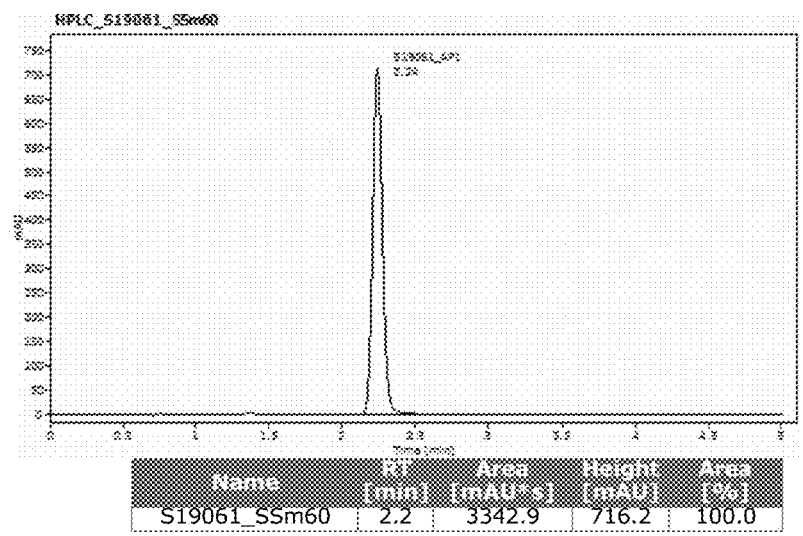
FIG. 15 shows LCMS chromatogram of Camp2 (Exp. ID SSm60 (solids recovered after evaporation of the ML). The API chemical purity was 100% (area %).

The chemical purity of Camp2 was assessed by LCMS to 100% (FIG. 15) confirming that the API was present in the solid phase Camp2.

Figure 16:
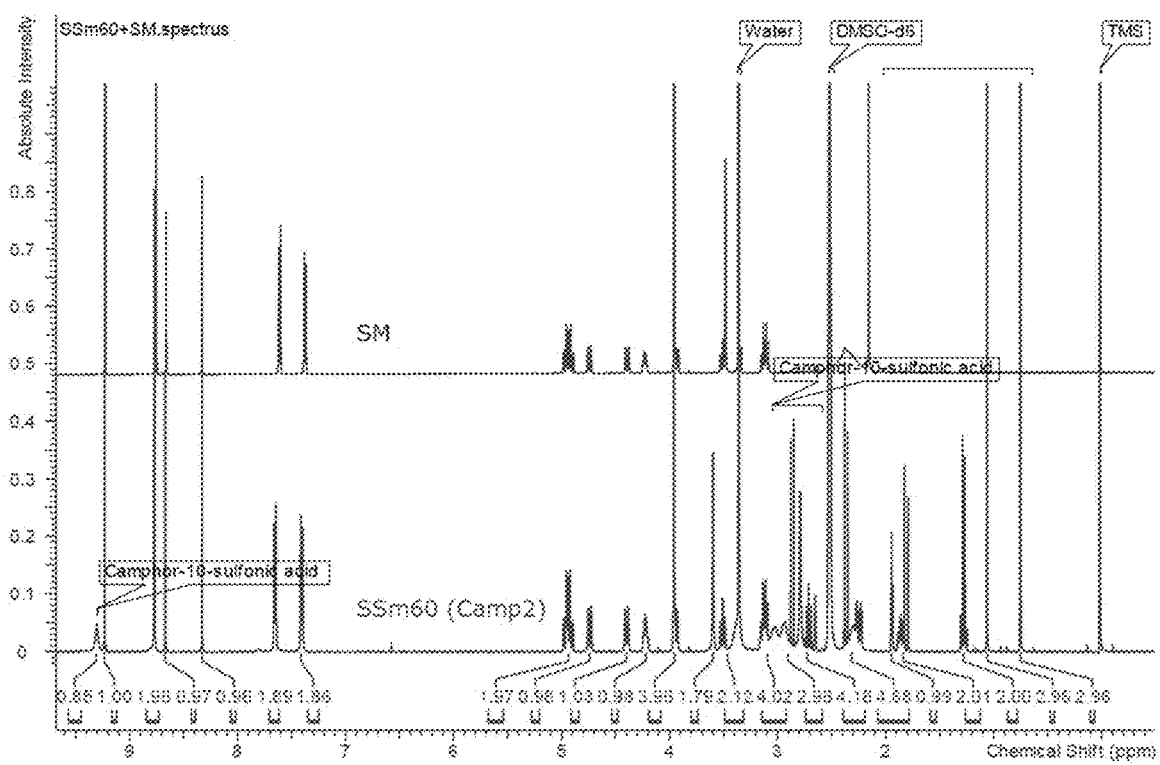
FIG. 16 shows Overlay of $^1$H-NMR spectra (500 MHz, DMSO-d6) of ABN-401 free base (green line) and Camp2 (Exp. ID SSm60, red line). The peaks corresponding to the CI were highlighted by the signal at 9.3, 3.0, 2.7, 2.6 and 2.3 ppm and from 2.0 to 0.8 ppm.

The $^1$H-NMR analysis of Camp2 is shown in FIG. 16. The shift of the API resonances observed in the spectrum of Camp2 could suggest that proton transfer took place from the acidic counterion to the free base. The ratio API:CI turned out to be 1:1.

Analytical Characterization of Camp2

Figure 17:
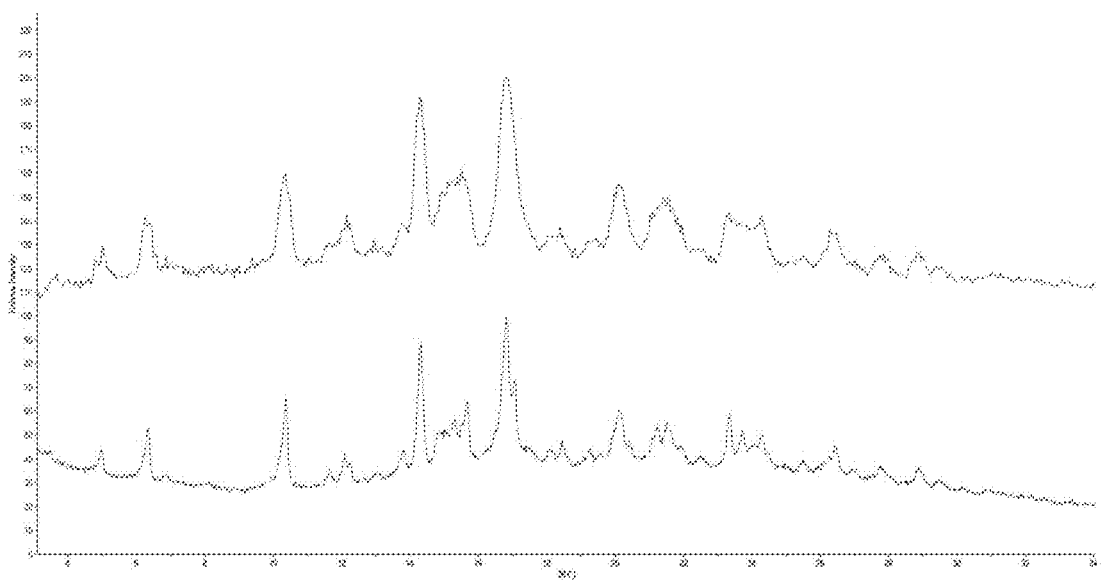
FIG. 17 shows HR-XRPD (bottom) and HT-XRPD (top) of Camp2 (Exp. ID. SSm73).

The HT- and HR-XRPD analysis confirmed the crystallization of Camp2 in the scale-up experiment (Exp. ID: SSm73) (FIG. 17). The High Resolution XRPD (HR-XRPD) data of Camp2 could not be indexed.

Figure 18:
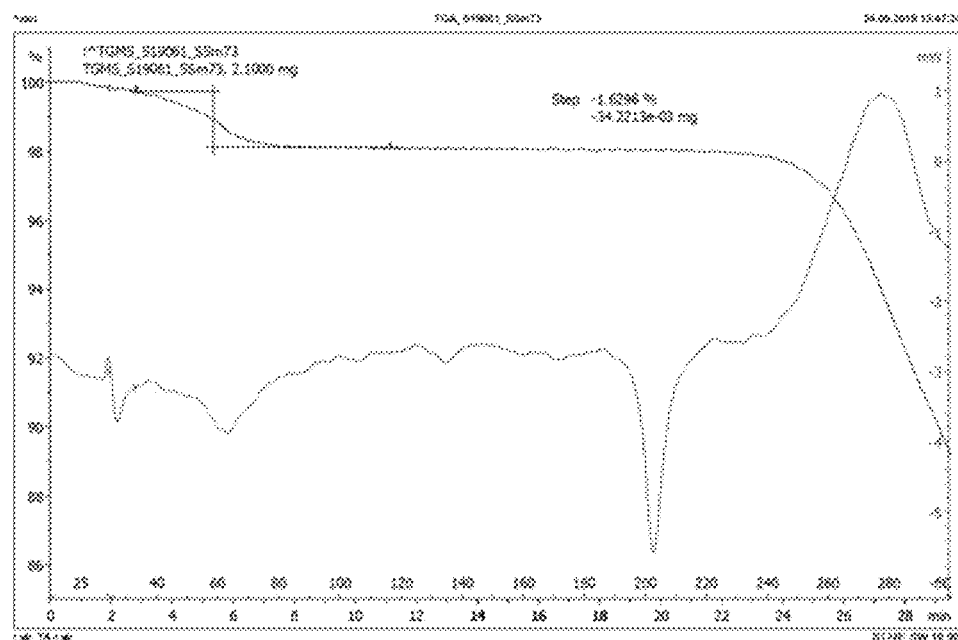
FIG. 18 shows TGA (A) and TGMS (B) analysis (heating rate of 10° C./min) of Camp2 (Exp. ID SSm73). A mass loss of 1.6% attributed to water was observed between 25-80° C. The thermal decomposition of the salt was observed around 240° C. The heat flow signal of the TGA showed an endotherm at 200° C. most likely attributed to the melting of an anhydrous phase of the salt.
Figure 18:
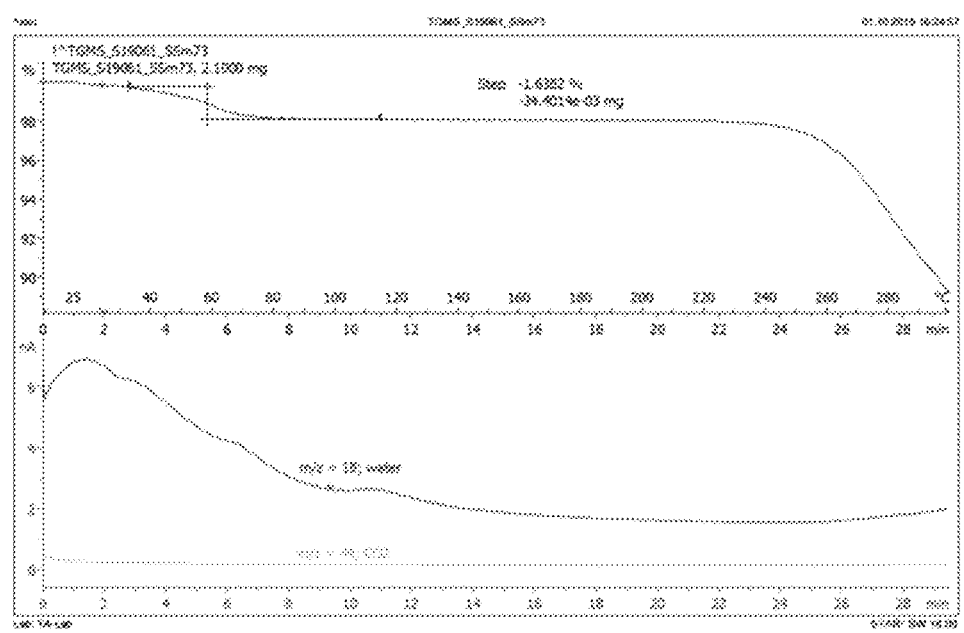

The TGA/TGMS analysis of dried Camp2 (FIG. 18) showed a pronounced mass loss of 1.6% between 25-80° C., attributed to water based on the MS signal (1.6% corresponds to 0.7 molecules of water per salt molecule). Thermal decomposition of Camp2 was observed above 240° C.

Figure 19:
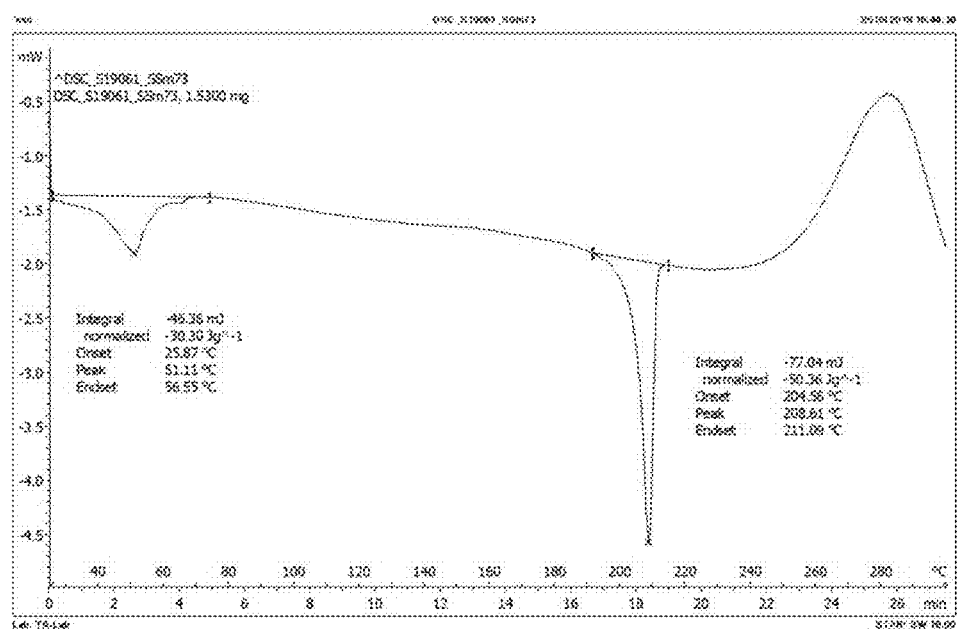
FIG. 19 shows DSC curve (heating rate 10° C./min) of Camp2 (Exp. ID: SSm73). The DSC curve showed one broad endothermic event, from 25 to 80° C., that can be related to the water loss. A second sharp endotherm was observed at 208.6° C. that could be associated to the melting of an anhydrous phase of the salt.

The DSC trace of Camp2 (FIG. 19) showed one broad endothermic event, between 25 and 80° C., associated with the water loss. A second sharp endothermic event was observed at 208.6° C. most likely related to the melting of an anhydrous phase of the salt.

Figure 20:
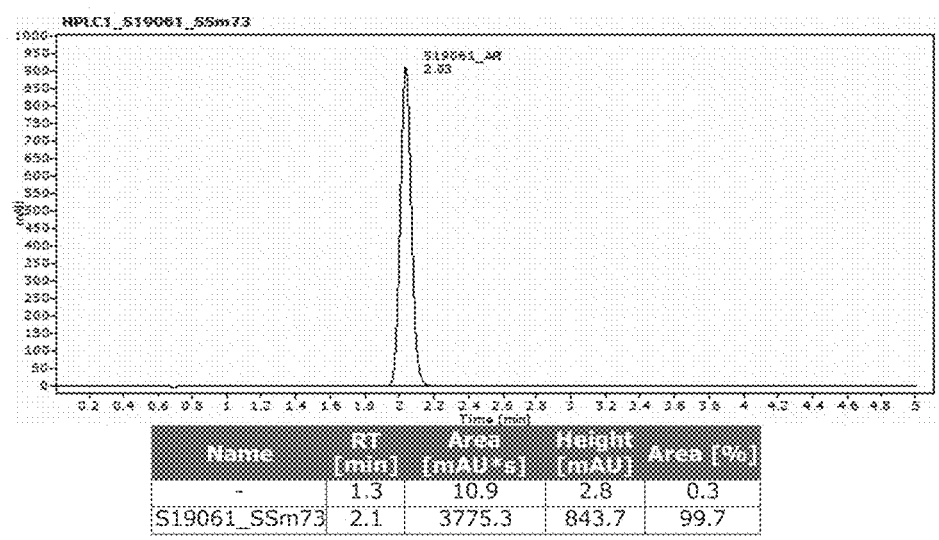
FIG. 20 shows LCMS chromatogram of Camp2 (Exp. ID SSm73). The API chemical purity was 99.7% (area %).

The chemical purity of Camp2 was assessed by LCMS to 99.7% (FIG. 20) confirming that the API was present in the solid phase Camp2.

Figure 21:
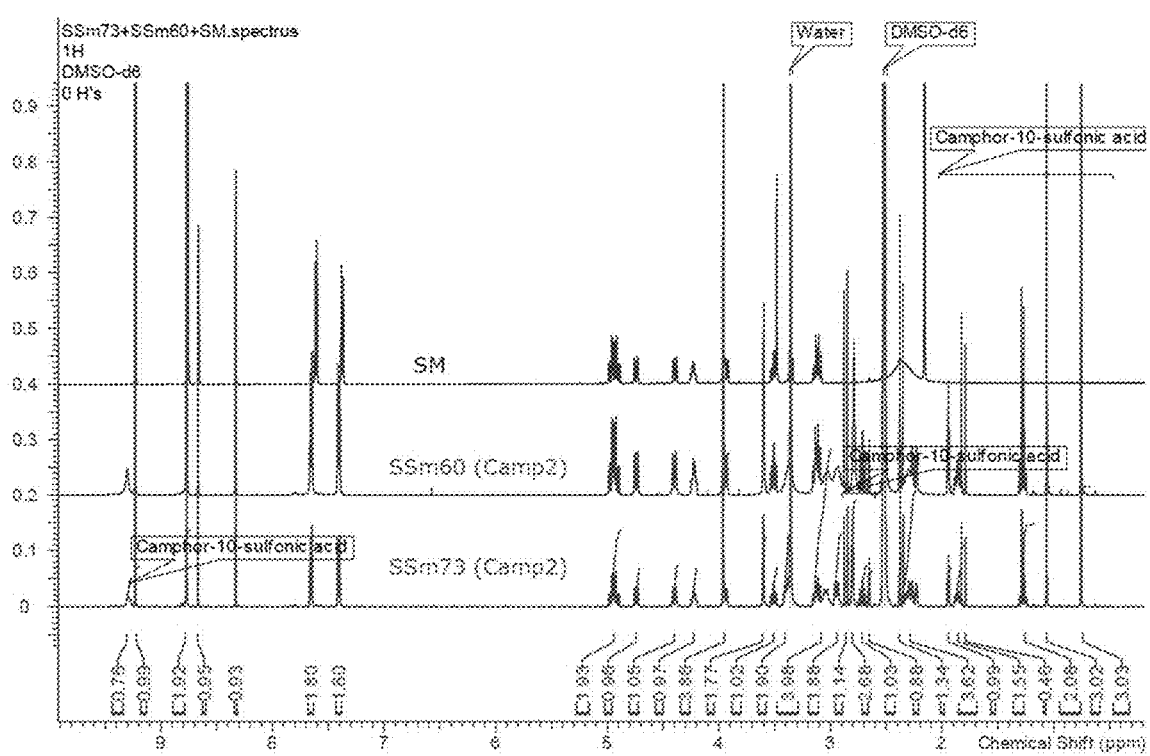
FIG. 21 shows Overlay of $^1$H-NMR spectra (500 MHz, DMSO-d6) of ABN-401 free base (blue line), Camp2 (Exp. ID SSm60, green line) and Camp2 (Exp. ID SSm73, red line). The peaks corresponding to the CI were highlighted by the signal at 9.3, 3.0, 2.7, 2.6 and 2.3 ppm and from 2.0 to 0.8 ppm.

The $^1$H-NMR analysis of Camp2 is shown in FIG. 21. The shift of the API resonances observed in the spectrum of Camp2 could suggest that proton transfer took place from the acidic counterion to the free base. The ratio API:CI was confirmed to be 1:1.

Figure 22:
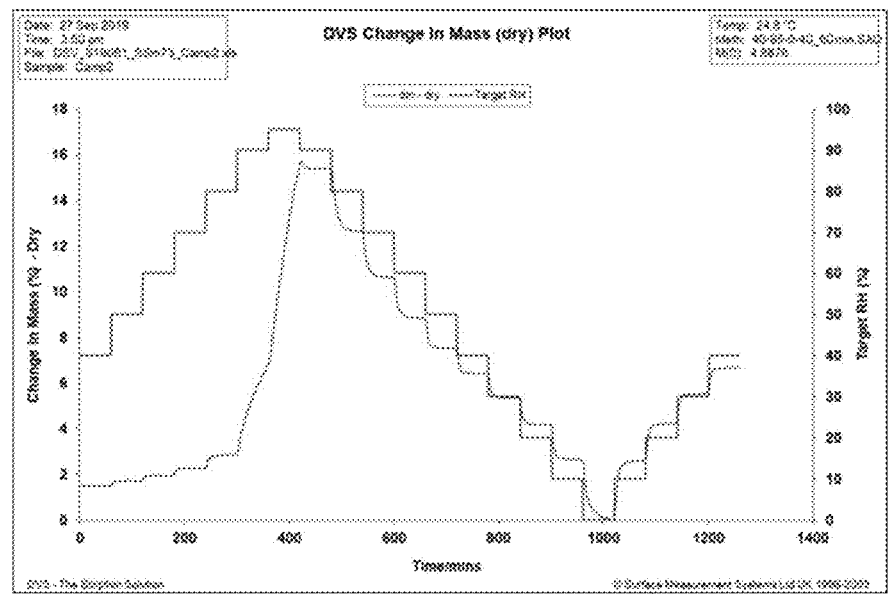
FIG. 22 shows Change in mass (A) and isotherm (B) resulting from the DVS measurement performed on Camp2 (Exp. ID SSm73).
Figure 22:
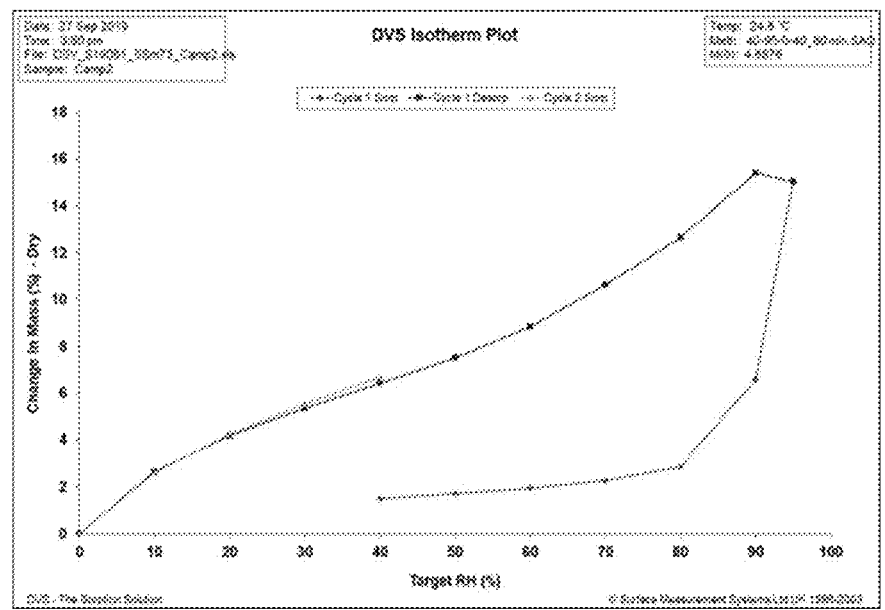
Figure 23:
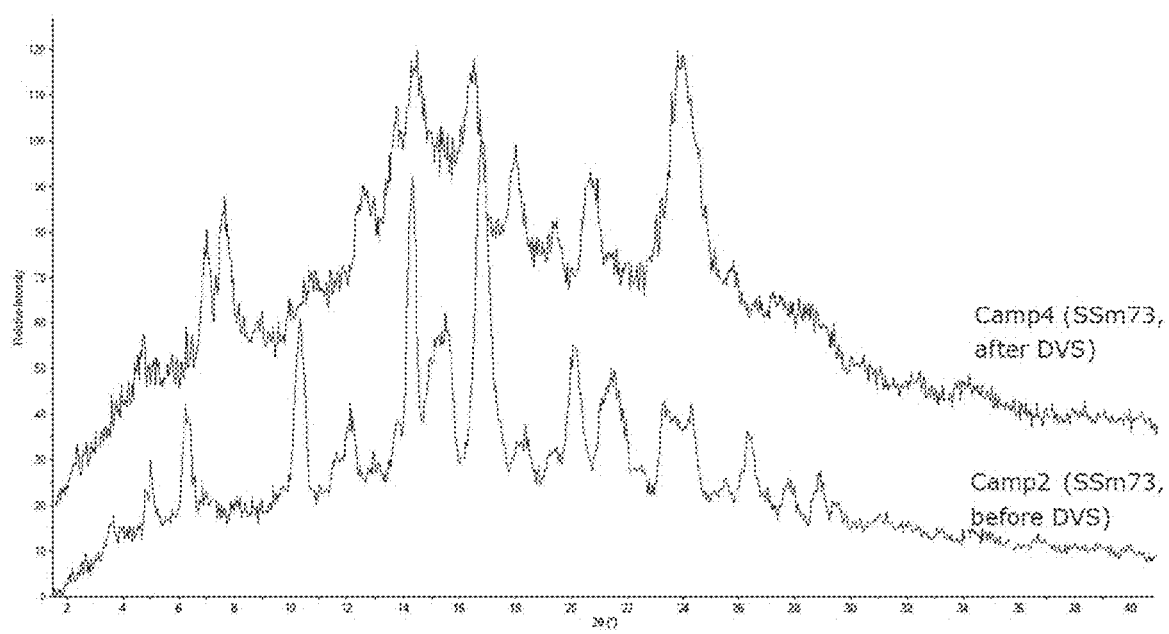
FIG. 23 shows HT-XRPD patterns of the camsylate salt (Exp. ID SSm73) before (Camp2, bottom) and after (Camp4, top) DVS analysis.
Figure 24:
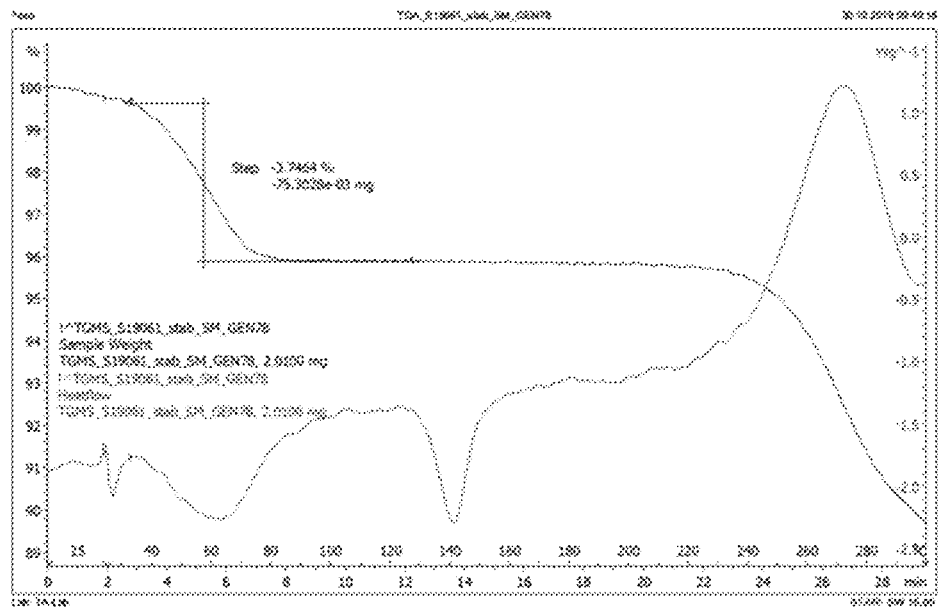
FIG. 24 shows TGMS analyses (heating rate of 10° C./min) of (A) Form A upon exposure to 25° C./60% RH for 1 month (Exp. ID GEN78) and (B) Form A upon exposure to 40° C./75% RH for 1 month (Exp. ID GEN74). A mass loss of 3.7 and 4.0% attributed to water was observed before the thermal decomposition (observed around 230° C.), respectively.
Figure 24:
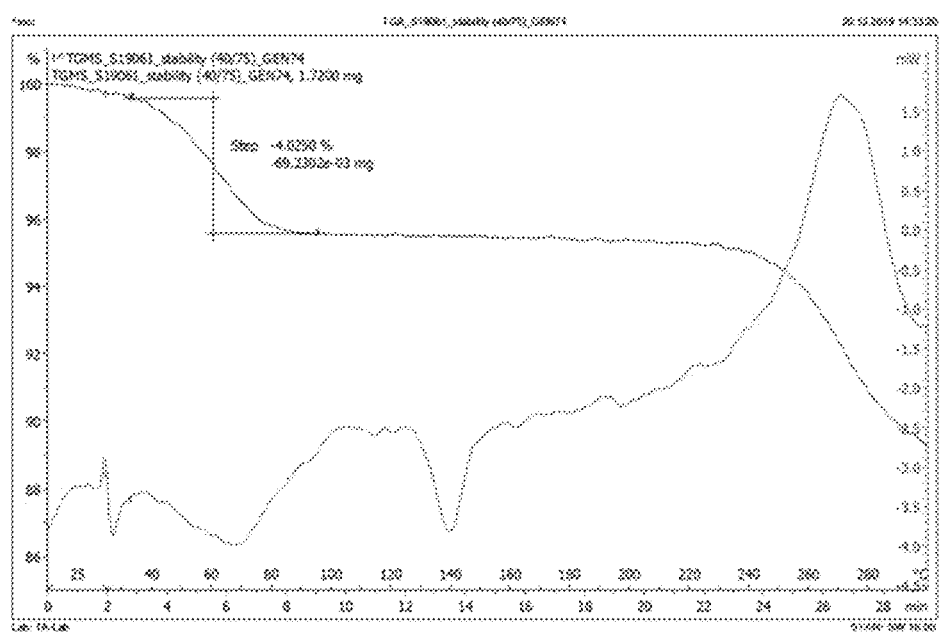

FIG. 22 reports the results of the DVS measurement performed on Camp2. In the first sorption half-cycle the water vapor uptake reached 15.6% at 95% RH (14.1% change in mass in the range 40-95% RH). The change in mass plot (left figure) showed that the water sorption had not reached equilibrium during sorption at 90-95% RH. During the desorption cycle, from 95 to 0% RH, water was released. In the last sorption half-cycle, the change in mass was 6.6% (in the range 0-40% RH). The water uptake was irreversible, suggesting a form change occurred. A new form, designated as Camp4, was identified by HT-XRPD in the recovered solid (FIG. 23).

The DVS analysis showed a change in mass at 80% RH of 1.4% suggesting that this material is slightly hygroscopic (based on the European Pharmacopeia Hygroscopicity classification).

Stability of Free Base

Figure 25:
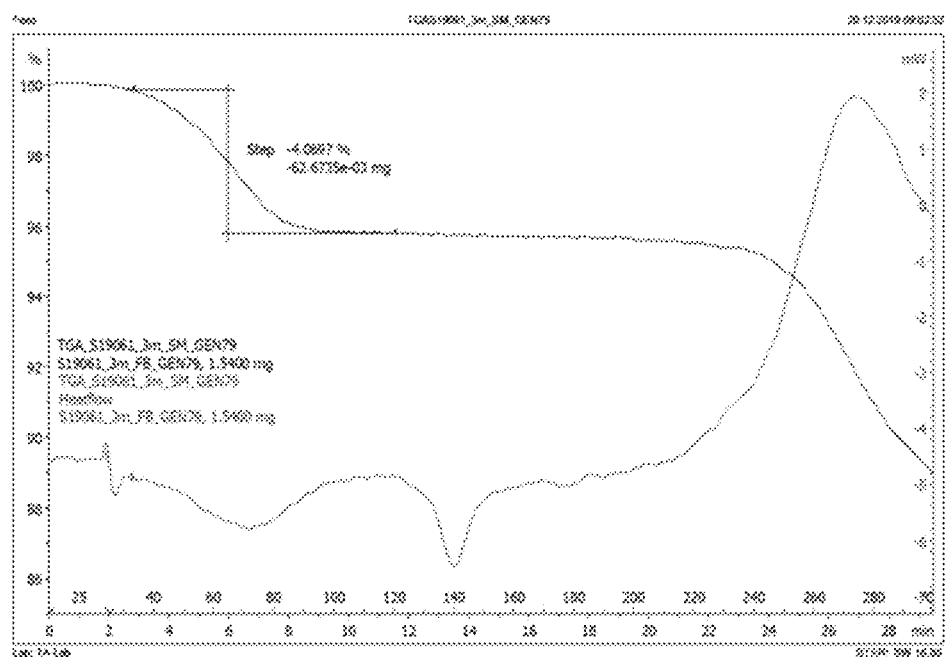
FIG. 25 shows TGMS analyses (heating rate of 10° C./min) of (A) Form A upon exposure to 25° C./60% RH for 3 months (Exp. ID GEN79) and (B) Form A upon exposure to 40° C./75% RH for 3 months (Exp. ID GEN75). A mass loss of 4.1 and 4.4% attributed to water was observed before the thermal decomposition (observed).
Figure 25:
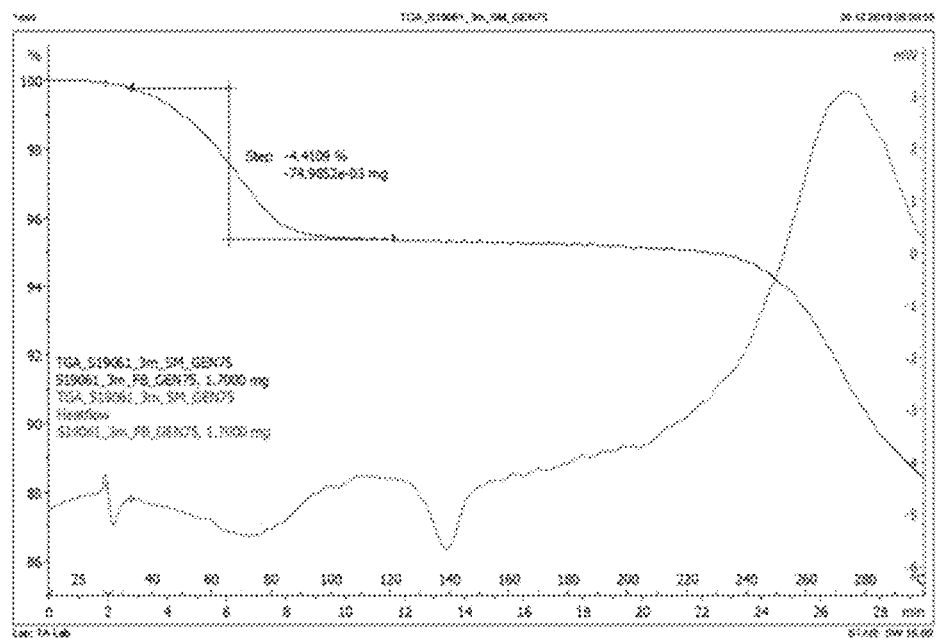

The TGA traces of the 3-months samples of Form A exposed to 25° C./60% RH and to 40° C./75% RH are shown in FIG. 25A, B. Water loss of 4.1% and 4.4% was observed, respectively, for the samples exposed to 25° C./60% RH and 40° C./75% RH for 3 months. The heat flow signals showed broad endotherm attributed to the water loss followed by a melting event at 140° C. corresponding to the melting of Form A. The thermal decomposition for both samples was observed above 230° C.

Figure 26:
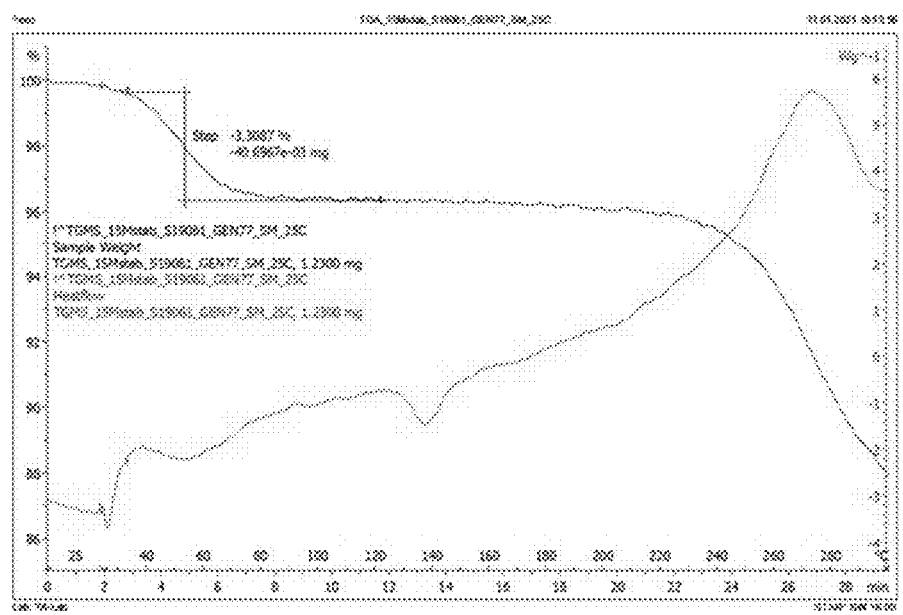
FIG. 26 shows TGMS analyses (heating rate of 10° C./min) of (A) Form A upon exposure to 25° C./60% RH for 15 months (Exp. ID GEN80) and (B) Form A upon exposure to 40° C./75% RH for 15 months (Exp. ID GEN77). A mass loss of 3.3 and 3.7% attributed to water was observed before the thermal decomposition (observed around 230° C.), respectively.
Figure 26:
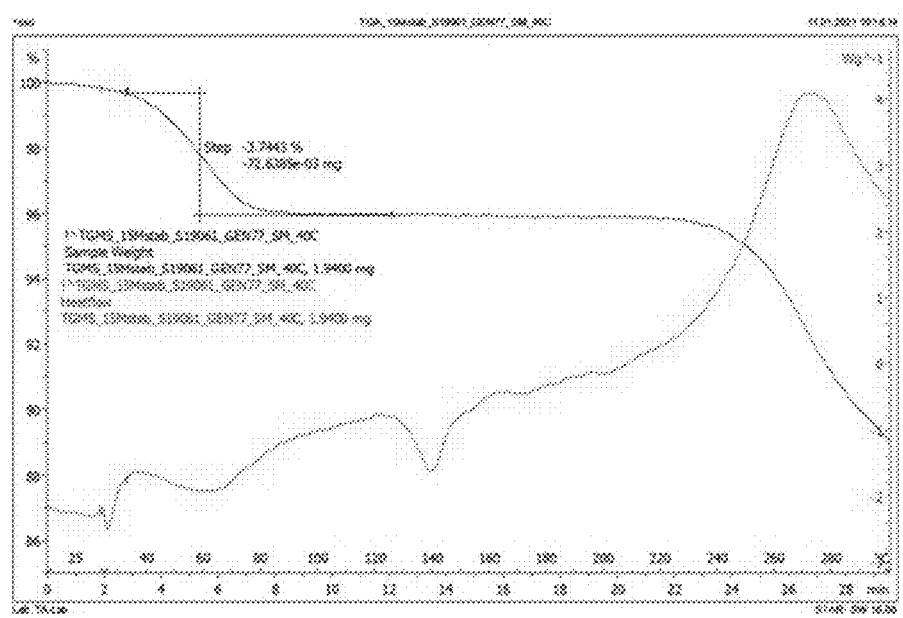

The TGA traces of the 15-months samples of Form A exposed to 25° C./60% RH and to 40° C./75% RH are shown in FIG. 26A, B. Water loss of 3.3% and 3.7% was observed, respectively, for the samples exposed to 25° C./60% RH and 40° C./75% RH for 15 months. The heat flow signals showed broad endotherm attributed to the water loss followed by a melting event at 140° C. corresponding to the melting of Form A. The thermal decomposition for both samples was observed above 230° C.

Figure 27:
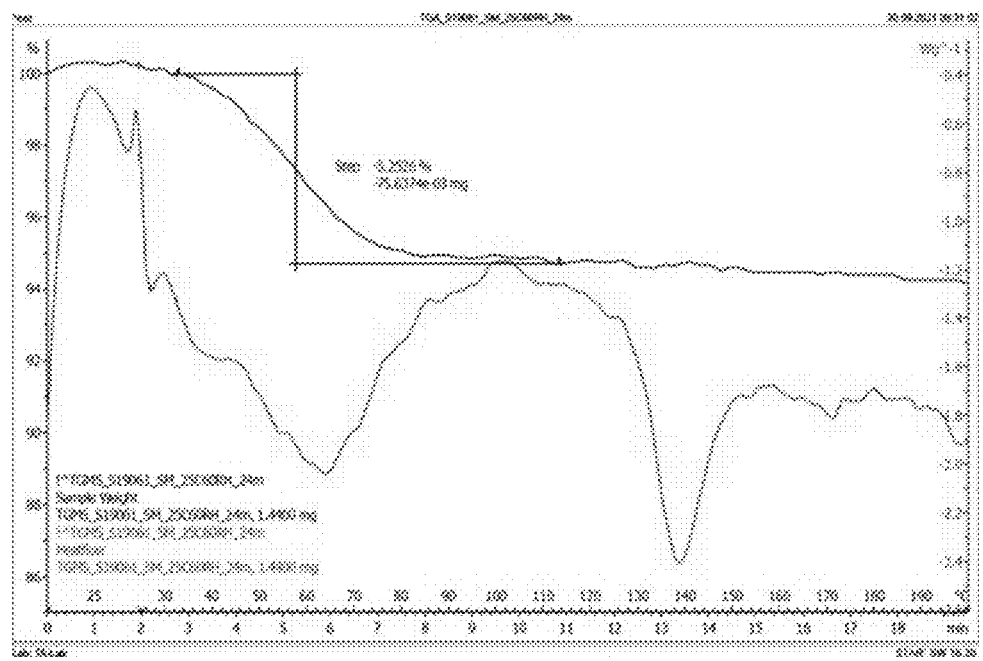
FIG. 27 shows TGMS analyses (heating rate of 10° C./min) of (A) Form A upon exposure to 25° C./60% RH for 24 months (Exp. ID GEN81) and (B) Form A upon exposure to 40° C./75% RH for 24 months (Exp. ID GEN76). A mass loss of 5.3 and 5.2% attributed to water was observed before the thermal decomposition, respectively.
Figure 27:
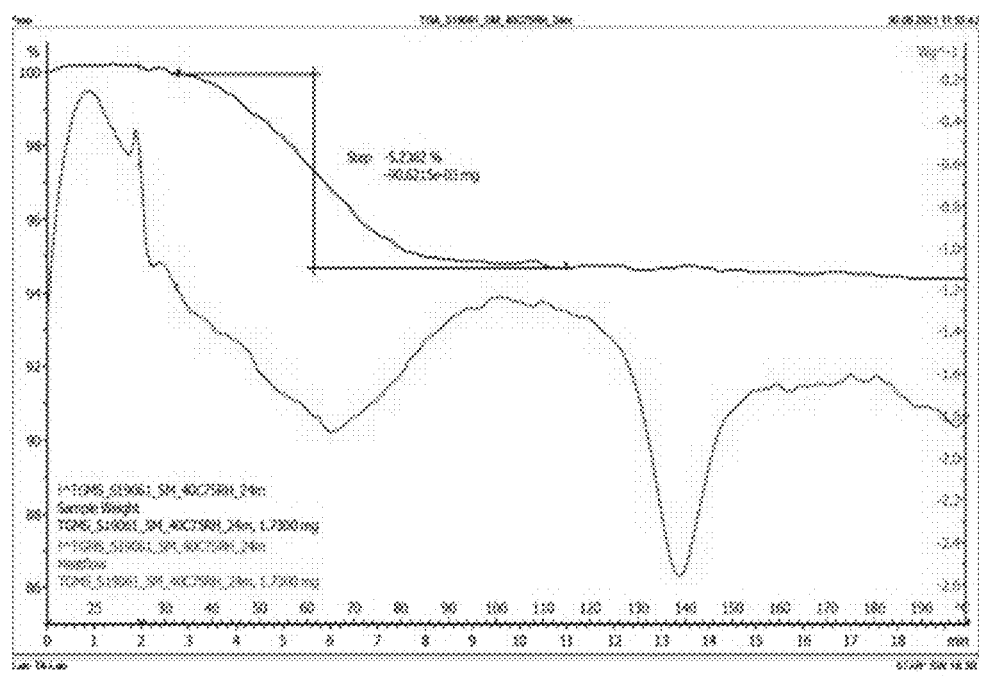

The TGA traces of the 24-months samples of Form A exposed to 25° C./60% RH and to 40° C./75% RH are shown in FIG. 27A, B. Water loss of 5.3% and 5.2% was observed, respectively, for the samples exposed to 25° C./60% RH and 40° C./75% RH for 24 months. The heat flow signals showed broad endotherm attributed to the water loss followed by a melting event at 140° C. corresponding to the melting of Form A. No thermal decomposition was observed below 200° C.

Figure 28:
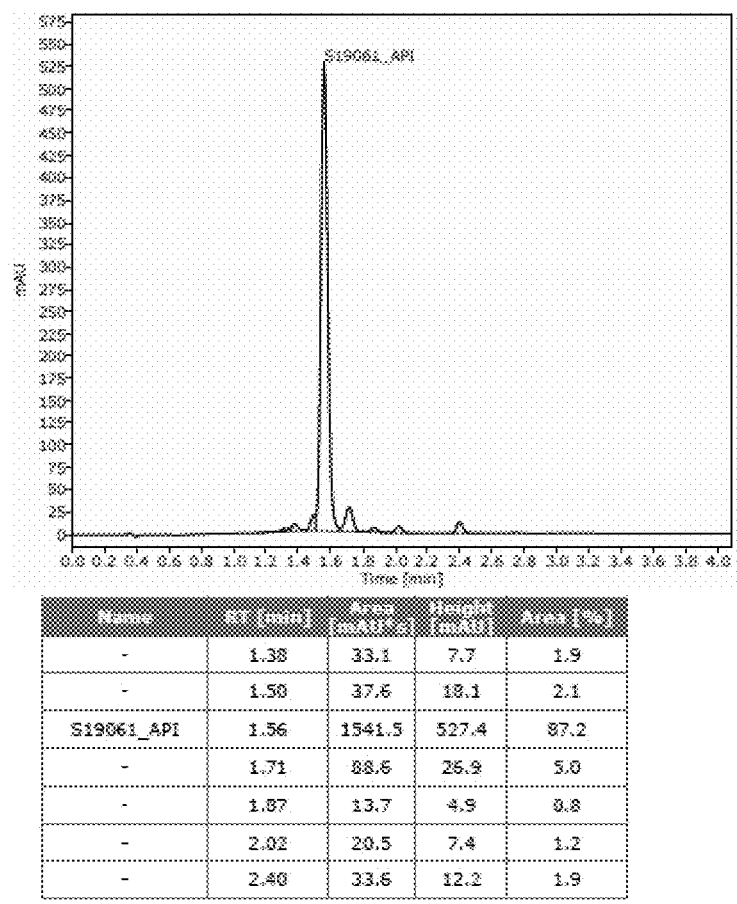
FIG. 28 shows HPLC chromatogram of Form A upon exposure to 25° C./60% RH for 24 months (Exp. ID GEN81). The API chemical purity was 87.2% (area %).
Figure 29:
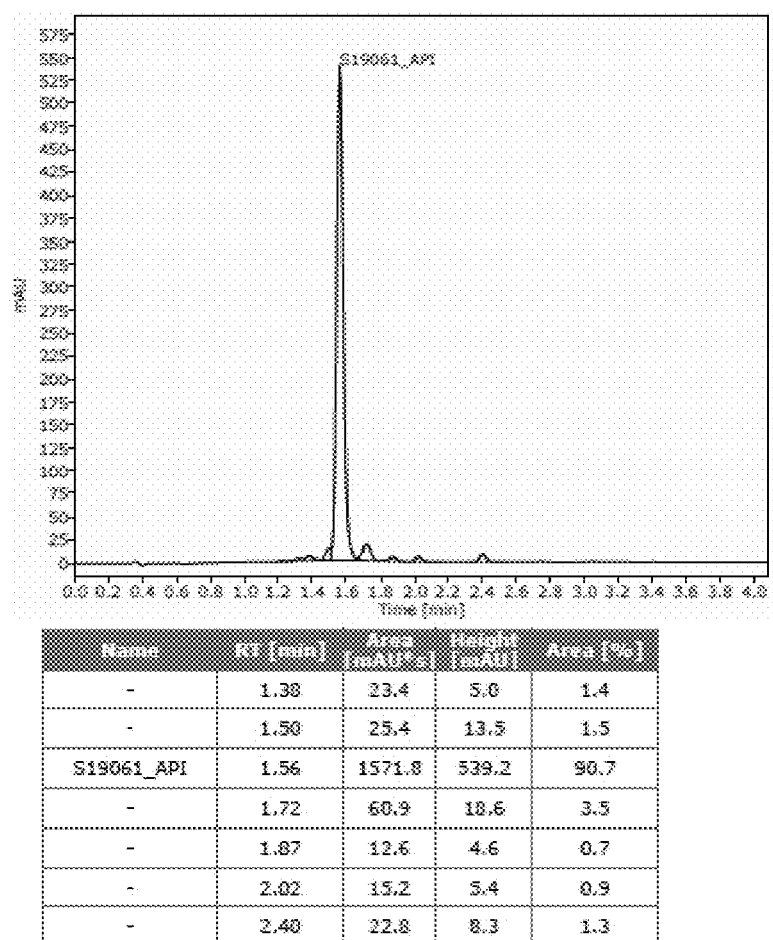
FIG. 29 shows HPLC chromatogram of Form A upon exposure to 40° C./75% RH for 24 months (Exp. ID GEN76). The API chemical purity was 90.7% (area %).

The chemical purity of Form A after 24 months exposure to 25° C./60% RH (Exp. ID GEN81) and to 40° C./75% RH (Exp. ID GEN76) assessed by LCMS was 87.2% and 90.7%, respectively (FIG. 28 and FIG. 29), confirming that chemical degradation is occurring at both conditions.

Stability of Camsylate Salt

Figure 30:
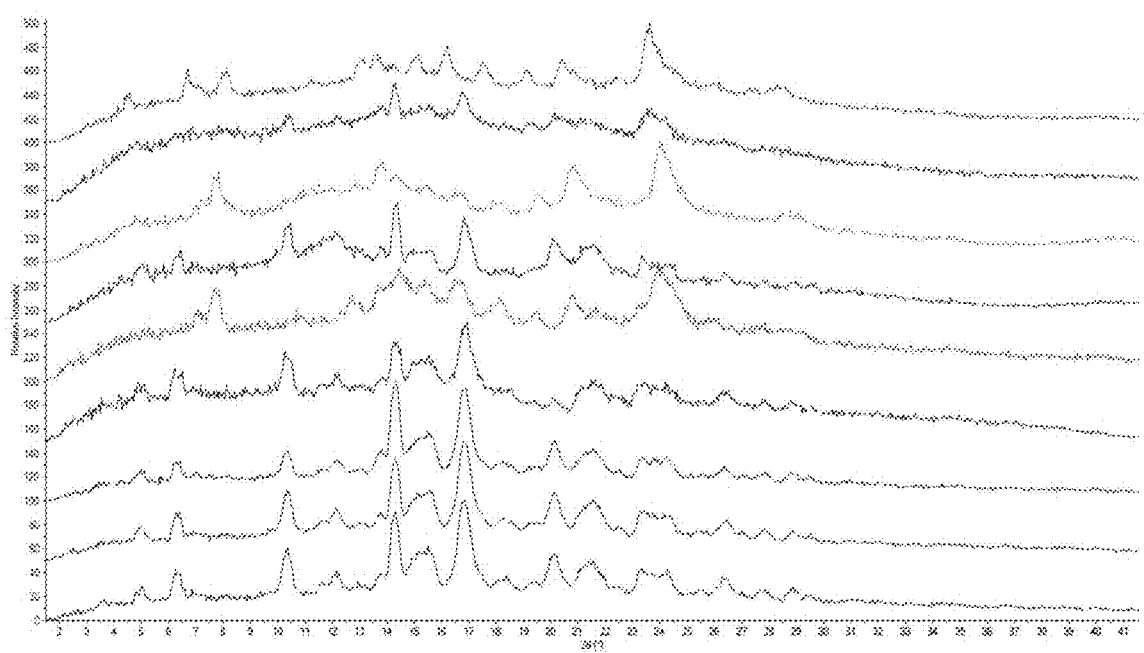
FIG. 30 shows Overlay of HT-XRPD patterns (from bottom to top) of scale-up Camp2 (Exp. ID. SSm73), Camp2 upon exposure to 25° C./60% RH for 1 month (Exp. ID GEN50), Camp2 upon exposure to 40° C./75% RH for 1 month (Exp. ID GEN54), Camp2 upon exposure to 25° C./60% RH for 3 months (Exp. ID GEN51) and Camp4 upon exposure to 40° C./75% RH for 3 months (Exp. ID GEN55), Camp2 upon exposure to 25° C./60% RH for 15 months (Exp. ID GEN52) and Camp4 upon exposure to 40° C./75% RH for 15 months (Exp. ID GEN56), Camp2 upon exposure to 25° C./60% RH for 24 months (Exp. ID GEN53) and Camp3+E upon exposure to 40° C./75% RH for 24 months (Exp. ID GEN57).

The HT-XRPD analysis confirmed that no solid form conversion occurred upon exposure of Camp2 to 25° C./60% RH up to 24 months. However, at 40° C./75% RH, solid form conversions were observed after 3 months. The new powder pattern could be assigned to the powder pattern of Camp4 (identified previously after a DVS analysis performed on Camp2, FIG. 23). After 24 months further conversions were observed possibly to a mixture of a camsylate salt and Form E of the free base. In FIG. 30, an overlay of the powder patterns of Camp2 obtained in the scale-up and after exposure to 25° C./60% RH and 40° C./75% RH for 1, 3, 15 and 24 months is presented.

Figure 31:
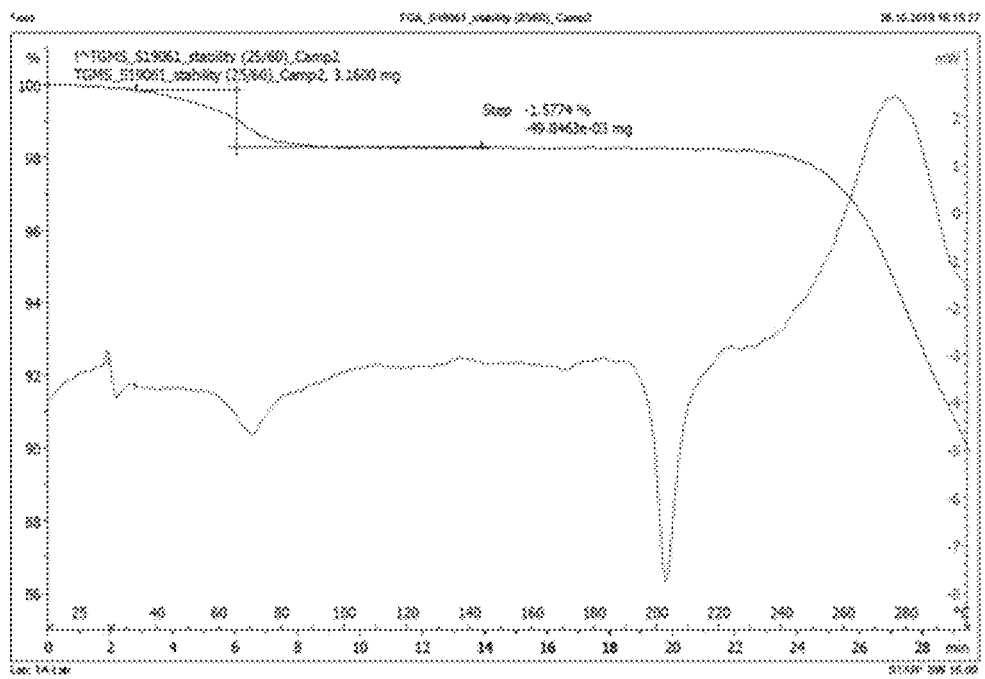
FIG. 31 shows TGA analyses (heating rate of 10° C./min) of (A) Camp2 upon exposure to 25° C./60% RH for 1 month (Exp. ID GEN50) and (B) Camp2 upon exposure to 40° C./75% RH for 1 month (Exp. ID GEN54). A mass loss of 1.6 and 1.8% attributed to water was observed before the thermal decomposition of the salt (observed around 240° C.).
Figure 31:
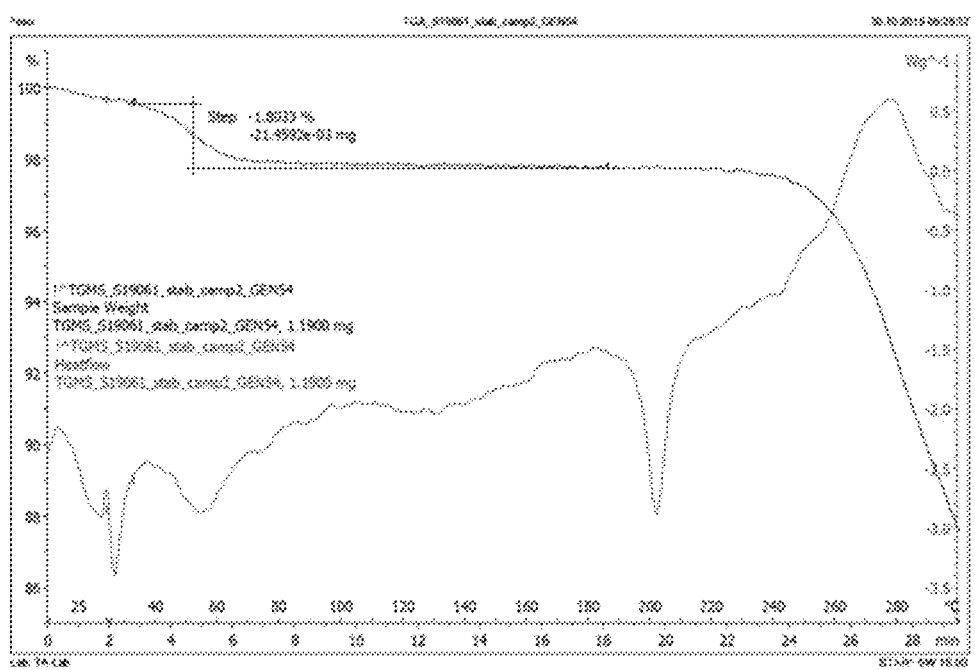

The TGA analyses of the solids of Camp2 exposed to 25° C./60% RH and 40° C./75% RH for 1 month are shown in FIG. 31A B. A water loss of 1.6% was observed for the sample exposed to 25° C./60% RH for 1 month and 1.8% for the sample exposed to 40° C./75% RH for 1 month. Thermal decomposition for both samples was observed above 240° C.

Figure 32:
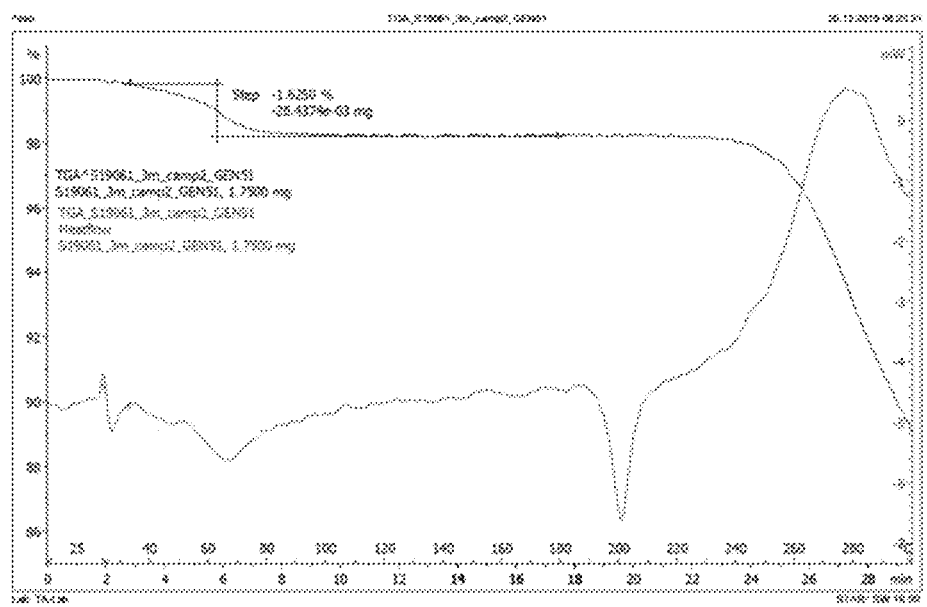
FIG. 32 shows TGA analyses (heating rate of 10° C./min) of (A) Camp2 upon exposure to 25° C./60% RH for 3 months (Exp. ID GEN51) and (B) Camp2 upon exposure to 40° C./75% RH for 3 months (Exp. ID GEN55). A mass loss of 1.6 and 7.1% attributed to water was observed before the thermal decomposition (observed around 240° C.), respectively. The heat flow signals showed broad endotherms corresponding to the released of water followed by endothermic events at 200° C., in case of GEN51 and at 150° C. for GEN55.
Figure 32:
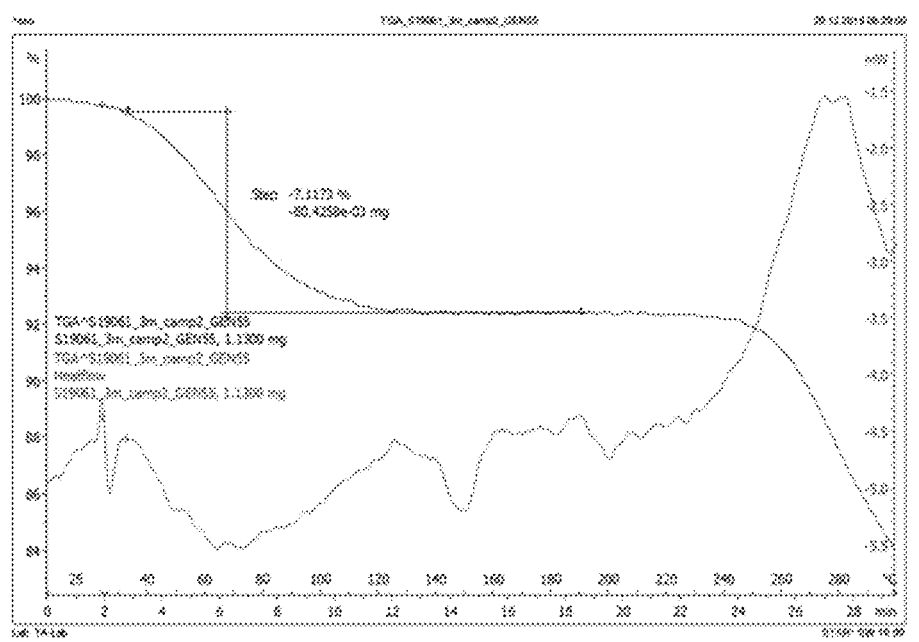
Figure 33:
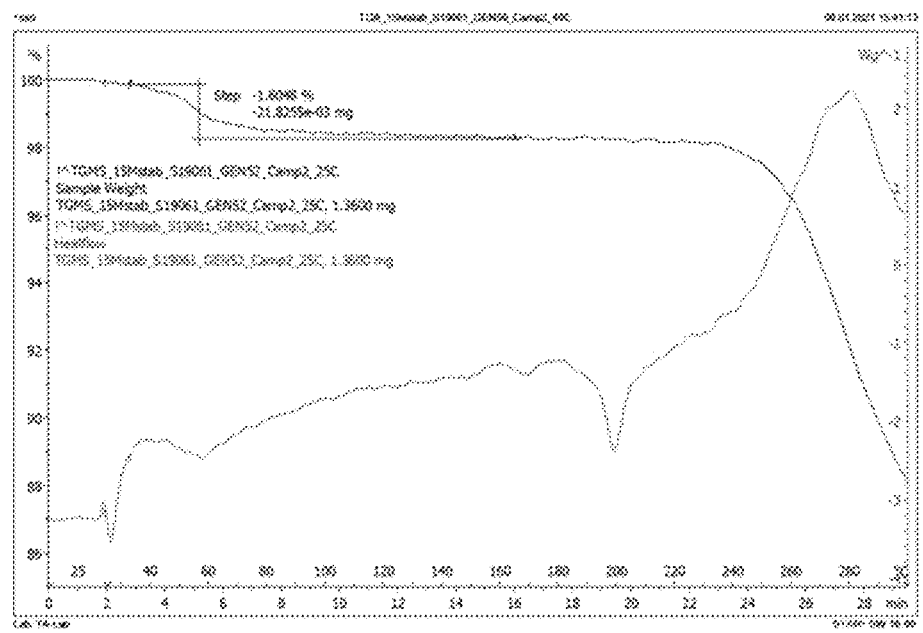
FIG. 33 shows TGA analyses (heating rate of 10° C./min) of (A) Camp2 upon exposure to 25° C./60% RH for 15 months (Exp. ID GEN52) and (B) Camp2 upon exposure to 40° C./75% RH for 15 months (Exp. ID GEN56). A mass loss of 1.6 and 6.9% attributed to water was observed before the thermal decomposition (observed around 240° C.), respectively. The heat flow signals showed broad endotherms corresponding to the released of water followed by endothermic events at 200° C., in case of GEN52 and at 150° C. for GEN56.
Figure 33:
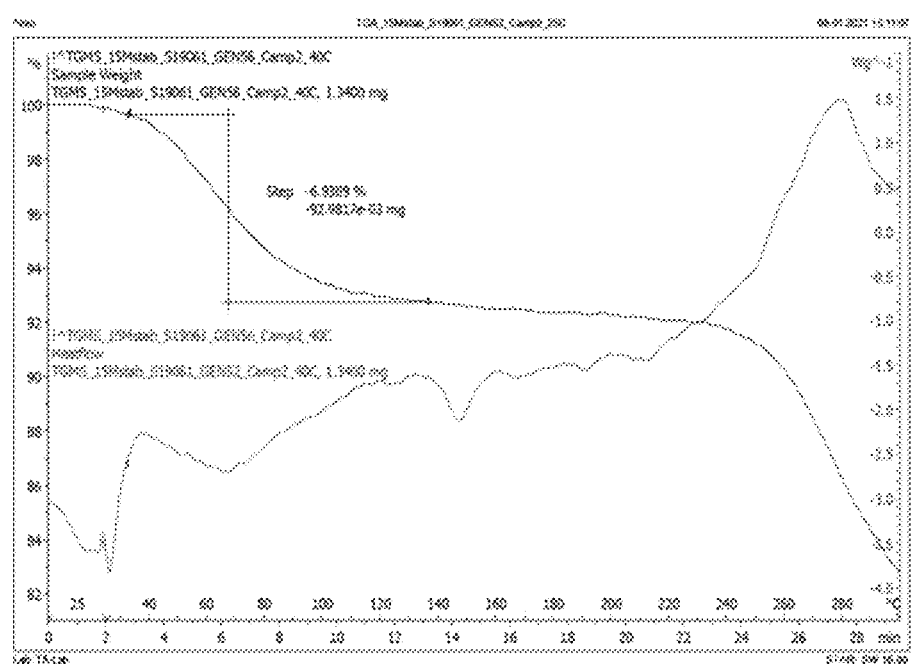

The sample of Camp2 incubated at 25° C./60% RH for 3 months showed a similar water content to that recorded after 1-month (FIG. 32A), meaning that no significant water uptake occurred at this condition. However, at 40° C./75% RH, solid form conversion of Camp2 to Camp4 was observed; therefore, the TGA analysis (FIG. 32B) showed a water content of 7.1% (3.3 molecules of water per molecule of camsylate salt). The thermal behavior recorded in the heat flow signal showed a broad endotherm attributed to the water released followed by the melting at 150° C. which could be attributed to the melting of an anhydrous phase (different to Camp2, melting at 200° C.).

The sample of Camp2 incubated at 25° C./60% RH for 15 months showed a similar water content to that recorded after 1 and 3 months (FIG. 160A), meaning that no significant water uptake occurred at this condition. At 40° C./75% RH, Camp4 remained Camp4 up to 15 months. Also the water content remained similar to the water content observed after 3 months, the TGA analysis (FIG. 160B) showed a water content of 6.9% (3.3 molecules of water per molecule of camsylate salt). The thermal behavior recorded in the heat flow signal showed a broad endotherm attributed to the water released followed by an endotherm at 150° C. which could be attributed to the melting of an anhydrous phase (different to Camp2, melting at 200° C.).

Figure 34:
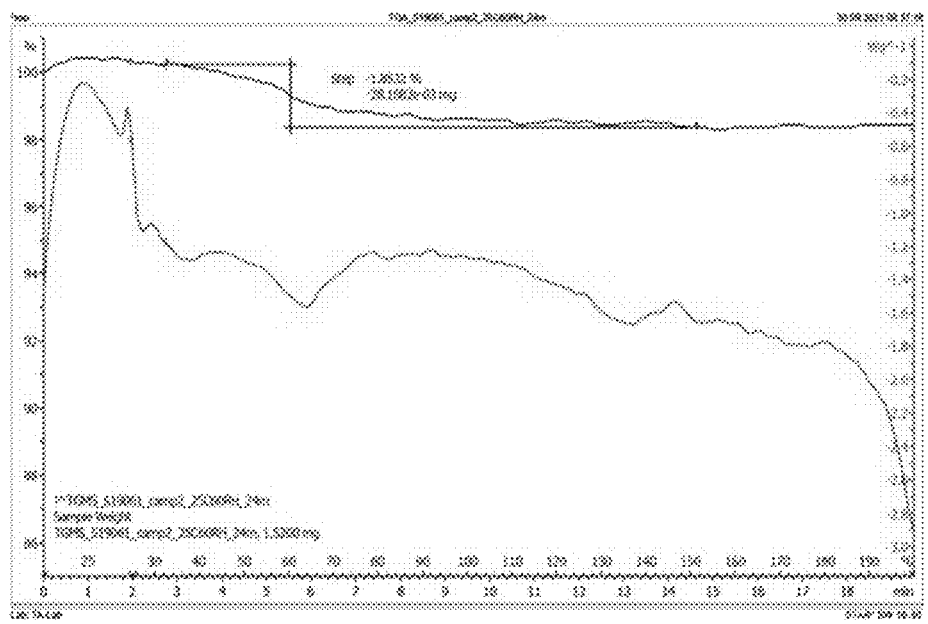
FIG. 34 shows TGA analyses (heating rate of 10° C./min) of (A) Camp2 upon exposure to 25° C./60% RH for 24 months (Exp. ID GEN53) and (B) Camp2 upon exposure to 40° C./75% RH for 24 months (Exp. ID GEN57). A mass loss of 1.9 and 6.7% attributed to water was observed, respectively. The heat flow signals showed broad endotherms corresponding to the released of water followed by an endothermic event at 150° C. for GEN57.
Figure 34:
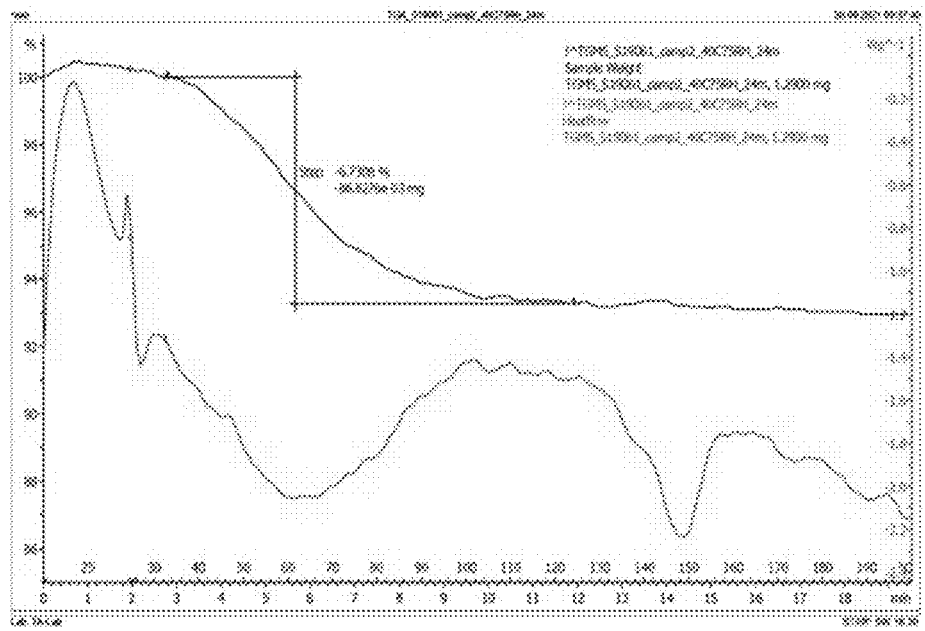

The sample of Camp2 incubated at 25° C./60% RH for 24 months showed a mass loss of 1.9%, similar to mass loss measured at previous timepoints (FIG. 34A), meaning that no significant water uptake occurred at this condition. The TGA analysis on the solid obtained after 24 month exposure to 40° C./75% RH (FIG. 34B) showed a water content of 6.7% (3.2 molecules of water per molecule of camsylate salt). The thermal behavior recorded in the heat flow signal showed a broad endotherm attributed to the water released followed by an endotherm at 150° C. which could be attributed to the melting of an anhydrous phase (different to Camp2, melting at 200° C.).

Figure 35:
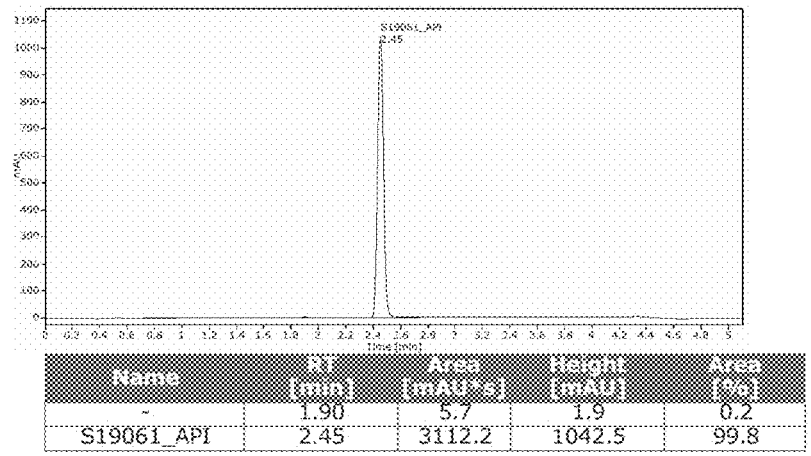
FIG. 35 shows HPLC chromatogram of Camp2 upon exposure to 25° C./60% RH for 1 month (Exp. ID GEN50). The API chemical purity was 99.8% (area %).
Figure 36:
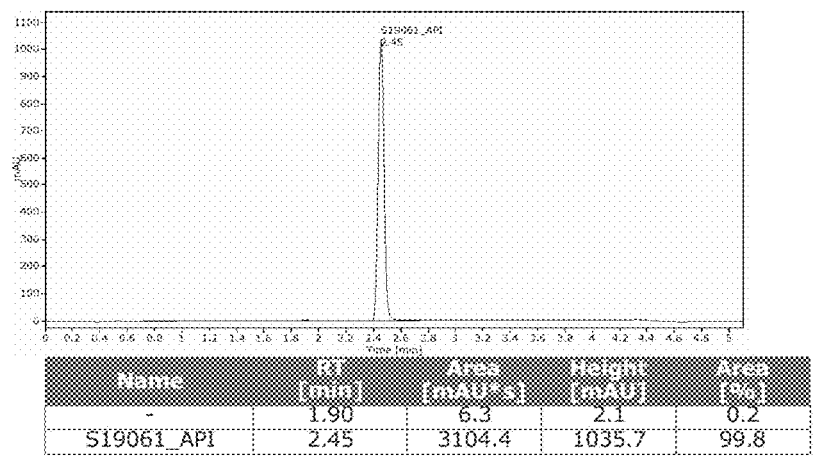
FIG. 36 shows HPLC chromatogram of Camp2 upon exposure to 40° C./75% RH for 1 month (Exp. ID GEN54). The API chemical purity was 99.8% (area %).
Figure 37:
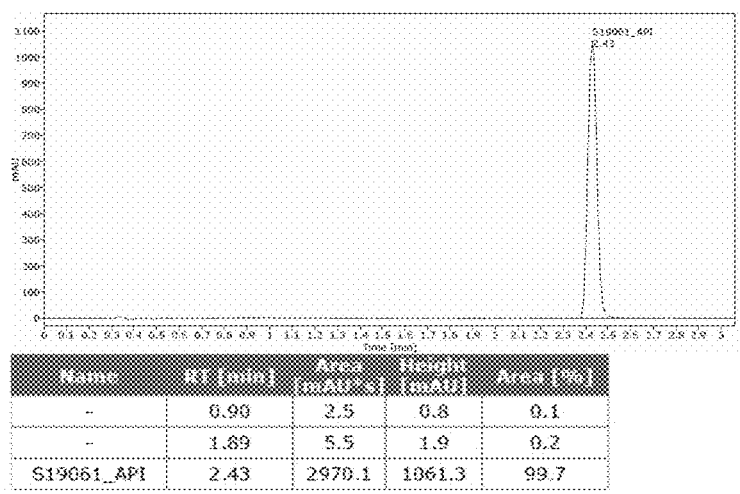
FIG. 37 shows HPLC chromatogram of Camp2 upon exposure to 25° C./60% RH for 3 months (Exp. ID GEN51). The API chemical purity was 99.7% (area %).
Figure 38:
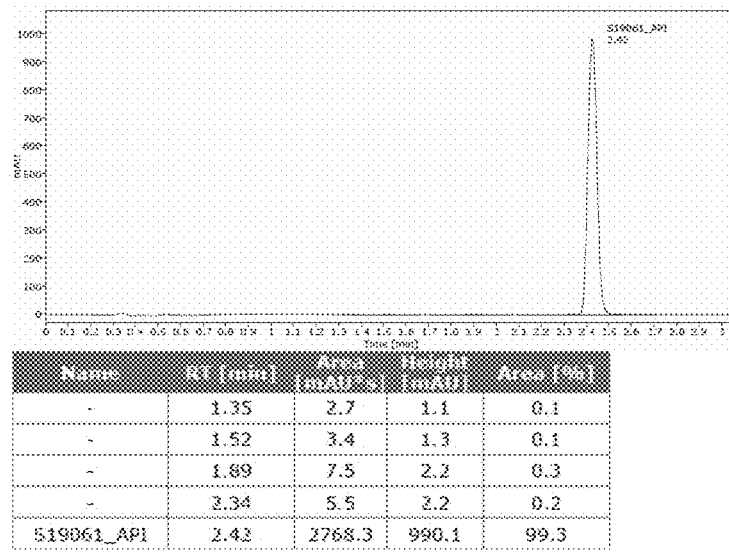
FIG. 38 shows HPLC chromatogram of Camp2 upon exposure to 40° C./75% RH for 3 months (Exp. ID GEN55). The API chemical purity was 99.3% (area %).

The chemical purity of Camp2 after exposure to 25° C./60% RH for 1 month (Exp. ID GEN50) upon exposure to 40° C./75% RH for 1 month (Exp. ID GEN54) was assessed by LCMS at 99.8% in both cases (FIG. 35 and FIG. 36) confirming that the API was present in the solid phase Camp2. After 3-months exposure, the chemical purity was comparable to the 1-month samples (FIG. 37 and FIG. 38).

Figure 39:
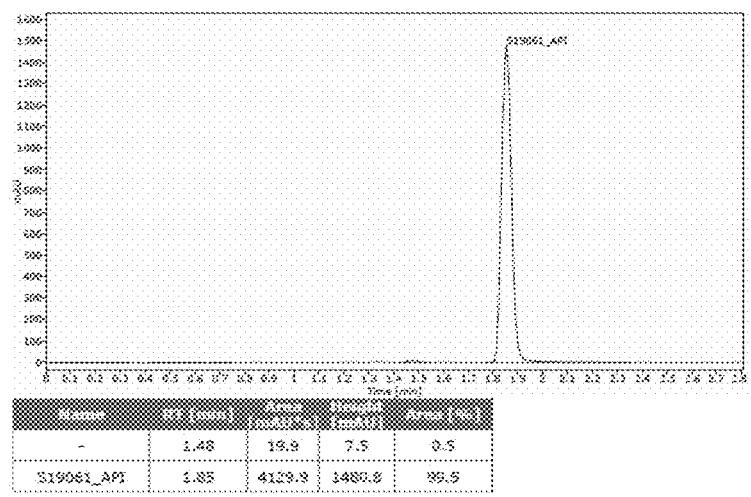
FIG. 39 shows HPLC chromatogram of Camp2 upon exposure to 25° C./60% RH for 15 months (Exp. ID GEN52). The API chemical purity was 97.3% (area %).
Figure 40:
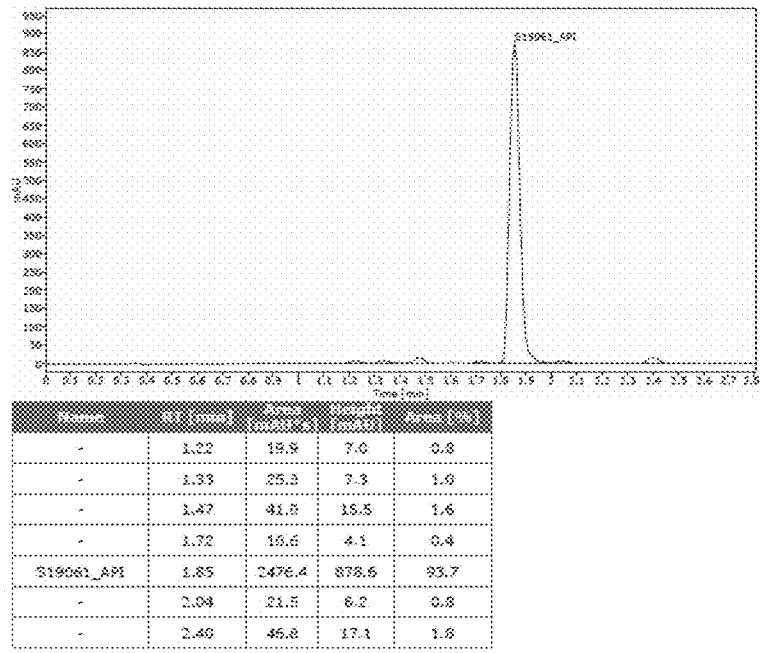
FIG. 40 shows HPLC chromatogram of Camp2 upon exposure to 40° C./75% RH for 15 months (Exp. ID GEN56). The API chemical purity was 93.7% (area %).

The chemical purity of Camp2 after 15 months exposure to 25° C./60% RH (Exp. ID GEN52) assessed by LCMS was 99.5% (FIG. 39), confirming that Camp2 is stable under this condition at least up to 15 months. The chemical purity of Camp4 after 15 months exposure to 40° C./75% RH (Exp. ID GEN56) assessed by LCMS was 93.7% (FIG. 40), confirming that once Camp2 had converted to Camp4 chemical degradation occurred at 40° C./75% RH.

Figure 41:
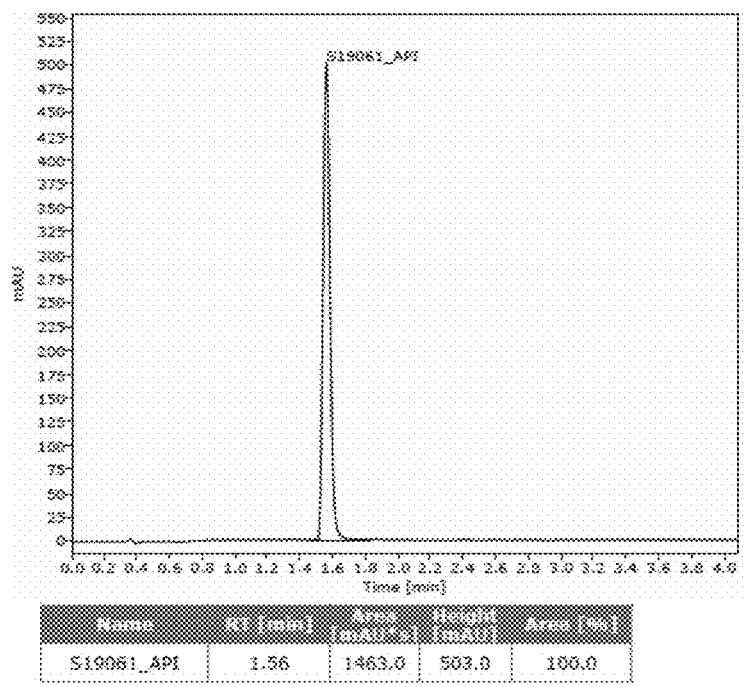
FIG. 41 shows HPLC chromatogram of Camp2 upon exposure to 25° C./60% RH for 15 months (Exp. ID GEN53). The API chemical purity was 100% (area %).
Figure 42:
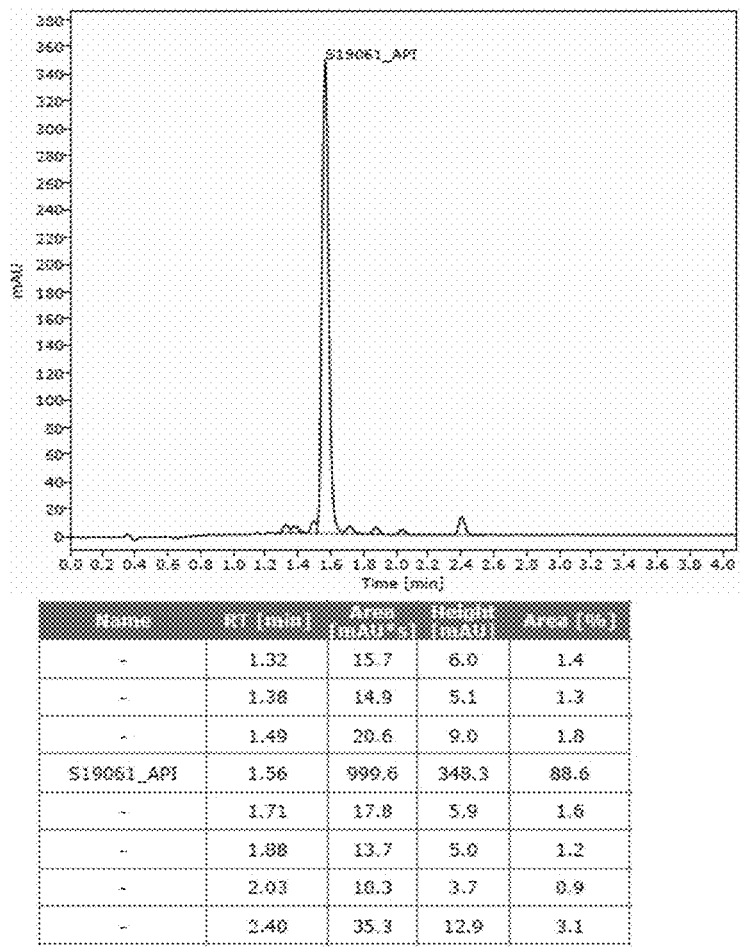
FIG. 42 shows HPLC chromatogram of Camp2 upon exposure to 40° C./75% RH for 15 months (Exp. ID GEN57). The API chemical purity was 88.6% (area %).

The chemical purity of Camp2 after 24 months exposure to 25° C./60% RH (Exp. ID GEN53) assessed by LCMS was 100% (FIG. 41), confirming that Camp2 is stable under this condition at least up to 24 months. The chemical purity of the camsylate salt after 24 months exposure to 40° C./75% RH (Exp. ID GEN57) assessed by LCMS was 88.6% (FIG. 42), confirming that once Camp2 had converted to different forms chemical degradation occurred at 40° C./75% RH.

Camsylate Salt Form Camp1

Figure 43:
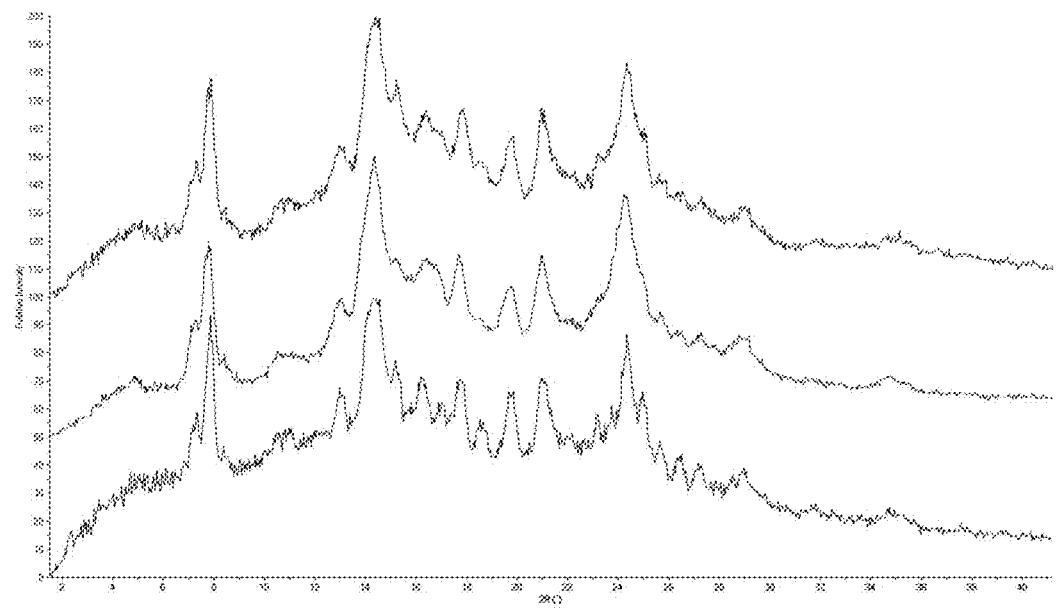
FIG. 43 shows HT-XRPD patterns of (from bottom to top) Camp1 obtained in the salt screen (Exp. ID SSm14), after thermocycling in MTBE (Exp. ID GEN21) before and after exposure to AAC (40° C./75% RH) for 2 days.

Camp1 was obtained during the polymorph screen performed by thermocycling the low crystalline camsylate salt (obtained by freeze-drying). The crystallization solvents that led to Camp1 were ethyl acetate, p-xylene and MTBE. The solid selected for further characterization was the salt crystallized from MTBE. Camp1 was obtained in the ambient dried and it was physically stable upon drying under vacuum and upon exposure to AAC (40° C./75% RH) for 2 days (FIG. 43).

Figure 44:
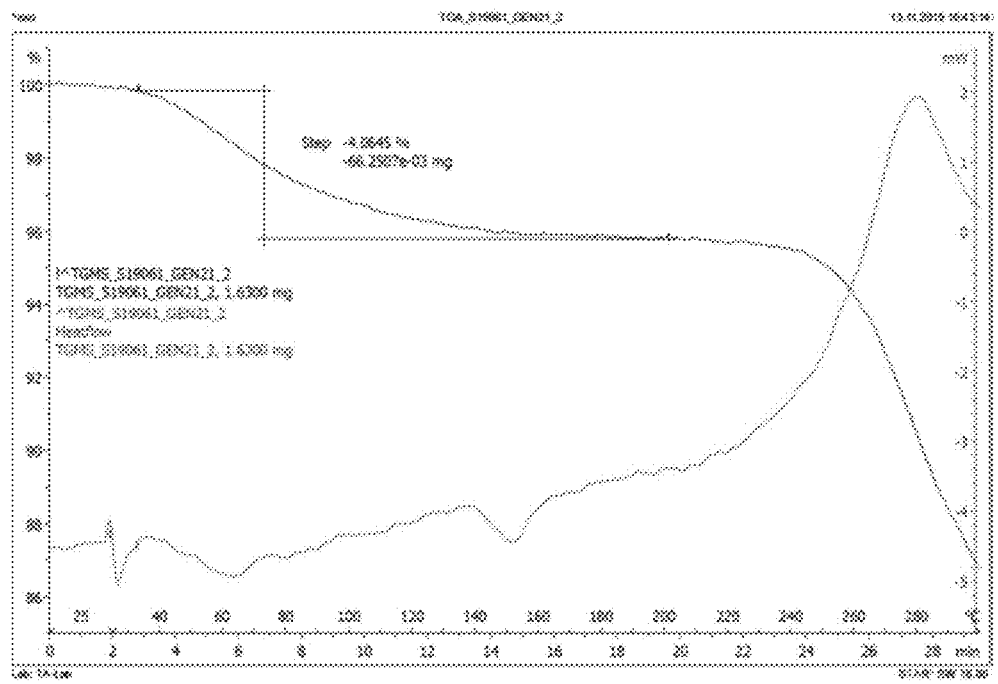
FIG. 44 shows TGA (A) and TGMS (B) analysis (heating rate of 10° C./min) of Camp1 obtained from the thermocycling experiment performed in MTBE (Exp. ID GEN21). A mass loss of 4.1% attributed to water and MTBE (based on the MS signal) was observed between 25-200° C. Thermal decomposition of the salt was observed above 240° C. The heat flow signal of the TGA showed an endotherm at 155° C., possibly attributed to the melting of an anhydrous phase of the salt.
Figure 44:
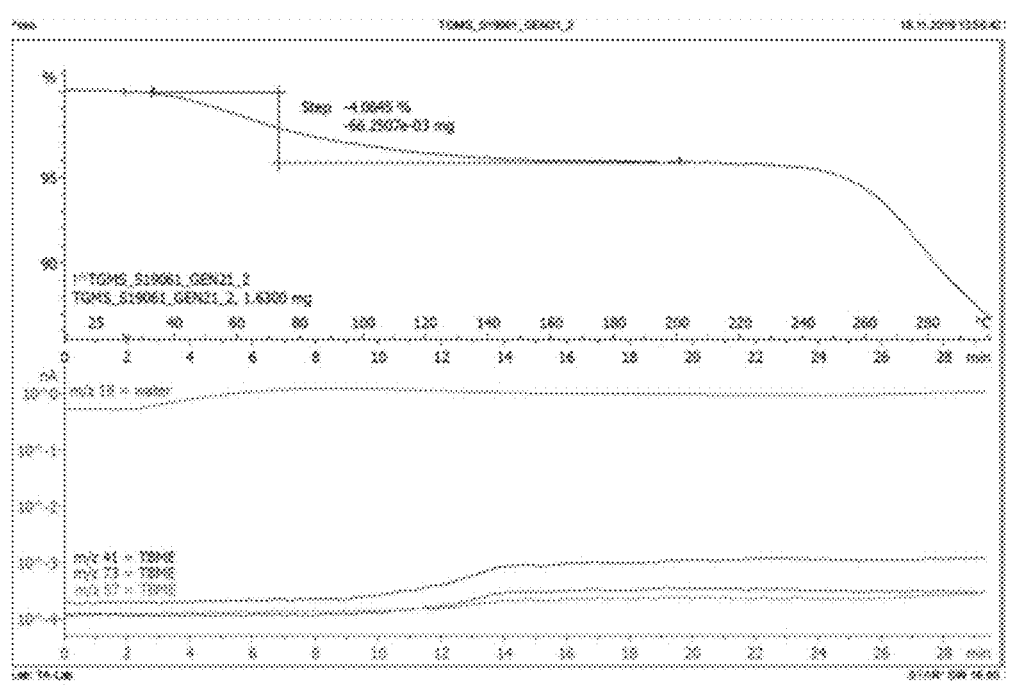

The TGA/TGMS analysis of Camp1 (FIG. 44) showed a mass loss of 4.1% from 40 to 200° C., most likely due to water and MTBE based on the MS signal. The thermal decomposition is observed at temperatures above 240° C. In the heat flow signal, an endothermic event was observed at around 155° C. possibly attributed to the melting of an anhydrous phase of the salt.

Figure 45:
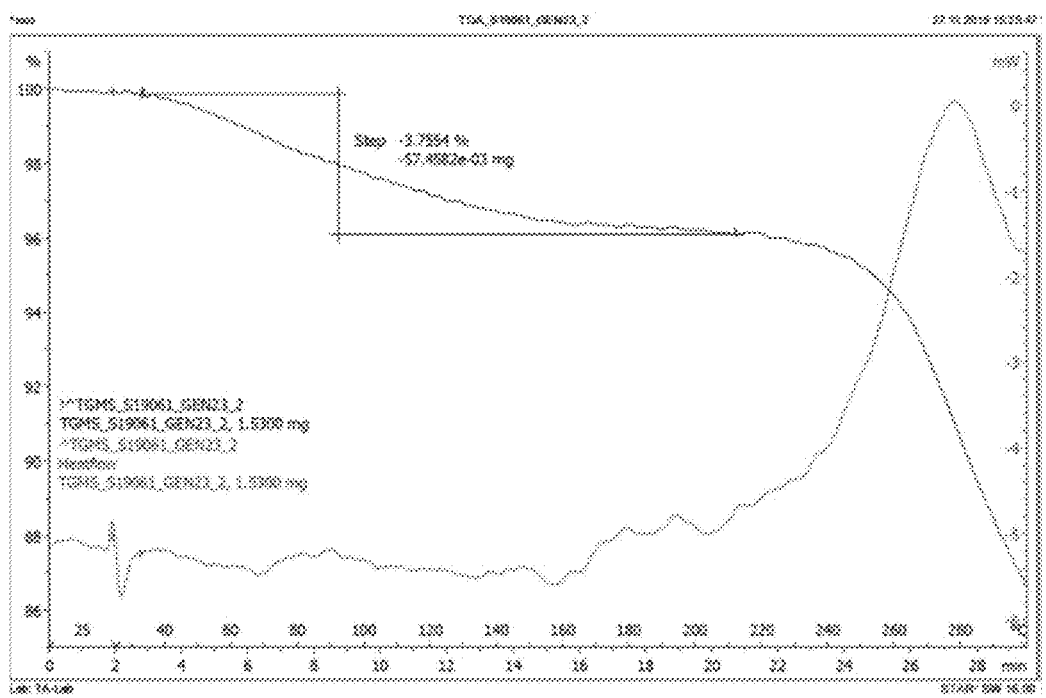
FIG. 45 shows TGA (A) and TGMS (B) analysis (heating rate of 10° C./min) of Camp1 obtained from the thermocycling experiment performed in water (Exp. ID GEN23). A mass loss of 3.8% attributed to water was observed between 25-200° C. Thermal decomposition of the salt was observed above 240° C.
Figure 45:
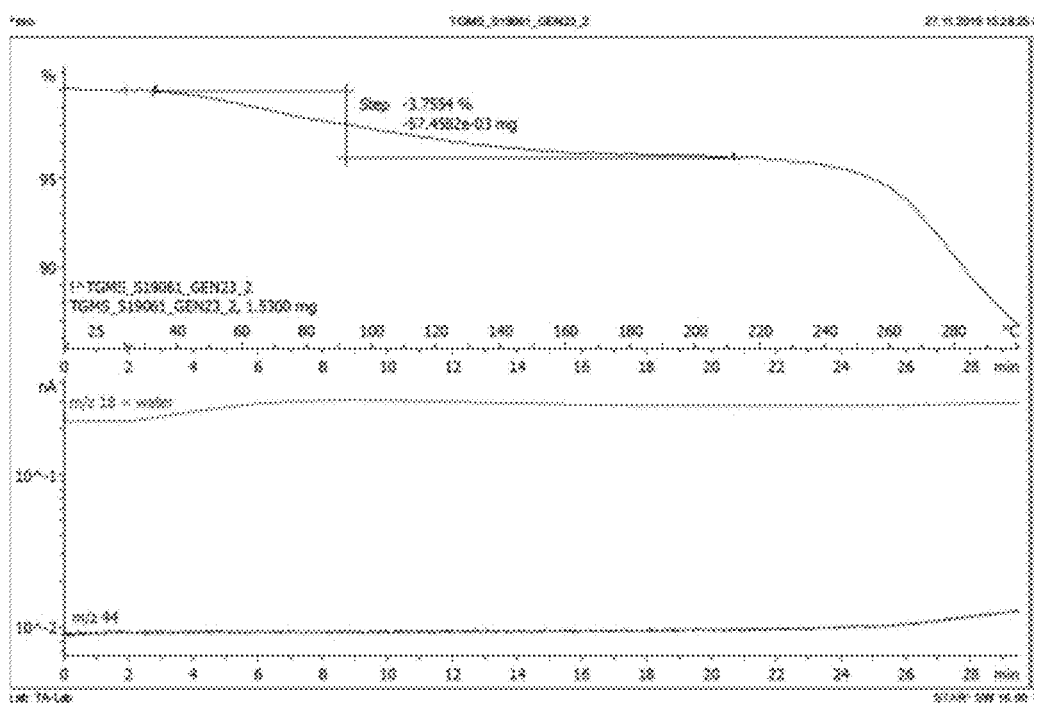

A second sample of Camp1 obtained from water (from Exp. ID GEN23) was analyzed by TGA/TGMS (FIG. 45) showed a mass loss of 3.8% from 25 to 200° C. attributed to water based on the MS signal (3.8% corresponds to 1.8 molecule of water per salt molecule). The thermal decomposition is observed at temperatures above 240° C.

Based on the thermal analyses performed on Camp1, it seems that Camp1 can be a hydrate or a mix hydrate/solvate, where either water and/or organic solvent molecules can be incorporated in the lattice. Based on the gradual water low observed in the TGA, it is likely that the water/organic solvent molecules are located in channels or voids present in the structure, giving to Camp1 a non-stoichiometric nature.

Figure 46:
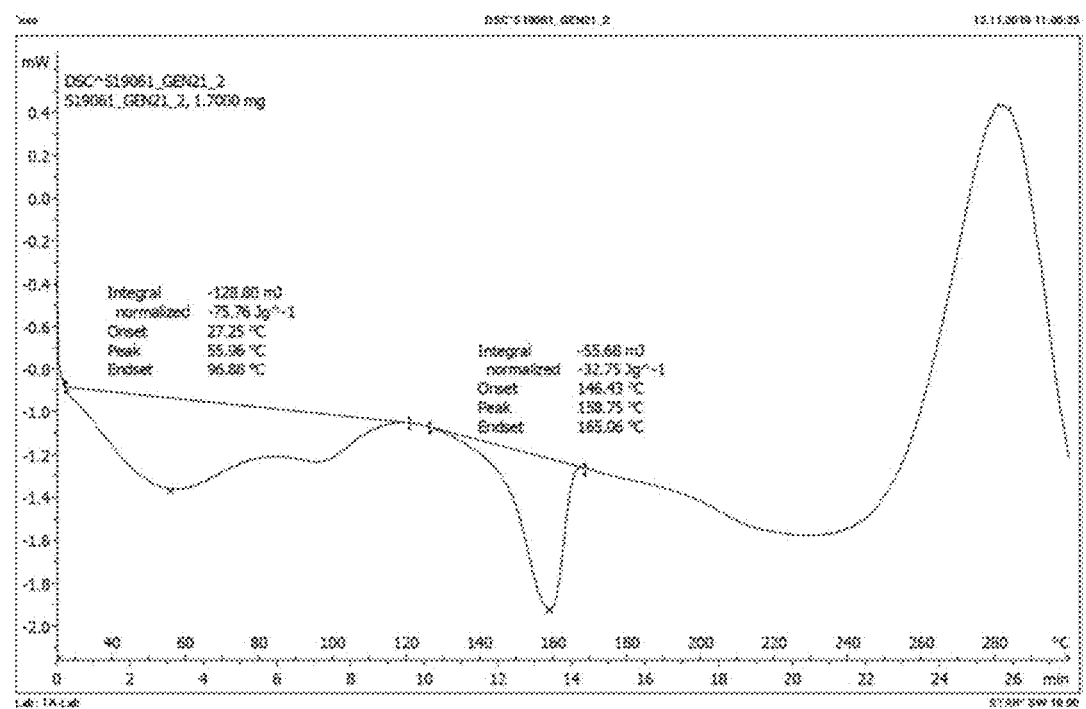
FIG. 46 shows DSC curve (heating rate 10° C./min) of Camp1 obtained from the thermocycling experiment performed in MTBE (Exp. ID GEN21). The DSC curve showed a broad endothermic event between 25 to 120° C. that can be related to the water/MTBE loss. A subsequent endothermic event at 158.8° C. was observed which can be attributed to the melting of a potential anhydrous salt.

The DSC trace of Camp1 from Exp. ID GEN21 (FIG. 46) showed a broad endothermic event between 25 to 120° C., that could be related to the water/solvent loss. Subsequently, an endothermic event was observed at 158.8° C. that could be related to the melting of a potential anhydrous camsylate salt.

Figure 47:
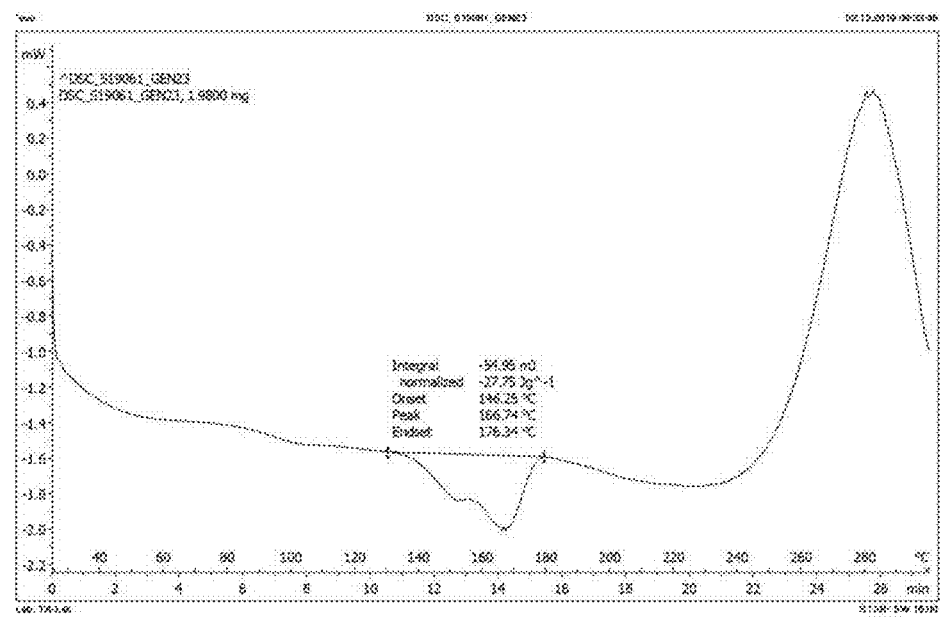
FIG. 47 shows DSC curve (heating rate 10° C./min) of Camp1 obtained from the thermocycling experiment performed in water (Exp. ID GEN23). The DSC curve showed broad endothermic events between 25 to 80° C. that can be related to the water loss. A broad endothermic event between 130-180° C. that can be attributed to the melting of a potential anhydrous salt was observed.

The DSC trace of Camp1 from Exp. ID GEN23 (FIG. 47) showed a broad endothermic event between 25 to 80° C., that could be related to the water loss. Subsequently, two broad endotherms were observed in the range 130-180° C., that could be related to the release of water molecules tightly bounded to the crystal lattice.

Figure 48:
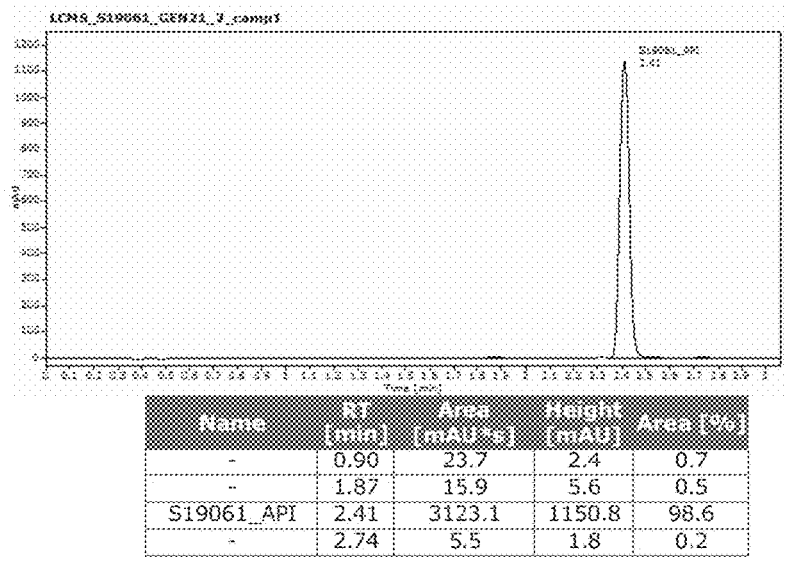
FIG. 48 shows LCMS chromatogram of Camp1 (Exp. ID GEN21). The API chemical purity was 98.6% (area %).

The chemical purity of Camp1 was assessed by LCMS to 98.6% (FIG. 48) confirming that the API was present in the solid phase Camp1.

Figure 49:
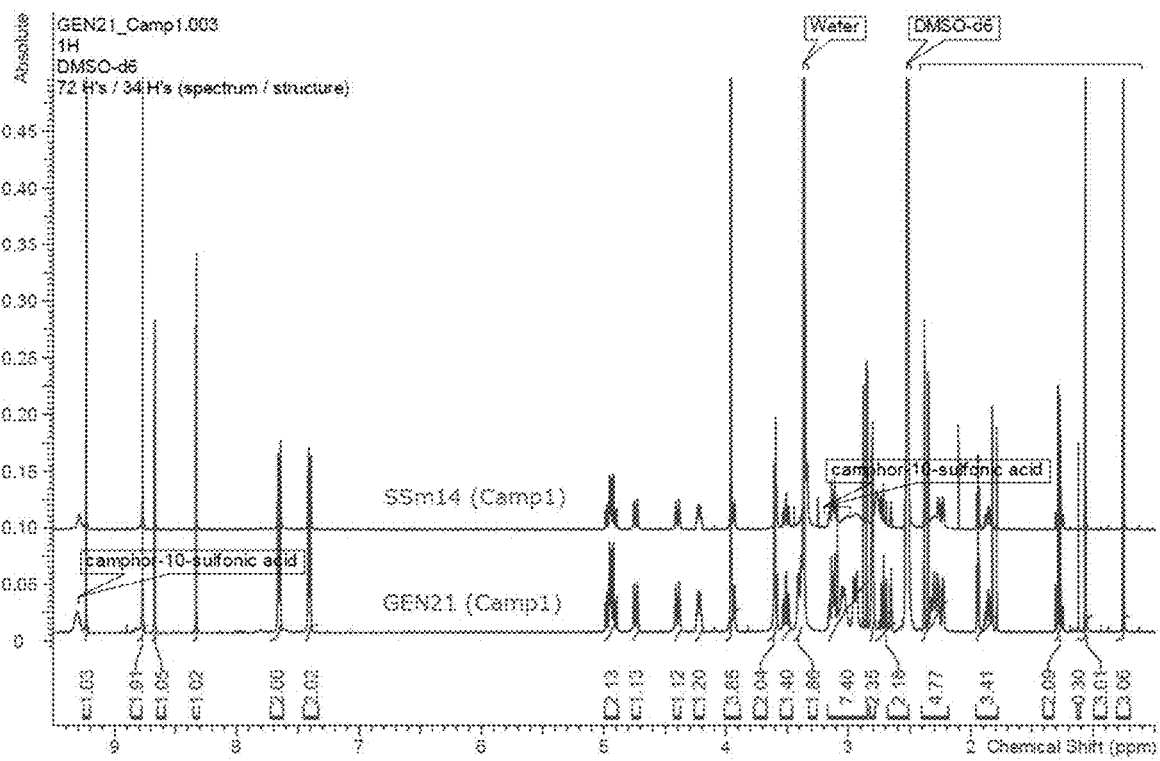
FIG. 49 shows Overlay of $^1$H-NMR spectra (500 MHz, DMSO-d6) of Camp1 from Exp. ID GEN21 (red line) and Camp1 from Exp. ID SSm14 (green line). The peaks corresponding to the CI were highlighted by the signals appearing at 9.3, 3.0, 2.7, 2.6 and 2.3 ppm and from 2.0 to 0.8 ppm.

The 1H-NMR analysis of Camp1 obtained in Exp. ID GEN21 is shown in FIG. 49. This spectrum overlapped with that previously reported for Camp1 from Exp. ID SSm14. Based on the similarities we can confirm that proton transfer occurred. The ratio API:CI was calculated to 1:1.

Camsylate Salt Form Camp2

Figure 50:
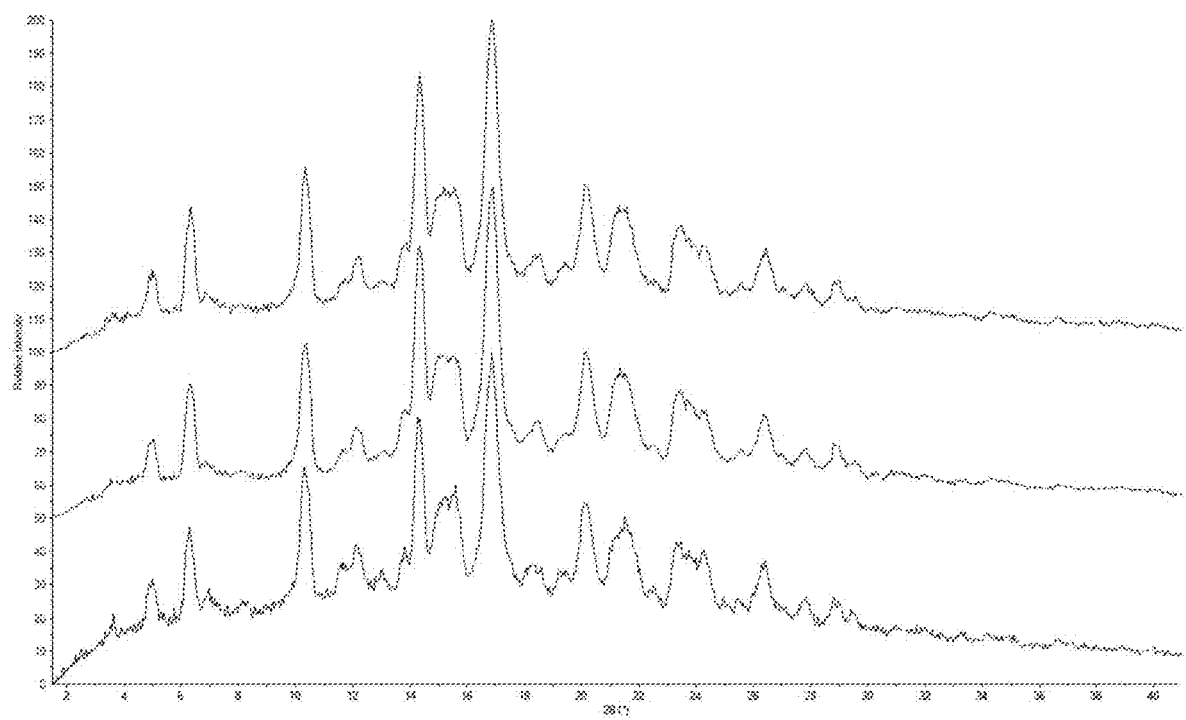
FIG. 50 shows HT-XRPD patterns of (from bottom to top) Camp2 obtained in the salt screen (Exp. ID SSm60), after thermocycling in ethanol (Exp. ID GEN17) before and after exposure to AAC (40° C./75% RH) for 2 days.

Camp2 was the most occurring solid form found in the polymorph screen performed on the camsylate salt, especially in the vacuum-dried solids. In a few experiments, a mixture of Camp4+Camp2 was detected, which upon drying under vacuum or exposure to AAC converted to Camp2. The experiment in THF led to Camp5 in the ambient-dried solids which upon drying under vacuum converted to Camp2. In Table 45, the experimental conditions producing Camp2 are presented. Camp2 was physically stable upon exposure to AAC (40° C./75% RH) for 2 days (FIG. 50).

Figure 51:
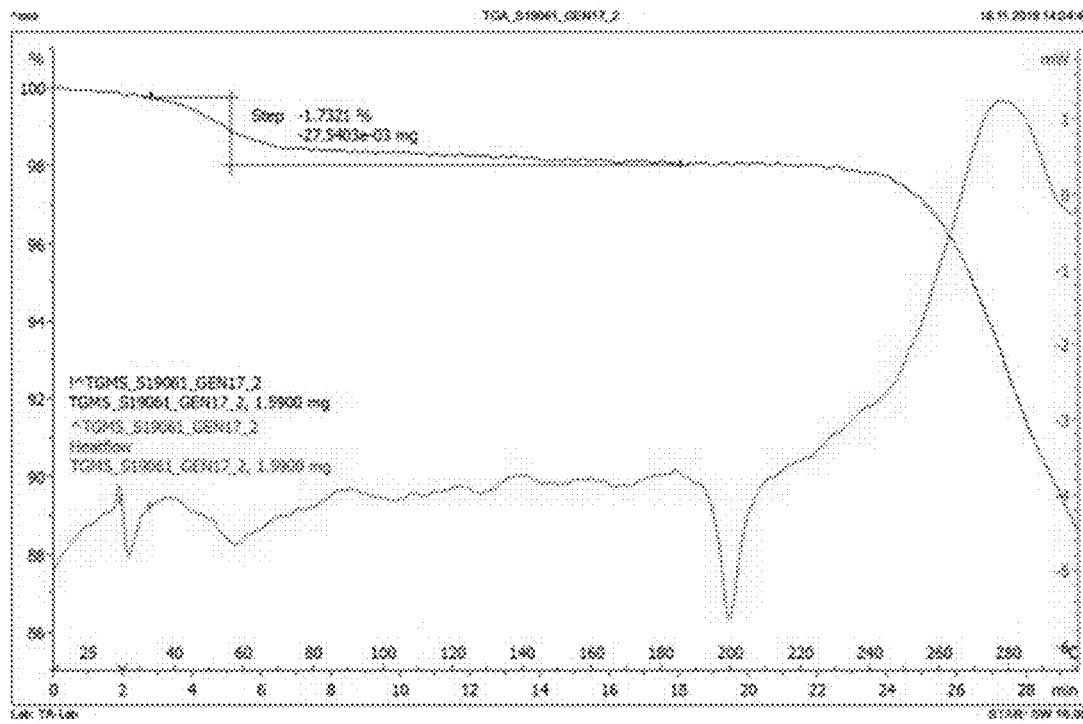
FIG. 51 shows TGA (A) and TGMS (B) analysis (heating rate of 10° C./min) of Camp2 obtained from the thermocycling experiment performed in ethanol (Exp. ID GEN17). A mass loss of 1.7% attributed to water was observed between 25-180° C. Thermal decomposition of the salt was observed above 240° C. The heat flow signal of the TGA showed a sharp endotherm at 200° C. possibly attributed to the melting of the anhydrous salt form.
Figure 51:
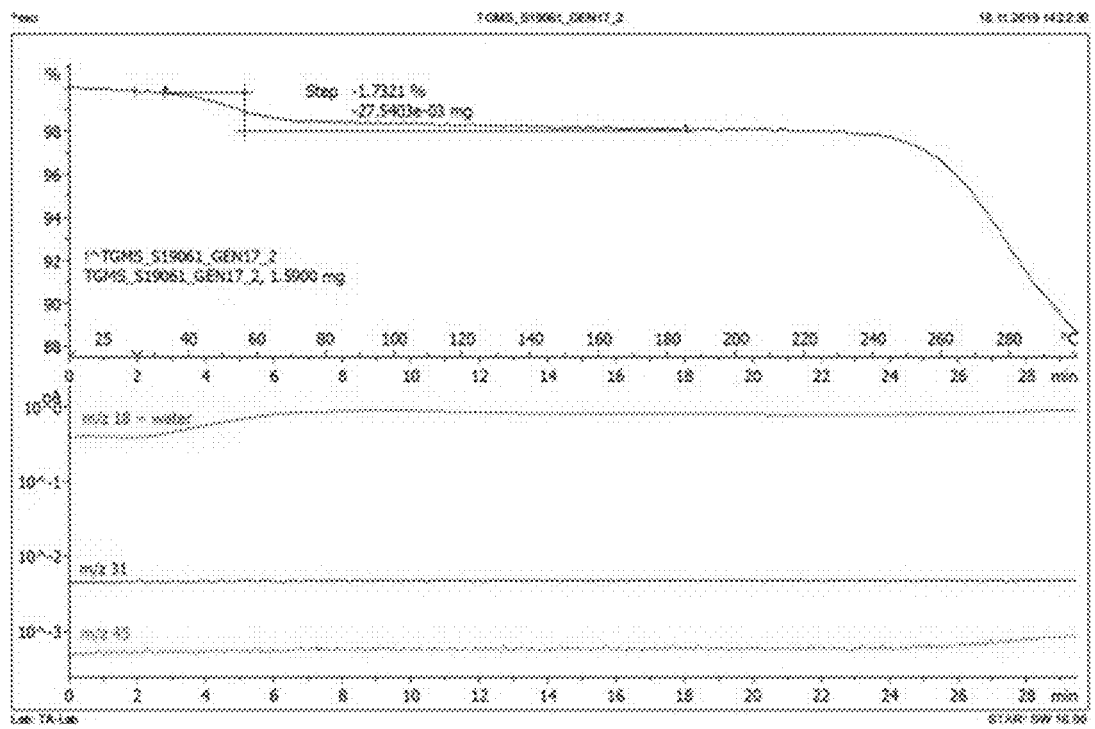

The TGA/TGMS analysis of Camp2 (FIG. 51) showed a mass loss of 1.7% from 25 to 180° C. attributed to water, based on the MS signal (1.7% corresponds to 0.7 molecules of water per salt molecule). The thermal decomposition is observed at temperatures above 240° C. In the heat flow signal a sharp endothermic event was observed at around 200° C. attributed most likely to the melting of an anhydrous phase of the salt, followed by decomposition.

TABLE 9

Experimental conditions producing Camp2.

| Exp. ID | Solvent | Form Ambient | Form after AAC |
|---------|---------|--------------|----------------|
| GEN12 | 1,4-Dioxane | Camp2 + Camp4 | Camp2 |
| GEN13 | IPA | Camp2 + Camp4 | Camp2 |
| GEN14 | Acetone | Camp2 + Camp4 | Camp2 |
| GEN15 | Acetonitrile | Camp2 + Camp4 | Camp2 |
| GEN17 | Ethanol | Camp2 | Camp2 |
| GEN21 | THF | Camp5 | Camp2 |

Figure 52:
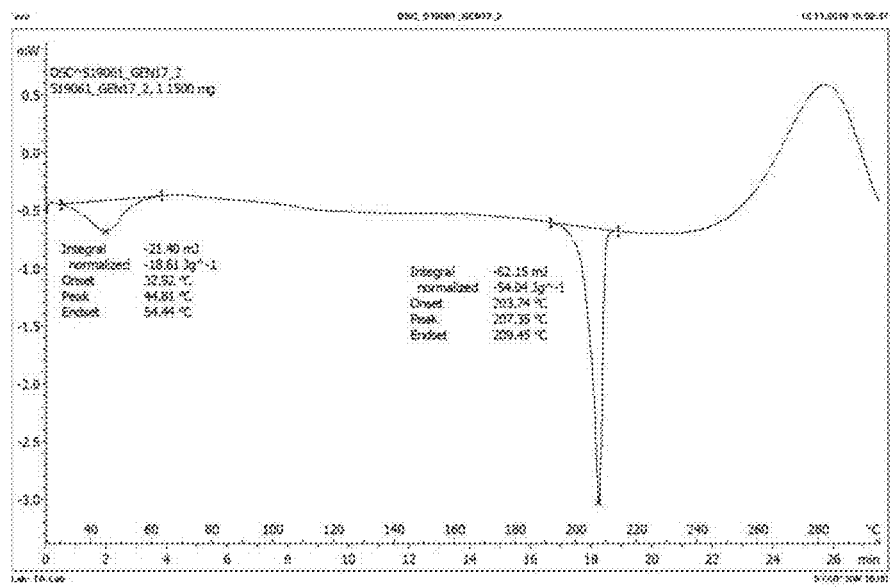
FIG. 52 shows DSC curve (heating rate 10° C./min) of Camp2 obtained from the thermocycling experiment performed in ethanol (Exp. ID GEN17). The DSC curve showed a broad endothermic event from 25 to 60° C. associated to the water loss. An endothermic event at 207.4° C. could possibly be correlated to the melting of an anhydrous phase of the salt.

The DSC trace of Camp2 (FIG. 52) showed a broad endothermic event between 25 and 70° C., associated to the water loss. An endothermic event was recorded at 208.9° C. that could possibly be correlated to the melting of an anhydrous phase of the salt.

Figure 53:
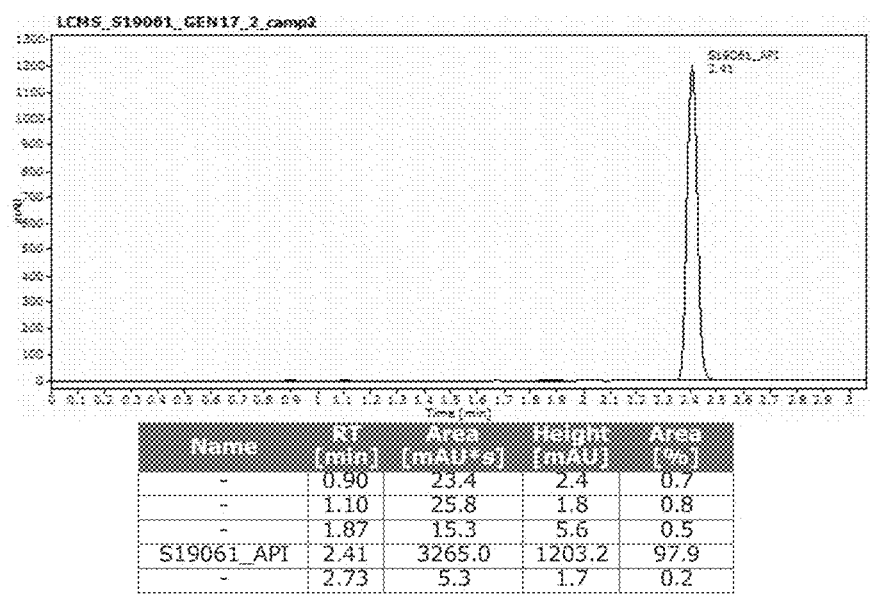
FIG. 53 shows LCMS chromatogram of Camp2 obtained from the thermocycling experiment performed in ethanol (Exp. ID GEN17). The API chemical purity was 97.9% (area %).
Figure 54:
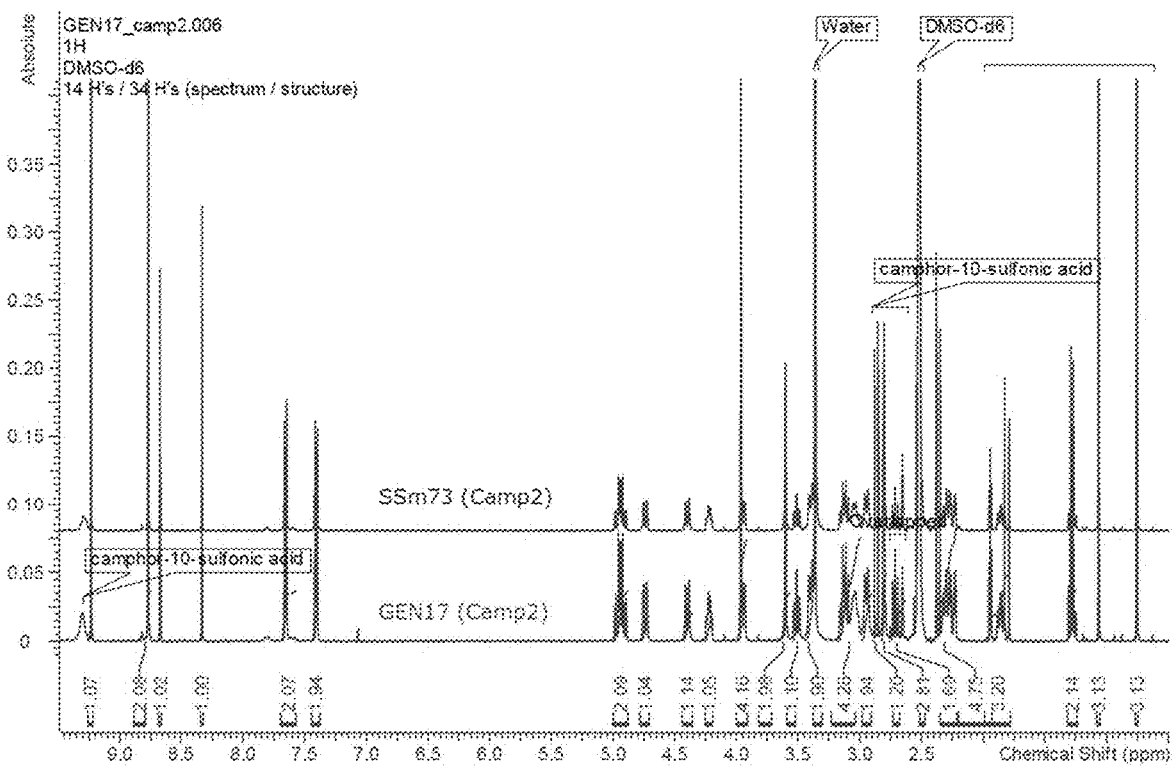
FIG. 54 shows overlay of $^1$H-NMR spectra (500 MHz, DMSO-d6) of Camp2 from Exp. ID GEN17 (red line) and Camp2 from Exp. ID SSm73 (green line). The peaks corresponding to the CI were highlighted by the signals at 9.3, 3.0, 2.7, 2.6 and 2.3 ppm and from 2.0 to 0.8 ppm.

The chemical purity of Camp2 was assessed by LCMS to 97.9% (FIG. 53) confirming that the API was present in the solid phase Camp2. The 1H-NMR analysis of Camp2 obtained in Exp. ID GEN17 is shown in FIG. 54, together with the 1H-NMR spectrum of Camp2 obtained in Exp. ID SSm73. Based on the similarities, we can confirm that proton transfer occurred. The ratio API:CI was calculated to 1:1.

Camsylate Salt Form Camp4

Figure 55:
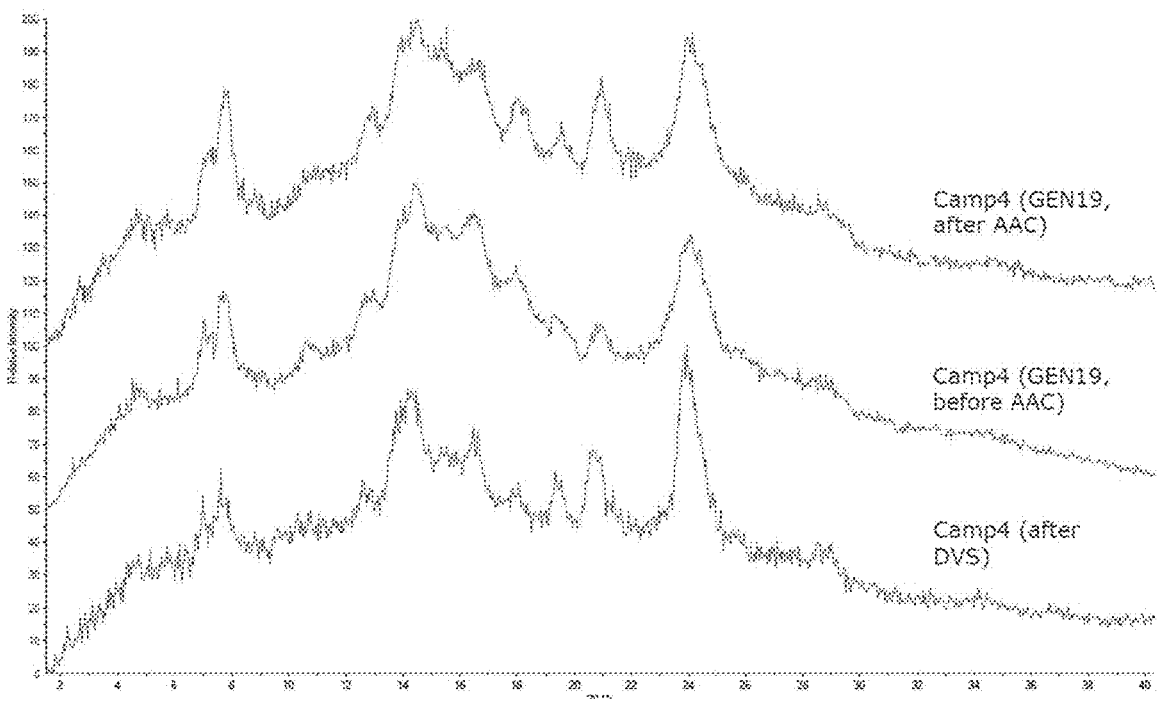
FIG. 55 shows HT-XRPD patterns of (from bottom to top) Camp4 obtained after a DVS analysis performed on Camp2 (Exp. ID SSm70 after DVS) after thermocycling in n-heptane (Exp. ID GEN19) before and after exposure to AAC (40° C./75% RH) for 2 days.

Camp4 was obtained from several thermocycling experiments performed on the camsylate salt. Table 46 reports the experimental conditions producing Camp4 in this study. The sample selected for further analytics was Camp4 from Exp. ID GEN19 (from heptane). Camp4 was physically stable upon exposure to AAC (40° C./75% RH) for 2 days (FIG. 55).

Figure 56:
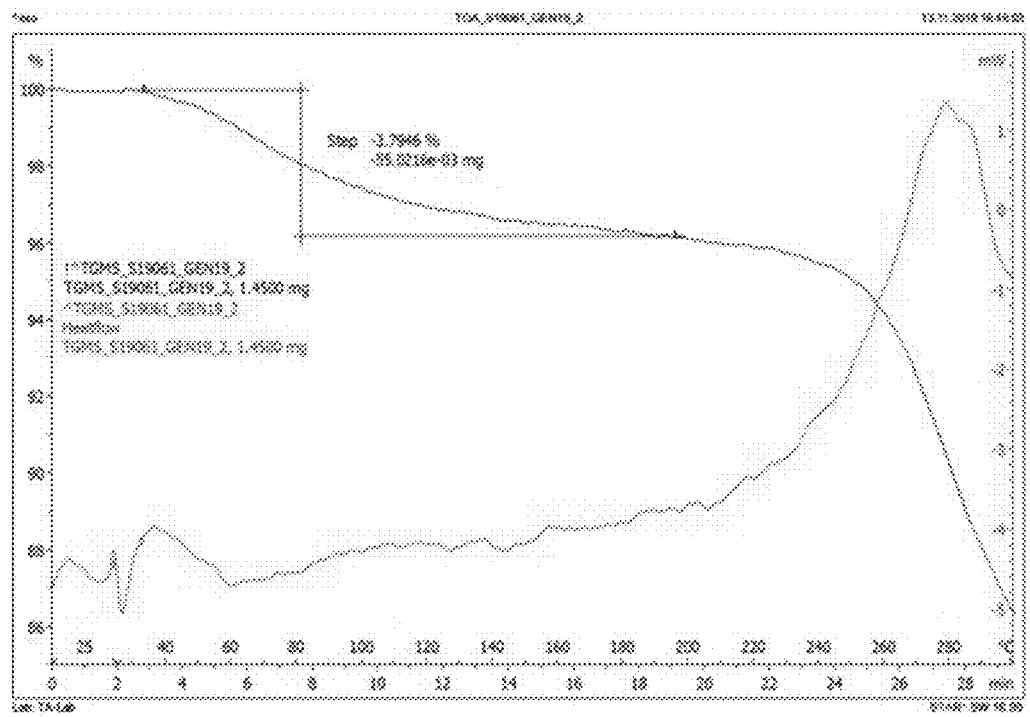
FIG. 56 shows TGA (A) and TGMS (B) analysis (heating rate of 10° C./min) of Camp4 obtained after thermocycling in n-heptane (Exp. ID GEN19). A mass loss of 3.8% attributed to water and heptane was detected between 25-200° C. Thermal decomposition of the salt was observed above 240° C.
Figure 56:
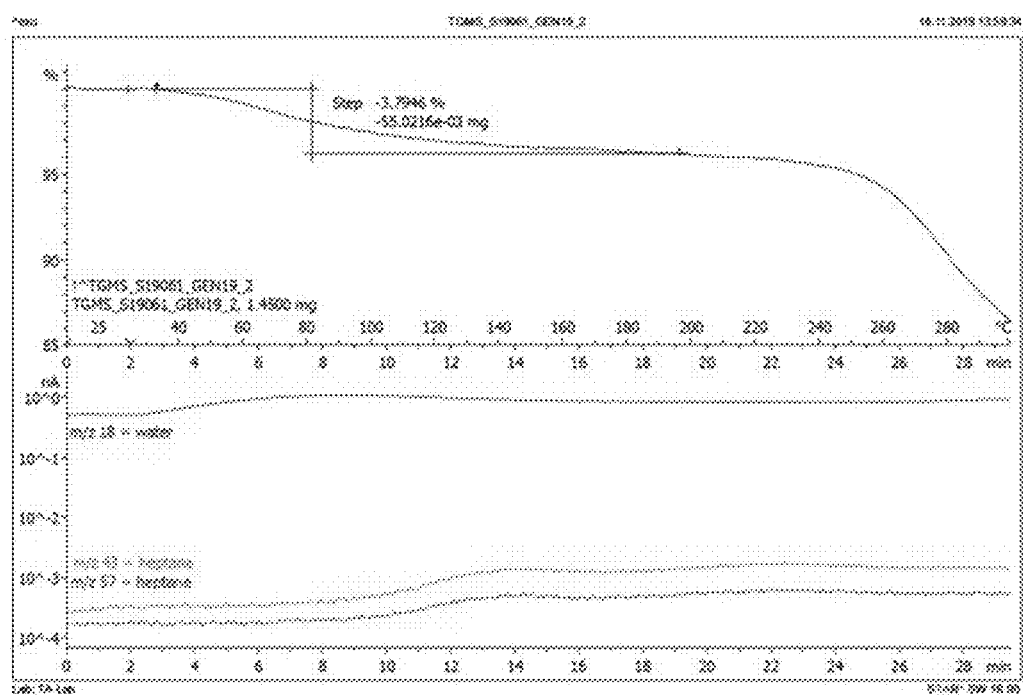
Figure 57:
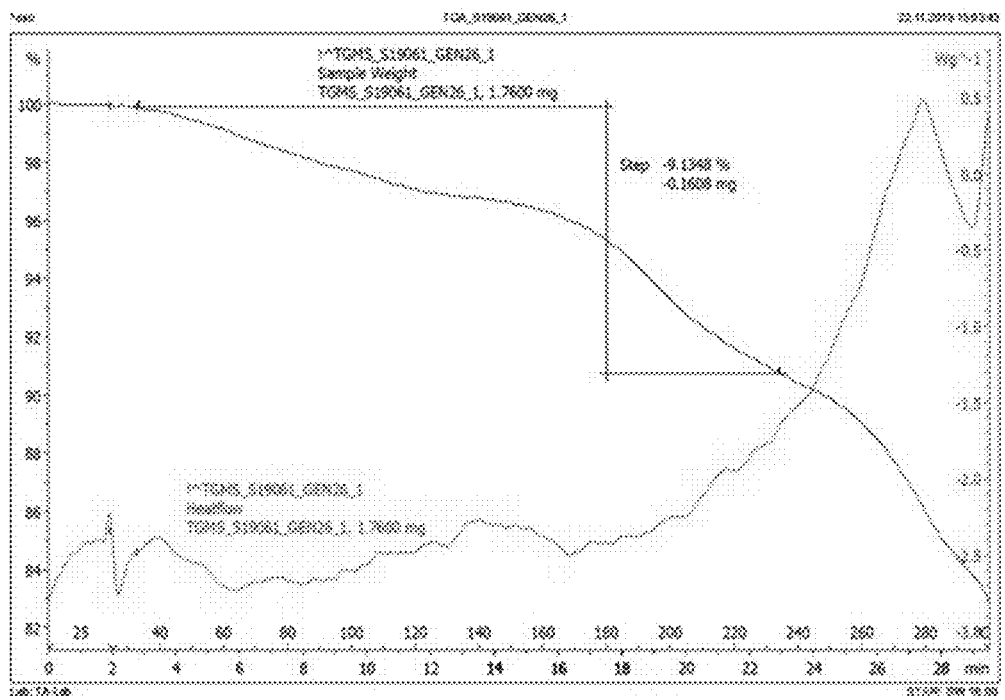
FIG. 57 shows TGA (A) and TGMS (B) analysis (heating rate of 10° C./min) of Camp4 obtained after thermocycling in THF/water (95/5) (Exp. ID GEN26). A mass loss of 9.1% attributed to water and THF was detected between 25-230° C. Thermal decomposition of the salt was observed above 240° C.
Figure 57:
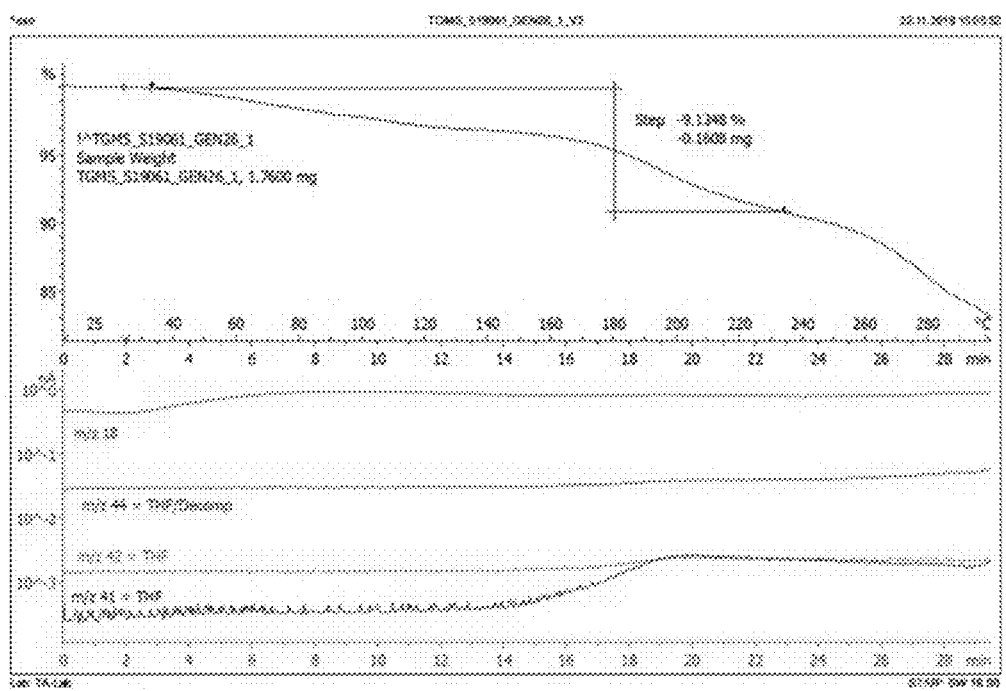

The TGA/TGMS analysis of Camp4 (FIG. 56) showed a mass loss of 3.8% from 25 to 200° C. attributed to water and heptane, based on the MS signal. Thermal decomposition was observed at temperatures above 240° C. A second TGMS analysis (FIG. 57) was performed on Camp4 obtained from THF/water (95/5). A mass loss of 9.1% was recorded from 40 to 230° C. attributed to water and THF, based on the MS signal. About 3.2% could be attributed to water (1.5 molecules of water) and 5.9% to THF (0.7 molecules of THF). The thermal decomposition is observed at temperatures above 240° C.

TABLE 10

Experimental conditions producing Camp4.

| Exp. ID | Solvent | Form | Form after AAC |
|---------|---------|------|----------------|
| GEN16 | Chloroform | Camp4* | Camp4 |
| GEN19 | Heptane | Camp4 | Camp4 |
| GEN23 | IPA/Water (97/3) | Camp4 | lc |
| GEN25 | 1,4-Dioxane/Water (96/4) | Camp4* | Camp4 |
| GEN26 | THF/Water (95/5) | Camp4* | Camp4 |

The notation "lc" stands for low crystalline.
Camp4* was obtained after evaporative crystallization since no solid were recovered after the temperature profile.

Figure 58:
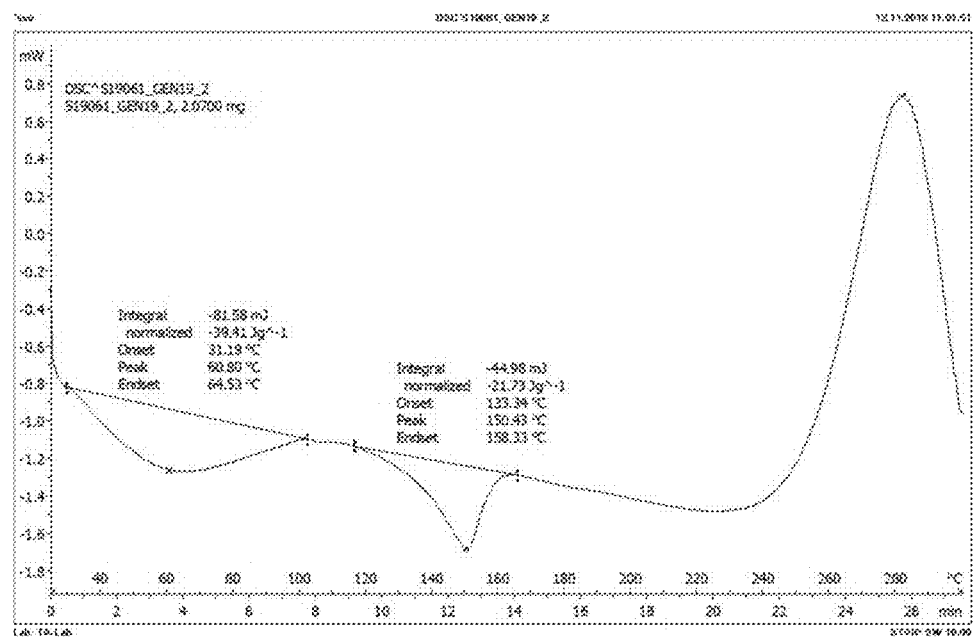
FIG. 58 shows DSC curve (heating rate 10° C./min) of Camp4 obtained after thermocycling in n-heptane (Exp. ID GEN19). The DSC curve showed a broad endothermic event from 25 to 100° C. associated to the water loss. An endothermic event at 150.4° C. could possibly be correlated to the loss of heptane.

The DSC trace of Camp4 from the experiment performed in heptane (FIG. 58) showed a broad endothermic event between 25 and 100° C., associated with the water loss. A subsequent broad endotherm was recorded at 150.4° C. that could possibly be correlated to the loss of heptane. No other thermal events were observed prior to the thermal decomposition, which suggested that after the water/solvent loss, the crystal structure of Camp4 collapses.

Figure 59:
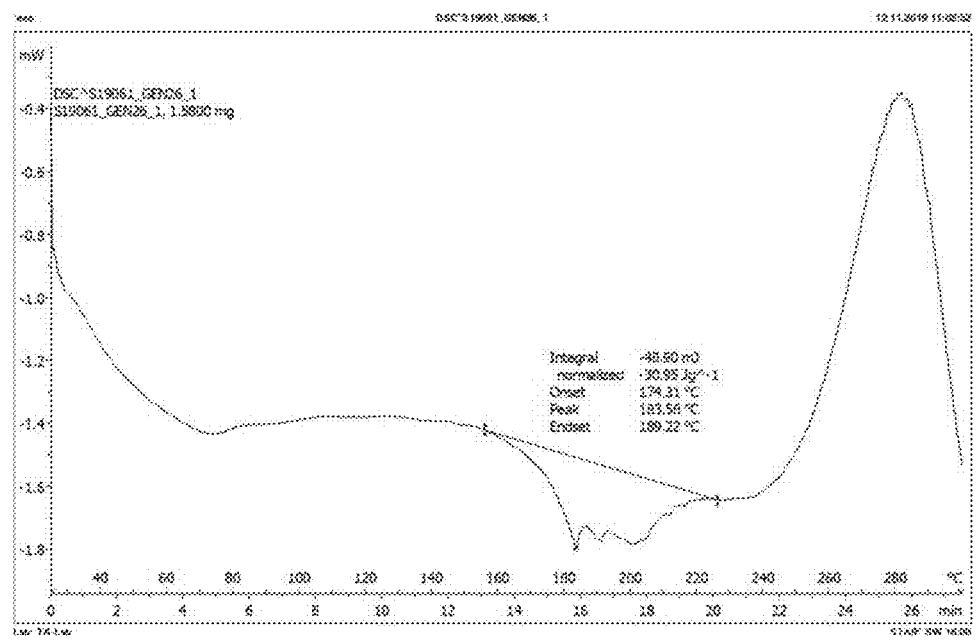
FIG. 59 shows DSC curve (heating rate 10° C./min) of Camp4 obtained after thermocycling in THF/water (95/5) (Exp. ID GEN26). The DSC curve showed a broad endothermic event from 25 to 140° C. associated to the water loss. A second broad endothermic event between 160-225° C. was observed that could possibly be correlated to the THF loss.

The DSC trace of Camp4 from the experiment performed in THF/water (95/5) (FIG. 59) showed a broad endothermic event between 25 and 140° C., associated to the water loss. A subsequent broad endotherm was recorded between 160-220° C. that could possibly be correlated to the loss of THF. No other thermal events were observed prior to the thermal decomposition.

Figure 60:
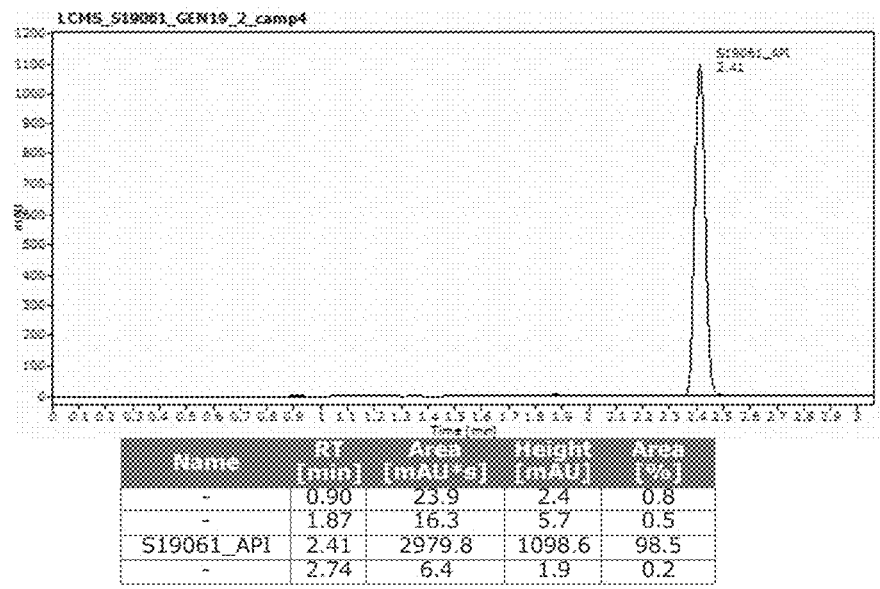
FIG. 60 shows LCMS chromatogram of Camp4 obtained after thermocycling in n-heptane (Exp. ID GEN19). The API chemical purity was 98.5% (area %).
Figure 61:
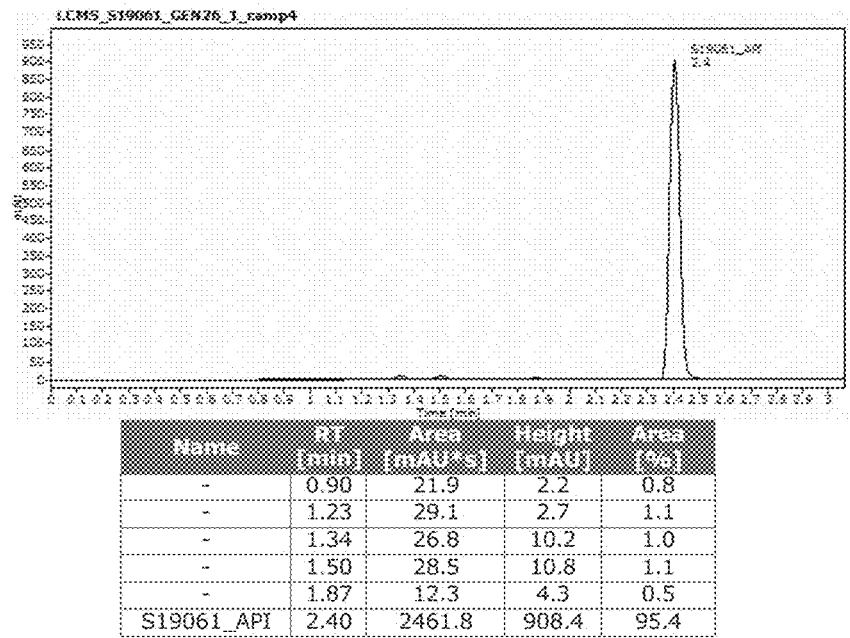
FIG. 61 shows LCMS chromatogram of Camp4 obtained after thermocycling in THF/water (95/5) (Exp. ID GEN26). The API chemical purity was 95.4% (area %).

The chemical purity of Camp4 from both samples was assessed by LCMS at 98.5% and 95.4%, respectively (FIG. 60 and FIG. 61) confirming that the API was present in the solid phase Camp4; however, it seems that in the presence of water partial chemical degradation is occurring.

Figure 62:
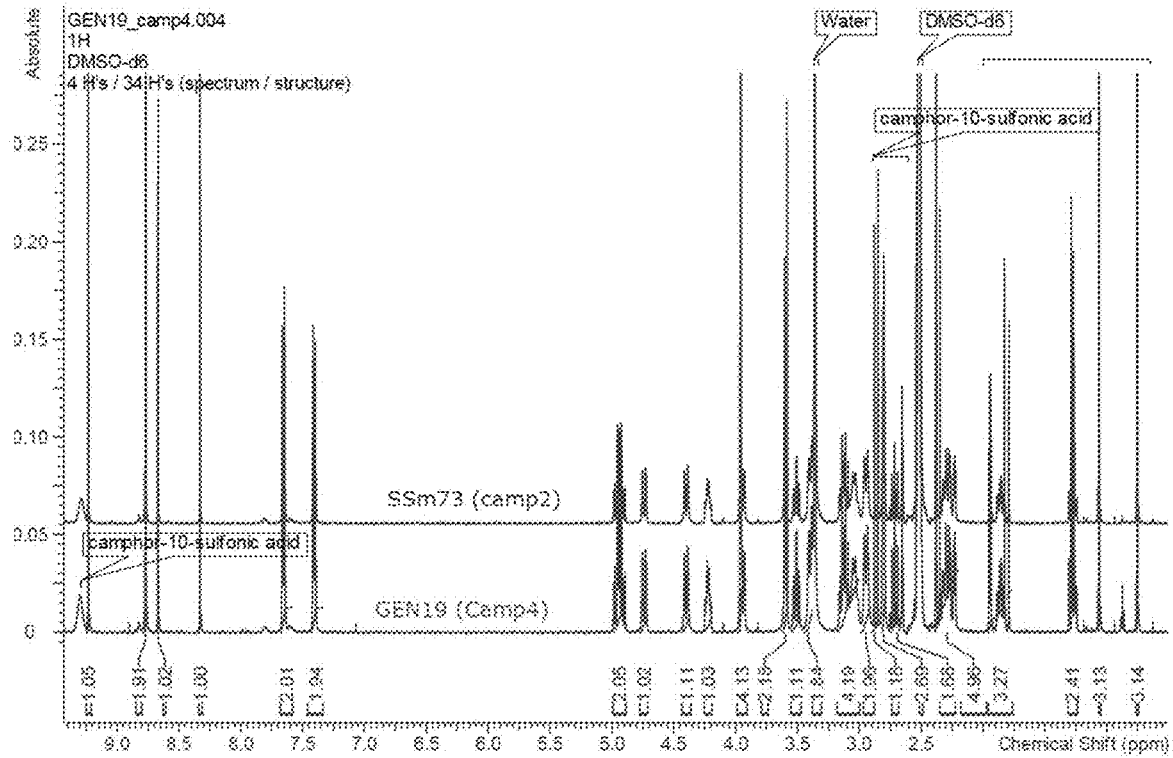
FIG. 62 shows Overlay of $^1$H-NMR spectra (500 MHz, DMSO-d6) of Camp4 from Exp. ID GEN19 (red line) and Camp2 from Exp. ID SSm73 (green line). The peaks corresponding to the CI were highlighted by the signals at 9.3, 3.0, 2.7, 2.6 and 2.3 ppm and from 2.0 to 0.8 ppm.

The $^1$H-NMR analysis of Camp4 obtained in Exp. ID GEN19 is shown in FIG. 62. Based on the similarities with the spectrum of Camp2 we can confirm that proton transfer occurred. The ratio API:CI was calculated to 1:1.

Figure 63:
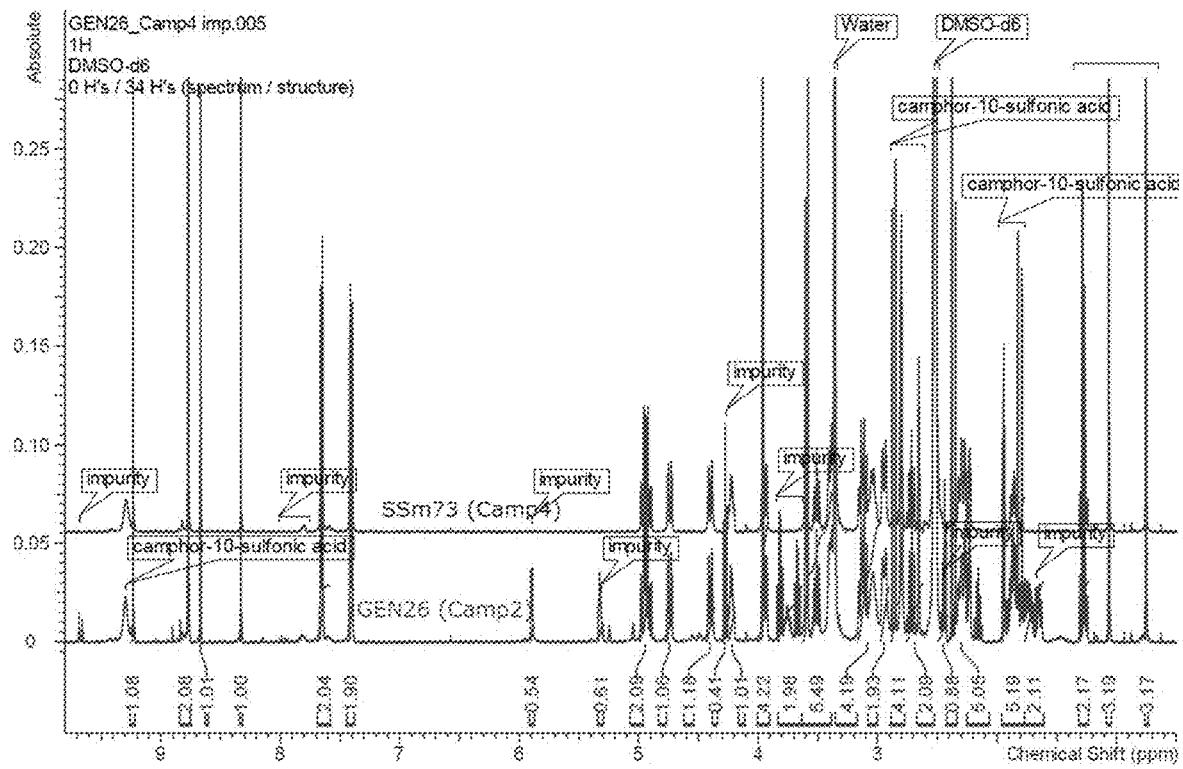
FIG. 63 shows Overlay of $^1$H-NMR spectra (500 MHz, DMSO-d6) of Camp4 (Exp. ID GEN26, red line) and Camp2 (Exp. ID SSm73). The peaks corresponding to the CI were highlighted by the signals at 9.3, 3.0, 2.7, 2.6 and 2.3 ppm and from 2.0 to 0.8 ppm. Additional chemical shifts were identified at 9.66, 5.90, 4.28, 3.86-3.64, 2.44 and 1.6-1.8 ppm.

The $^1$H-NMR analysis of Camp4 obtained in Exp. ID GEN26 is shown in FIG. 63. Based on the similarities with the spectrum of Camp2 we can confirm that proton transfer occurred. The ratio API:CI was calculated to 1:1. Additional resonance shifts were identified in the spectrum of Camp4 from GEN26 which could be attributed to potential impurities also determined by HPLC.

All technical literature or patents cited herein are incorporated by reference in their entirety in the specific context indicated.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the claims listed below, and equivalents thereof.

What is claimed is:

1. A method of inhibiting the activity of c-Met kinase in a subject comprising administering to the subject in need thereof a therapeutically effective amount of a camsylate salt of the compound of formula (1):

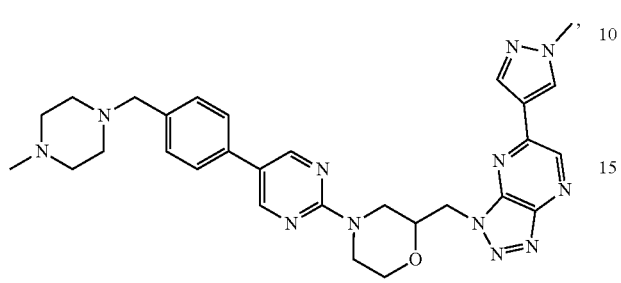

Formula (1)

wherein the camsylate salt has an HT-XRPD pattern with characteristic peaks corresponding substantially to:

| | 2θ [°] | d [Å] | Intensity | or | | 2θ [°] | d [Å] | Intensity |
|---|---|---|---|---|---|---|---|---|
| 1 | 6.29 | 14.04 | 31 | | 1 | 6.34 | 13.92 | 22 |
| 2 | 10.31 | 8.57 | 38 | | 2 | 10.36 | 8.53 | 28 |
| 3 | 12.20 | 7.25 | 45 | | 3 | 12.03 | 7.35 | 28 |
| 4 | 13.70 | 6.46 | 41 | | 4 | 12.26 | 7.21 | 28 |
| 5 | 14.32 | 6.18 | 94 | | 5 | 13.80 | 6.41 | 42 |

-continued

| | 2θ [°] | d [Å] | Intensity | or | | 2θ [°] | d [Å] | Intensity |
|---|---|---|---|---|---|---|---|---|
| 6 | 15.54 | 5.70 | 60 | | 6 | 14.33 | 6.18 | 100 |
| 7 | 16.92 | 5.24 | 100 | | 7 | 14.94 | 5.92 | 39 |
| 8 | 18.19 | 4.87 | 35 | | 8 | 15.52 | 5.70 | 46 |
| 9 | 20.12 | 4.41 | 46 | | 9 | 16.83 | 5.26 | 72 |
| 10 | 21.57 | 4.12 | 43 | | 10 | 18.26 | 4.85 | 27 |
| 11 | 23.36 | 3.81 | 31 | | 11 | 20.11 | 4.41 | 33 |
| 12 | 24.19 | 3.68 | 37 | | 12 | 21.14 | 4.20 | 25 |
| 13 | 26.46 | 3.37 | 26 | | 13 | 21.42 | 4.14 | 28 |
| 14 | 27.79 | 3.21 | 23 | | 14 | 22.35 | 3.98 | 21 |
| 15 | 28.84 | 3.09 | 21 | | 15 | 23.42 | 3.80 | 24 |
| 16 | 29.50 | 3.03 | 22 | | 16 | 23.92 | 3.72 | 24 |
| | | | | | 17 | 26.38 | 3.38 | 18 |
| | | | | | 18 | 27.92 | 3.19 | 16 |
| | | | | | 19 | 28.83 | 3.09 | 19 |
| | | | | | 20 | 29.59 | 3.02 | 15. |

2. The method of claim 1, wherein the compound of formula (1) comprises an(S) enantiomer.

3. The method of claim 1, wherein the camsylate salt has a High-Throughput X-Ray Powder Diffraction (HT-XRPD) pattern comprising characteristic peaks at about 14 to 14.5 2θ (deg) and at about 16 to 17 2θ (deg).

4. The method of claim 1, wherein the subject is suffering from a hyperproliferative disorder.

5. The method of claim 4, wherein the hyperproliferative disorder is lung cancer, gastric cancer, pancreatic cancer, colorectal cancer, ovarian cancer, renal cell cancer, prostate cancer, liver cancer, breast cancer or a brain tumor.

* * * * *